US012624082B2

(12) United States Patent
Hirano et al.

(10) Patent No.: US 12,624,082 B2
(45) Date of Patent: May 12, 2026

(54) T CELL RECEPTORS AND METHODS OF USE THEREOF

(71) Applicant: University Health Network, Toronto (CA)

(72) Inventors: Naoto Hirano, Toronto (CA); Kenji Sugata, Toronto (CA); Kayoko Saso, Toronto (CA)

(73) Assignee: University Health Network, Toronto (CA)

( * ) Notice: Subject to any disclaimer, the term of this patent is extended or adjusted under 35 U.S.C. 154(b) by 1027 days.

(21) Appl. No.: 17/631,831

(22) PCT Filed: Jul. 29, 2020

(86) PCT No.: PCT/IB2020/057171
§ 371 (c)(1),
(2) Date: Jan. 31, 2022

(87) PCT Pub. No.: WO2021/019471
PCT Pub. Date: Feb. 4, 2021

(65) Prior Publication Data
US 2022/0275047 A1 Sep. 1, 2022

Related U.S. Application Data

(60) Provisional application No. 62/880,505, filed on Jul. 30, 2019.

(51) Int. Cl.
| | |
|---|---|
| *C07K 14/725* | (2006.01) |
| *A61K 35/15* | (2025.01) |
| *A61K 35/17* | (2025.01) |
| *A61K 39/00* | (2006.01) |
| *A61K 40/11* | (2025.01) |
| *A61K 40/32* | (2025.01) |
| *A61K 40/42* | (2025.01) |
| *C07K 14/74* | (2006.01) |
| *C07K 16/28* | (2006.01) |
| *C12N 5/0783* | (2010.01) |
| *C12N 15/113* | (2010.01) |

(52) U.S. Cl.
CPC .......... *C07K 14/7051* (2013.01); *A61K 35/15* (2013.01); *A61K 35/17* (2013.01); *A61K 39/00117* (2018.08); *A61K 40/11* (2025.01); *A61K 40/32* (2025.01); *A61K 40/4257* (2025.01); *C07K 14/70539* (2013.01); *C07K 16/2809* (2013.01); *C12N 5/0636* (2013.01); *C12N 5/0646* (2013.01); *C12N 15/1138* (2013.01); *C07K 2317/622* (2013.01); *C12N 2310/14* (2013.01)

(58) Field of Classification Search
CPC ............... C07K 14/7051; A61K 35/17; A61K 39/00117; A61K 40/11; A61K 40/32; C12N 15/1138; A61P 35/00
See application file for complete search history.

(56) References Cited

U.S. PATENT DOCUMENTS

| | | | |
|---|---|---|---|
| 9,181,527 | B2 | 11/2015 | Sentman |
| 2010/0273213 | A1 | 10/2010 | Mineno et al. |
| 2013/0247232 | A1 | 9/2013 | Wang |
| 2013/0287748 | A1 | 10/2013 | June et al. |
| 2022/0275046 | A1 | 9/2022 | Hirano et al. |
| 2022/0275047 | A1 | 9/2022 | Hirano et al. |
| 2022/0281942 | A1 | 9/2022 | Hirano et al. |

FOREIGN PATENT DOCUMENTS

| | | |
|---|---|---|
| CA | 2994829 A1 | 2/2017 |
| CA | 3003728 A1 | 5/2017 |
| CA | 3076337 A1 | 3/2019 |
| CN | 104797711 A | 7/2015 |
| CN | 108795875 A | 11/2018 |
| WO | WO-2017185169 A1 | 11/2017 |

OTHER PUBLICATIONS

Agrewala et al. Peptide Recognition by T-Cell Clones of an HLA-DRB1*1501/*0901 Heterozygous Donor is Promiscuous Only Between Parental Alleles (Year: 1997).*

Anczurowski, M., et al., "Mechanisms underlying the lack of endogenous processing and CLIP-mediated binding of the invariant chain by HLA-DP84Gly," Sci. Rep. 8:4804, Springer, Germany (Mar. 2018).

Butler, M.O., et al., "Ex vivo expansion of human CD8+ T cells using autologous CD4+ T cell help," PloS One 7:e30229, PLOS, United States (2012).

Huang, S., and Kamihira, M., "Development of hybrid viral vectors for gene therapy," Biotechnol. Adv. 31(2):208-23, Elsevier, Netherlands (May 2013).

International Search Report and Written Opinion for International Application PCT/IB2020/057171, Canadian Intellectual Property Office, Canada, mailed on Oct. 15, 2020, 14 pages.

Yamashita, Y., et al., "HLA-DP84Gly constitutively presents endogenous peptides generated by the class I antigen processing pathway," Nat. Commun. 8:15244, Springer, Germany (May 2017).

Bhatia, R., et al., "Cancer-associated mucins: role in immune modulation and metastasis," Cancer metastasis reviews 38(1-2):223-236, Springer Nature, Germany (Jun. 2019).

(Continued)

*Primary Examiner* — Daniel E Kolker
*Assistant Examiner* — Brian Hartnett
(74) *Attorney, Agent, or Firm* — Sterne, Kessler, Goldstein & Fox P.L.L.C.

(57) ABSTRACT

The present disclosure is directed recombinant T cell receptors capable of binding a MUC5AC epitope and nucleic acid molecules encoding the same. In some aspects, the nucleic acid molecules further comprise a second nucleotide sequence, wherein the second nucleotide sequence or the polypeptide encoded by the second nucleotide sequence inhibits the expression of an endogenous TCR. Other aspects of the disclosure are directed to vectors comprising the nucleic acid molecule and cells comprising the recombinant TCR, the nucleic acid molecule, or the vector. Still other aspects of the disclosure are directed to methods of using the same. In some aspects, the methods comprise treating a cancer in a subject in need thereof.

19 Claims, 6 Drawing Sheets

Specification includes a Sequence Listing.

(56)            References Cited

OTHER PUBLICATIONS

Gold, D.V., et al., "Mapping PAM4 (clivatuzumab), a monoclonal antibody in clinical trials for early detection and therapy of pancreatic ductal adenocarcinoma, to MUC5AC mucin," Molecular cancer 12(1):143, BioMed Central, United Kingdom (Nov. 2013).

Hoshi, H., et al., "MUC5AC protects pancreatic cancer cells from TRAIL-induced death pathways," International journal of oncology 42(3):887-893, Spandidos Publications, Greece (Mar. 2013).

Patel, S.P., et al., "Anti-tumor activity of a novel monoclonal antibody, NPC-1C, optimized for recognition of tumor antigen MUC5AC variant in preclinical models," Cancer immunology immunotherapy 62(6):1011-1019, Springer Nature, Germany (Jun. 2013).

Sanchez, C., et al., "Combining T-cell immunotherapy and anti-androgen therapy for prostate cancer," Prostate cancer and prostatic diseases 16(2):123-131, Springer Nature, Germany (Jun. 2013).

Chen, X., et al., "Lentiviral vectors encoding human MUC1-specific, MHC-unrestricted single-chain TCR and a fusion suicide gene: potential for universal and safe cancer immunotherapy," Cancer immunology immunotherapy 58(6):977-987, Springer Nature, Germany (Jun. 2009).

Uniprot, "CD4_HUMAN," Accession No. P01730, accessed at https://www.uniprot.org/uniprotkb/P01730/entry, accessed on Nov. 6, 2025, 13 pages (last updated on Jun. 18, 2025).

Uniprot, "MUC5A_HUMAN," Accession No. P98088, accessed at https://www.uniprot.org/uniprotkb/P98088/entry, accessed on Nov. 6, 2025, 20 pages (last updated on Jun. 18, 2025).

* cited by examiner

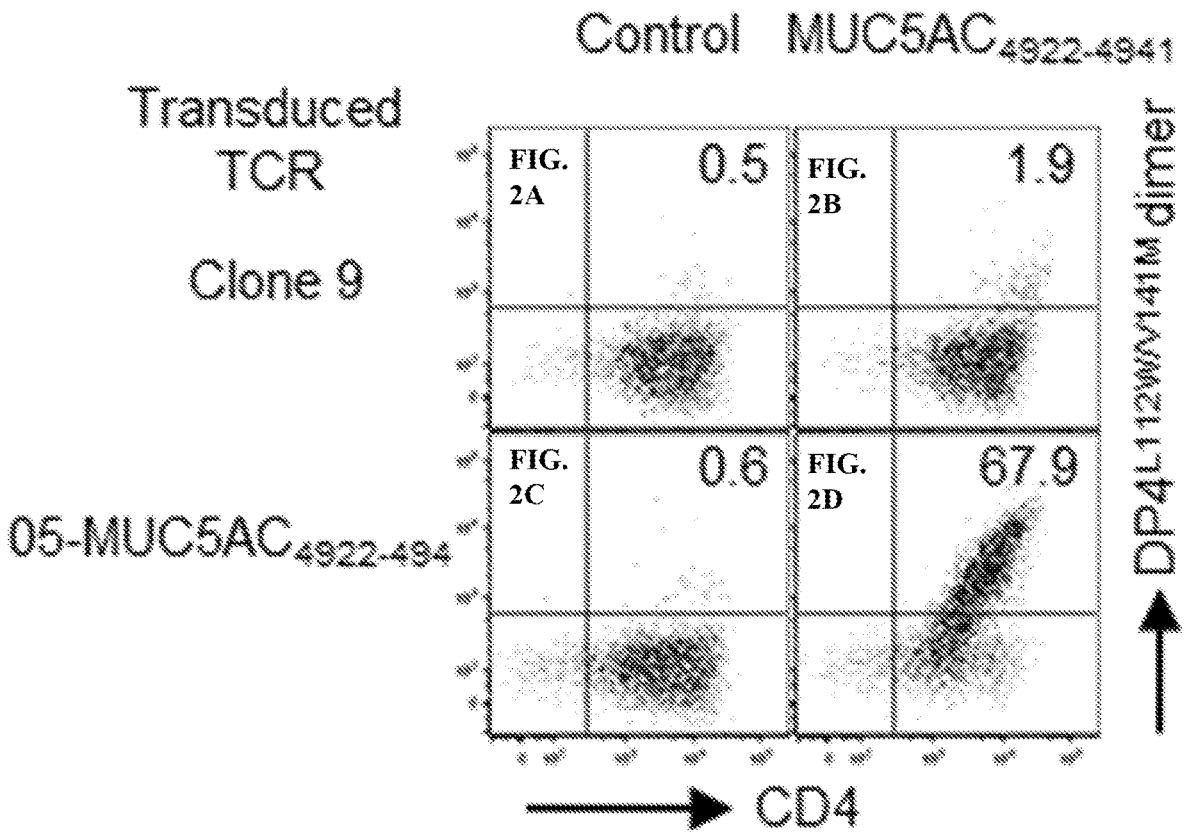

FIG. 3

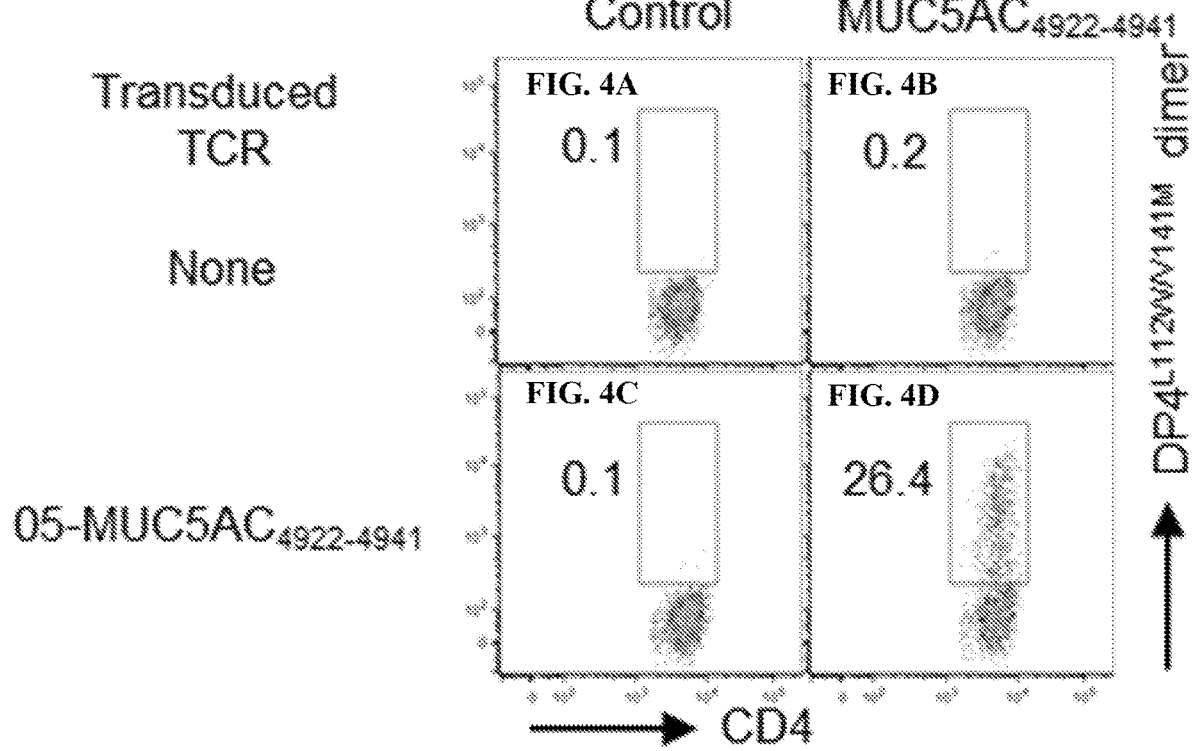

1

T CELL RECEPTORS AND METHODS OF USE THEREOF

CROSS REFERENCE TO RELATED APPLICATIONS

This PCT application claims the priority benefit of U.S. Provisional Application No. 62/880,505, filed Jul. 30, 2019, which is incorporated herein by reference in its entirety.

REFERENCE TO SEQUENCE LISTING SUBMITTED ELECTRONICALLY VIA EFS-WEB

The content of the electronically submitted sequence listing (Name: 4285_014PC01_Seqlisting_ST25.txt, Size: 70,689 bytes; and Date of Creation: Jul. 28, 2020) is incorporated herein by reference in its entirety.

FIELD OF THE DISCLOSURE

The present disclosure provides recombinant T cell receptors ("TCRs") that specifically bind human Mucin 5AC (MUC5AC) and uses thereof.

BACKGROUND OF THE DISCLOSURE

Immunotherapy has emerged as a critical tool in the battle against a variety of diseases, including cancer. T cell therapies are at the forefront of immunotherapeutic development, and adoptive transfer of antitumor T cells has been shown to induce clinical responses in cancer patients. Though many T cell therapies target mutated tumor antigens, the vast majority of neoantigens are not shared and are unique to each patient.

Potential non-mutated antigens outnumber mutated antigens by multiple orders of magnitude. The elucidation of T cell epitopes derived from shared antigens may facilitate the robust development of efficacious and safe adoptive T cell therapies that are readily available to a larger cohort of cancer patients. However, the sheer number of non-mutated antigens and the high polymorphism of HLA genes may have hampered comprehensive analyses of the specificity of antitumor T cell responses toward non-mutated antigens.

SUMMARY OF THE DISCLOSURE

Certain aspects of the present disclosure are directed to a nucleic acid molecule comprising (i) a first nucleotide sequence encoding a recombinant T cell receptor (TCR) or an antigen binding portion thereof that specifically binds human mucin 5AC (MUC5AC) ("anti-MUC5AC TCR"); and (ii) a second nucleotide sequence, wherein the second nucleotide sequence or the polypeptide encoded by the second nucleotide sequence inhibits the expression of an endogenous TCR, wherein the anti-MUC5AC TCR cross competes for binding to human MUC5AC with a reference TCR, which comprises an alpha chain and a beta chain, and wherein the alpha chain comprises an amino acid sequence as set forth in SEQ ID NO: 1 and the beta chain comprises an amino acid sequence as set forth in SEQ ID NO: 2.

Certain aspects of the present disclosure are directed to a nucleic acid molecule comprising (i) a first nucleotide sequence encoding a recombinant T cell receptor (TCR) or an antigen binding portion thereof that specifically binds human MUC5AC ("anti-MUC5AC TCR"); and (ii) a second nucleotide sequence, wherein the second nucleotide sequence or the polypeptide encoded by the second nucleotide sequence inhibits the expression of an endogenous TCR, wherein the anti-MUC5AC TCR binds the same epitope or an overlapping epitope of human MUC5AC as a reference TCR, which comprises an alpha chain and a beta chain, wherein the alpha chain comprises an amino acid sequence as set forth in SEQ ID NO: 1 and the beta chain comprises an amino acid sequence as set forth in SEQ ID NO: 2.

In some aspects, the anti-MUC5AC TCR binds to an epitope of MUC5AC consisting of an amino acid sequence as set forth in SEQ ID NO: 13. In some aspects, the epitope is complexed with an HLA class II molecule. In some aspects, the HLA class II molecule is an HLA-DP, HLA-DQ, or HLA-DR allele, or any combination thereof. In some aspects, the HLA class II molecule is an HLA-DP allele. In some aspects, the HLA class II molecule is an HLA-DP4 allele.

In some aspects, the anti-MUC5AC TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the alpha chain CDR3 comprises an amino acid sequence as set forth in SEQ ID NO: 7.

In some aspects, the beta chain CDR3 of the anti-MUC5AC TCR comprises an amino acid sequence as set forth in SEQ ID NO: 10.

In some aspects, the anti-MUC5AC TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the beta chain CDR3 of the anti-MUC5AC TCR comprises an amino acid sequence as set forth in SEQ ID NO: 10.

In some aspects, the alpha chain CDR3 of the anti-MUC5AC TCR comprises an amino acid sequence as set forth in SEQ ID NO: 7. In some aspects, the alpha chain CDR1 of the anti-MUC5AC TCR comprises an amino acid sequence as set forth in SEQ ID NO: 5. In some aspects, the beta chain CDR1 of the anti-MUC5AC TCR comprises an amino acid sequence as set forth in SEQ ID NO: 8. In some aspects, the alpha chain CDR2 of the anti-MUC5AC TCR comprises an amino acid sequence as set forth in SEQ ID NO: 6. In some aspects, the beta chain CDR2 of the anti-MUC5AC TCR comprises an amino acid sequence as set forth in SEQ ID NO: 9.

In some aspects, the alpha chain variable domain of the anti-MUC5AC TCR comprises an amino acid sequence of a variable domain present in the amino acid sequence set forth SEQ ID NO: 1. In some aspects, the beta chain variable domain of the anti-MUC5AC TCR comprises an amino acid sequence of a variable domain present in the amino acid sequence set forth SEQ ID NO: 2.

In some aspects, the alpha chain of the anti-MUC5AC TCR further comprises a constant region, wherein the constant region is different from endogenous constant region of the alpha chain.

In some aspects, the alpha chain of the anti-MUC5AC TCR further comprises a constant region, wherein the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1.

In some aspects, the alpha chain constant region comprises an amino acid sequence comprising at least 1, at least 2, at least 3, at least 4, or at least 5 amino acid substitutions relative to a constant region present in the amino acid sequence set forth SEQ ID NO: 1.

In some aspects, the beta chain of the anti-MUC5AC TCR further comprises a constant region, wherein the constant region is different from endogenous constant regions of the beta chain.

In some aspects, the beta chain of the anti-MUC5AC TCR further comprises a constant region, wherein the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2.

In some aspects, the beta chain constant region comprises an amino acid sequence comprising at least 1, at least 2, at least 3, at least 4, or at least 5 amino acid substitutions relative to a constant region present in the amino acid sequence set forth SEQ ID NO: 2.

In some aspects, the alpha chain of the anti-MUC5AC TCR comprises an amino acid sequence as set forth in SEQ ID NO: 1. In some aspects, the beta chain of the anti-MUC5AC TCR comprises an amino acid sequence as set forth in SEQ ID NO: 2.

In some aspects, the second nucleotide sequence is one or more siRNAs that reduce the expression of endogenous TCRs. In some aspects, the one or more siRNAs are complementary to a target sequence within a nucleotide sequence encoding a constant region of the endogenous TCRs. In some aspects, the one or more siRNAs comprise one or more nucleotide sequences selected from the group consisting of SEQ ID NOs: 25-28.

In some aspects, the anti-MUC5AC TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

In some aspects, the alpha chain comprises a signal peptide, the beta chain comprises a signal peptide, or both the alpha chain and the beta chain comprise a single peptide. In some aspects, the signal peptide comprises an amino acid sequence selected from the amino acid sequences set forth in SEQ ID NOs: 20-22 and any combination thereof.

Certain aspects of the present disclosure are directed to a vector comprising a nucleic acid molecule disclosed herein. In some aspects, the vector is a viral vector, a mammalian vector, or bacterial vector. In some aspects, the vector is a retroviral vector. In some aspects, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector. In some aspects, the vector is a lentivirus.

Certain aspects of the present disclosure are directed to a T cell receptor (TCR) or an antigen binding portion thereof comprising the alpha chain variable domain of an anti-MUC5AC TCR disclosed herein and the beta chain variable domain of an anti-MUC5AC TCR disclosed herein.

Certain aspects of the present disclosure are directed to a recombinant T cell receptor (TCR) or an antigen binding portion thereof that specifically binds human MUC5AC ("an anti-MUC5AC TCR"), which cross competes for binding to human MUC5AC with a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-MUC5AC TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to a constant region present in the amino acid sequence set forth in SEQ ID NO: 1 or the beta chain constant region comprises an amino acid sequence having a least 1, at least 2, at least 3, at least 4, or at least 5 amino acid substitutions relative to a constant region present in the amino acid sequence of SEQ ID NO: 2.

Certain aspects of the present disclosure are directed to a recombinant T cell receptor (TCR) or an antigen binding portion thereof that specifically binds human MUC5AC ("an anti-MUC5AC TCR"), which binds the same epitope or an overlapping epitope of human MUC5AC as a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-MUC5AC TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to a constant region present in the amino acid sequence set forth in SEQ ID NO: 1 or the beta chain constant region comprises an amino acid sequence having a least 1, at least 2, at least 3, at least 4, or at least 5 amino acid substitutions relative to a constant region present in the amino acid sequence set forth in SEQ ID NO: 2.

In some aspects, the anti-MUC5AC TCR binds to an epitope of MUC5AC consisting of an amino acid sequence as set forth in SEQ ID NO: 13. In some aspects, the epitope is complexed with an HLA class II molecule. In some aspects, the HLA class II molecule is an HLA-DP, HLA-DQ, or HLA-DR allele, or any combination thereof. In some aspects, the HLA class II molecule is an HLA-DP allele. In some aspects, the HLA class II molecule is selected from an HLA-DP4 allele.

In some aspects, the alpha chain of the anti-MUC5AC TCR comprises a variable domain comprising an alpha chain CDR1, an alpha chain CDR2, and an alpha chain CDR3; and wherein the beta chain of the anti-MUC5AC TCR comprises variable domain comprising a beta chain CDR1, a beta chain CDR2, and a beta chain CDR3; wherein the alpha chain CDR3 of the anti-MUC5AC comprises an amino acid sequence as set forth in SEQ ID NO: 7.

In some aspects, the beta chain CDR3 of the anti-MUC5AC TCR comprises an amino acid sequence as set forth in SEQ ID NO: 10.

In some aspects, the alpha chain of the anti-MUC5AC TCR comprises a variable domain comprising an alpha chain CDR1, an alpha chain CDR2, and an alpha chain CDR3; wherein the beta chain of the anti-MUC5AC TCR comprises a variable domain comprising a beta chain CDR1, a beta chain CDR2, and a beta chain CDR3; and wherein the beta chain CDR3 of the anti-MUC5AC TCR comprises an amino acid sequence as set forth in SEQ ID NO: 10.

In some aspects, the alpha chain CDR3 of the anti-MUC5AC TCR comprises an amino acid sequence as set forth in SEQ ID NO: 7. In some aspects, the alpha chain CDR1 of the anti-MUC5AC TCR comprises an amino acid sequence as set forth in SEQ ID NO: 5. In some aspects, the beta chain CDR1 of the anti-MUC5AC TCR comprises an amino acid sequence as set forth in SEQ ID NO: 8. In some aspects, the alpha chain CDR2 of the anti-MUC5AC TCR comprises an amino acid sequence as set forth in SEQ ID NO: 6. In some aspects, the beta chain CDR2 of the anti-MUC5AC TCR comprises an amino acid sequence as set forth in SEQ ID NO: 9.

In some aspects, the alpha chain variable domain of the anti-MUC5AC TCR comprises an amino acid sequence of a variable domain present in the amino acid sequence set forth in SEQ ID NO: 1. In some aspects, the beta chain variable domain of the anti-MUC5AC TCR comprises an amino acid sequence of a variable domain present in the amino acid sequence set forth in SEQ ID NO: 2.

In some aspects, the alpha chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 1.

In some aspects, the beta chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 2.

In some aspects, the alpha chain of the anti-MUC5AC TCR comprises an amino acid sequence as set forth in SEQ ID NO: 1. In some aspects, the beta chain of the anti-MUC5AC TCR comprises an amino acid sequence as set forth in SEQ ID NO: 2.

In some aspects, the alpha chain comprises a signal peptide, the beta chain comprises a signal peptide, or both the alpha chain and the beta chain comprise a single peptide. In some aspects, the signal peptide comprises an amino acid sequence selected from the amino acid sequences set forth in SEQ ID NOs: 20-22 and any combination thereof.

Certain aspects of the present disclosure are directed to a bispecific TCR comprising a first antigen-binding domain and a second antigen-binding domain, wherein the first antigen-binding domain comprises an TCR or an antigen-binding portion thereof disclosed herein.

In some aspects, the first antigen-binding domain comprises a single chain variable fragment ("scFv"). In some aspects, the second antigen-binding domain binds specifically to a protein expressed on the surface of a T cell. In some aspects, the second antigen-binding domain binds specifically to CD3. In some aspects, the second antigen-binding domain comprises an scFv. In some aspects, the first antigen-binding domain and the second antigen-binding domain are linked or associated by a covalent bond. In some aspects, the first antigen-binding domain and the second antigen-binding domain are linked by a peptide bond.

Certain aspects of the present disclosure are directed to a cell comprising a nucleic acid molecule disclosed herein, a vector disclosed herein, a TCR disclosed herein, a recombinant TCR disclosed herein, or a bispecific TCR disclosed herein. In some aspects, the cell further expresses CD3. In some aspects, the cell is selected from the group consisting of a T cell, a natural killer (NK) cell, an natural killer T (NKT) cell, or an ILC cell.

Certain aspects of the present disclosure are directed to a method of treating a cancer in a subject in need thereof, comprising administering to the subject a cell disclosed herein. In some aspects, the cancer is selected from the group consisting of melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers.

In some aspects, the cancer is relapsed or refractory. In some aspects, the cancer is locally advanced. In some aspects, the cancer is advanced. In some aspects, the cancer is metastatic.

In some aspects, the cells are obtained from the subject. In some aspects, the cells are obtained from a donor other than the subject.

In some aspects, the subject is preconditioned prior to the administering of the cells. In some aspects, the preconditioning comprises administering to the subject a chemotherapy, a cytokine, a protein, a small molecule, or any combination thereof. In some aspects, the preconditioning comprises administering an interleukin. In some aspects, the preconditioning comprises administering IL-2, IL-4, IL-7, IL-9, IL-15, IL-21, or any combination thereof. In some aspects, the preconditioning comprises administering a preconditioning agent selected from the group consisting of cyclophosphamide, fludarabine, vitamin C, an AKT inhibitor, ATRA, Rapamycin, or any combination thereof. In some aspects, the preconditioning comprises administering cyclophosphamide, fludarabine, or both.

Certain aspects of the present disclosure are directed to a method of engineering an antigen-targeting cell, comprising transducing a cell collected from a subject in need of a T cell therapy with a nucleic acid molecule disclosed herein or a vector disclosed herein. In some aspects, the antigen-targeting cell further expresses CD4. In some aspects, the cell is a T cell or a natural killer (NK) cell.

Certain aspects of the present disclosure are directed to an HLA class II molecule complexed to a peptide, wherein the HLA class II molecule comprises an alpha chain and a beta chain; and wherein the peptide consists of an amino acid sequence as set forth in SEQ ID NO: 13.

In some aspects, the HLA class II molecule is an HLA-DP, HLA-DQ, or HLA-DR allele, or any combination thereof. In some aspects, the HLA class II molecule is an HLA-DP allele. In some aspects, the HLA class II molecule is an HLA-DQ allele. In some aspects, the HLA class II molecule is an HLA-DR allele. In some aspects, the HLA class II molecule is a monomer. In some aspects, the HLA class II molecule is a dimer. In some aspects, the HLA class II molecule is a trimer. In some aspects, the HLA class II molecule is a tetramer. In some aspects, the HLA class II molecule is a pentamer.

Certain aspects of the present disclosure are directed to an antigen presenting cell (APC), comprising an HLA class II molecule disclosed herein. In some aspects, the HLA class II molecule is expressed on the surface of the APC.

Certain aspects of the present disclosure are directed to a method of enriching a target population of T cells obtained from a human subject, comprising contacting the T cells with an HLA class II molecule disclosed herein or an APC disclosed herein, wherein following the contacting, the enriched population of T cells comprises a higher number of T cells capable of binding the HLA class II molecule relative to the number of T cells capable of binding the HLA class II molecule prior to the contacting.

Certain aspects of the present disclosure are directed to a method of enriching a target population of T cells obtained from a human subject, comprising contacting the T cells in vitro with a peptide, wherein the peptide consists of an amino acid sequence as set forth in SEQ ID NO: 13, wherein following the contacting, the enriched population of T cells comprises a higher number of T cells capable of targeting a tumor cell relative to the number of T cells capable of targeting a tumor cell prior to the contacting. In some aspects, the T cells obtained from the human subject are tumor infiltrating lymphocytes (TIL).

Certain aspects of the present disclosure are directed to a method of treating a tumor in a subject in need thereof, comprising administering to the subject one or more enriched T cells disclosed herein.

Certain aspects of the present disclosure are directed to a method of enhancing cytotoxic T cell-mediated targeting of cancer cells in a subject afflicted with a cancer, comprising administering to the subject a peptide having an amino acid sequence as set forth in SEQ ID NO: 13.

Certain aspects of the present disclosure are directed to a cancer vaccine comprising a peptide having an amino acid sequence as set forth in SEQ ID NO: 13.

Certain aspects of the present disclosure are directed to a method of selecting a T cell capable of targeting a tumor cell, comprising contacting a population of isolated T cells in vitro with a peptide, wherein the peptide consists of an amino acid sequence as set forth in SEQ ID NO: 13. In some aspects, the T cell is a tumor infiltrating lymphocytes (TIL).

BRIEF DESCRIPTION OF THE DRAWINGS

FIGS. 2A-2D are graphical representations of data illustrating that DP4-restricted ($05-MUC5AC_{4922-4941}$) TCRs isolated from $DP4^{L112W/V141M}$ dimer-positive cells and reconstituted in human TCR-defective $CD4^+$ T cells were functional in a DP4-restricted and antigen-specific manner. $05-MUC5AC_{4922-4941}$ were cloned from $DP4^{L112W/V141M}$ dimer-positive cells, reconstituted in TCR-defective Jurkat 76/CD4 cells, and stained by the respective $DP4^{L112W/V141M}$ dimers.

Figure 3:
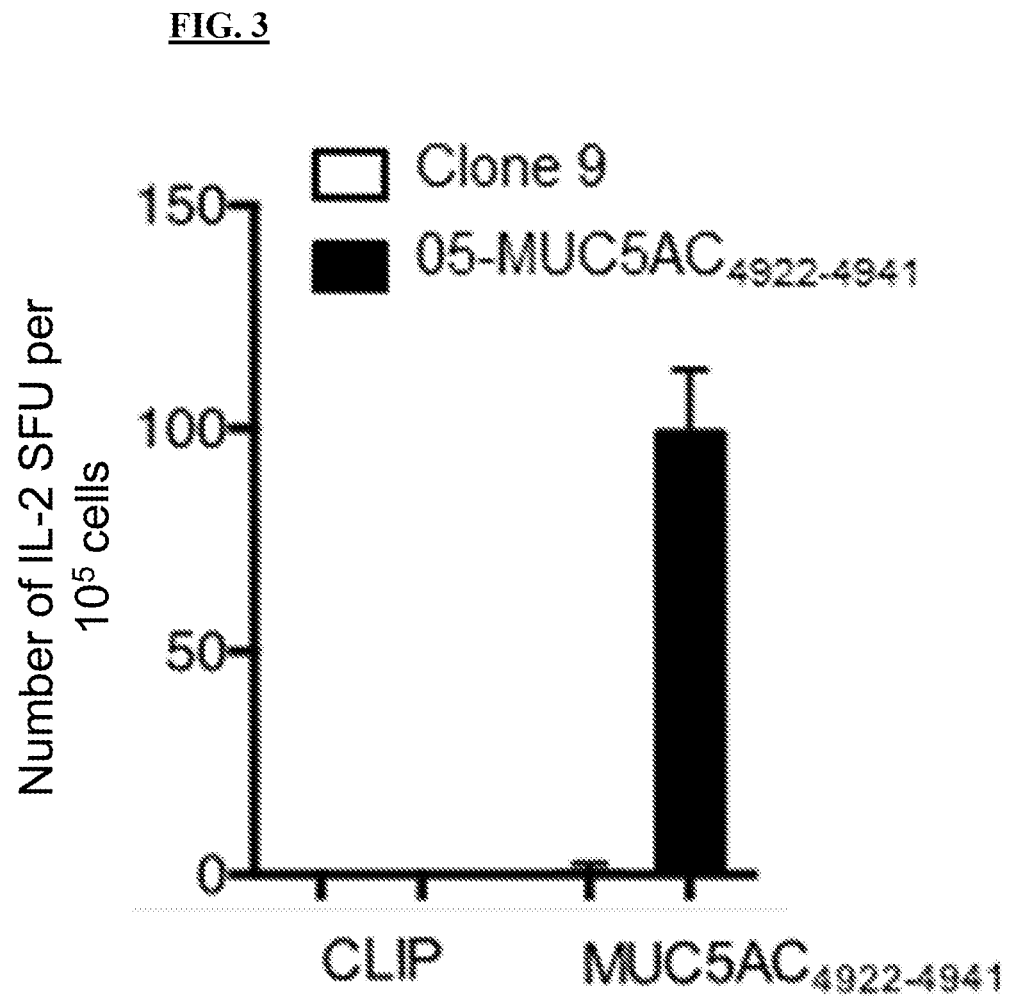

FIG. 3 is a bar graph illustrating the results of IL-2 EPISPOT assays of $05-MUC5AC_{4922-4941}$ stimulated by aAPCs pulsed with $MUC5AC_{4922-4941}$ peptides in IL-2 ELISPOT assays. DP4/WT1 (clone 9) TCR was used as a negative control. At least 2 independent experiments were performed. Bars and error bars represent the mean±SD of results in triplicate experiments.

FIGS. 4A-4E are graphical representations of data showing that DP4-restricted $MUC5AC_{4922-4941}$ TCRs isolated from $DP4^{L112W/V141M}$ dimer-positive cells and reconstituted in human primary $CD4^+$ T cells were functional in a DP4-restricted and antigen-specific manner. $05-MUC5AC_{4922-4941}$ were retrovirally transduced into human primary $CD4^+$ T cells and stained with the respective $DP4^{L112W/V141M}$ dimers. *P<0.05 by Student's t-test. Bars and error bars represent the mean±SD of results in triplicate experiments (FIG. 4E).

DETAILED DESCRIPTION OF THE DISCLOSURE

Figure 1A:
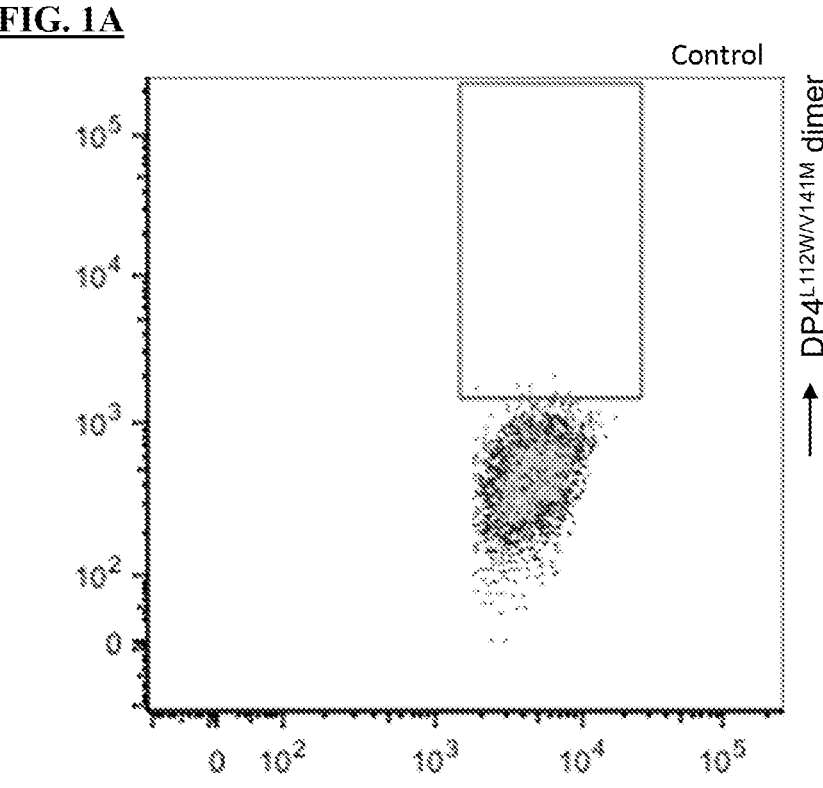
FIGS. 1A-1B are graphical representations of $DP4^{L112W/V141M}$ dimer staining of peptide-specific $CD4^+$ T cells from melanoma patients. Primary $CD4^+$ T cells were purified from six $DP4^+$ melanoma patients and stimulated with DP4-expressing aAPCs individually pulsed with $MUC5AC_{4922-4941}$ peptides and stained with cognate $DP4^{L112W/V141M}$ dimers. Examples of $DP4^{L112W/V141M}$ dimer staining are shown.

The present disclosure is directed to TCRs or antigen binding portions thereof that specifically bind to an epitope on MUC5AC, nucleic acid molecules that encode the same, and cells that comprise the TCR or the nucleic acid molecule. Some aspects of the present disclosure are directed to methods of treating a cancer in a subject in need thereof. Other aspects of the present disclosure are directed to HLA class II molecules complexed to a peptide comprising the epitope of MUC5AC.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "T cell receptor" (TCR), as used herein, refers to a heteromeric cell-surface receptor capable of specifically interacting with a target antigen. As used herein, "TCR" includes but is not limited to naturally occurring and nonnaturally occurring TCRs; full-length TCRs and antigen binding portions thereof; chimeric TCRs; TCR fusion constructs; and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (MHC; also referred to herein as complexed with an HLA molecule, e.g., an HLA class II molecule). A TCR recognizes and binds to the peptide:HLA complex and recruits CD8 (for MHC Class I molecules) or CD4 (for MHC class II molecules), activating the TCR. The activated TCR initiates downstream signaling and an immune response, including the destruction of the EPC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprises a transmembrane region and a short cytoplasmic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region, while CDR1 and CDR2 are believed to primarily recognize the HLA molecule.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD4, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic CDRs.

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen and/or an epitope can be specific to a certain tissue, such as a cancer cell, or it can be broadly expressed. In addition, fragments of larger molecules can act as antigens. In one aspect, antigens are tumor antigens. An epitope can be present in a longer polypeptide (e.g., in a protein), or an epitope can be present as a fragment of a longer polypeptide. In some aspects, an epitope is complexed with a major histocompatibility complex (MEW; also referred to herein as complexed with an HLA molecule, e.g., an HLA class 1 molecule).

"MUC5AC" or "mucin 5AC," as used herein, refers to a human gel-forming glycoprotein of gastric and respiratory tract epithelia that protects the mucosa from infection and chemical damage by binding to inhaled microorganisms and particles that are subsequently removed by the mucocilary system.

As used herein, MUC5AC refers to not only the full-length canonical sequence, but also variants and fragments thereof. The amino acid sequence of MUC5AC (SEQ ID NO: 16) is provided in Table 1 (UniProtKB— P98088).

TABLE 1

| MUC5AC Amino Acid Sequence |
|---|
| MSVGRRKLALLWALALALACTRHTGHAQDGSSESSYKHHPALSPIARGPSGVPLRGATVFPSLRTIPVVRASNPAKN |
| GRVCSTWGSPHYKTFDGDVFRFPGLCNYVFSEHCGAAYEDFNIQLRRSQESAAPTLSRVLMKVDGVVIQLTKGSVLV |
| NGHPVLLPFSQSGVLIQQSSSYTKVEARLGLVLMWNHDDSLLLELDTKYANKTCGLCGDFNGMPVVSELLSHNTKLT |
| PMEFGNLQKMDDPTDQCQDPVPEPPRNCSTGFGICEELLHGQLFSGCVALVDVGSYLEACRQDLCFCEDTDLLSCVC |
| HTLAEYSRQCTHAGGLPQDWRGPDFCPQKCPNNMQYHECRSPCADTCSNQEHSRACEDHCVAGCFCPEGTVLDDIGQ |
| TGCVPVSKCACVYNGAAYAPGATYSTDCTNCTCSGGRWSCQEVPCPGTCSVLGGAHFSTFDGKQYTVHGDCSYVLTK |
| PCDSSAFTVLAELRRCGLTDSETCLKSVTLSLDGAQTVVVIKASGEVFLNQIYTQLPISAANVTIFRPSTFFIIAQT |
| SLGLQLNLQLVPTMQLFMQLAPKLRGQTCGLCGNFNSIQADDFRTLSGVVEATAAAFFNTFKTQAACPNIRNSFEDP |
| CSLSVENEKYAQHWCSQLTDADGPFGRCHAAVKPGTYYSNCMFDTCNCERSEDCLCAALSSYVHACAAKGVQLGGWR |
| DGVCTKPMTTCPKSMTYHYHVSTCQPTCRSLSEGDITCSVGFIPVDGCICPKGTFLDDTGKCVQASNCPCYHRGSMI |
| PNGESVHDSGAICTCTHGKLSCIGGQAPAPVCAAPMVFFDCRNATPGDTGAGCQKSCHTLDMTCYSPQCVPGCVCPD |
| GLVADGEGGCITAEDCPCVHNEASYRAGQTIRVGCNTCTCDSRMWRCTDDPCLATCAVYGDGHYLTFDGQSYSFNGD |
| CEYTLVQNHCGGKDSTQDSFRVVTENVPCGTTGTTCSKAIKIFLGGFELKLSHGKVEVIGTDESQEVPYTIRQMGIY |
| LVVDTDIGLVLLWDKKTSIFINLSPEFKGRVCGLCGNFDDIAVNDFATRSRSVVGDVLEFGNSWKLSPSCPDALAPK |
| DPCTANPFRKSWAQKQCSILHGPTFAACHAHVSPARYYEACVNDACACDSGGDCECFCTAVAAYAQACHEVGLCVSW |
| RTPSICPLPCDYYNPEGQCEWHYQPCGVPCLRTCRNPRGDCLRDVRGLEGCYPKCPPEAPIFDEDKMQCVATCPTPP |
| LPPRCHVHGKSYRPGAVVPSDKNCQSCLCTERGVECTYKAEACVCTYNGQRFHPGDVIYHTTDGTGGCISARCGANG |
| TIERRVYPCSPTTPVPPTTFSFSTPPLVVSSTHTPSNGPSSAHTGPPSSAWPTTAGTSPRTRLPTASASLPPVCGEK |
| CLWSPWMDVSRPGRGTDSGDFDTLENLRAHGYRVCESPRSVECRAEDAPGVPLRALGQRVQCSPDVGLTCRNREQAS |
| GLCYNYQIRVQCCTPLPCSTSSSPAQTTPPTTSKTTETRASGSSAPSSTPGTVSLSTARTTPAPGTATSVKKTFSTP |
| SPPPVPATSTSSMSTTAPGTSVVSSKPTPTEPSTSSCLQELCTWTEWIDGSYPAPGINGGDFDTFQNLRDEGYTFCE |
| SPRSVQCRAESFPNTPLADLGQDVICSHTEGLICLNKNQLPPICYNYEIRIQCCETVNVCRDITRLPKTVATTRPTP |
| HPTGAQTQTTFTTHMPSASTEQPTATSRGGPTATSVTQGTHTTLVTRNCHPRCTWTKWFDVDFPSPGPHGGDKETYN |
| NIIRSGEKICRRPEEITRLQCRAKSHPEVSIEHLGQVVQCSREEGLVCRNQDQQGPFKMCLNYEVRVLCCETPRGCH |
| MTSTPGSTSSSPAQTTPSTTSKTTETQASGSSAPSSTPGTVSLSTARTTPAPGTATSVKKTFSTPSPPPVPATSTSS |
| MSTTAPGTSVVSSKPTPTEPSTSSCLQELCTWTEWIDGSYPAPGINGGDFDTFQNLRDEGYTFCESPRSVQCRAESF |
| PNTPLADLGQDVICSHTEGLICLNKNQLPPICYNYEIRIQCCETVNVCRDITRPPKTVATTRPTPHPTGAQTQTTFT |
| THMPSASTEQPTATSRGGPTATSVTQGTHTTPVTRNCHPRCTWTTWFDVDFPSPGPHGGDKETYNNIIRSGEKICRR |
| PEEITRLQCRAKSHPEVSIEHLGQVVQCSREEGLVCRNQDQQGPFKMCLNYEVRVLCCETPKGCPVTSTPVTAPSTP |
| SGRATSPTQSTSSWQKSRTTTLVTTSTTSTPQTSTTYAHTTSTTSAPTARTTSAPTTRTTSASPASTTSGPGNTPSP |
| VPTTSTISAPTTSITSAPTTSTTSAPTSSTTSGPGTTPSPVPTTSITSAPTTSTTSAPTTSTTSARTSSTTSATTTS |
| RISGPETTPSPVPTTSTTSATTTSTTSAPTTSTTSAPTSSTTSSPQTSTTSAPTTSTTSGPGTTPSPVPTTSTTSAP |
| TTRTTSAPKSSTTSAATTSTTSGPETTPRPVPTTSTTSSPTTSTTSAPTTSTTSASTTSTTSGAGTTPSPVPTTSTT |
| SAPTTSTTSAPISSTTSATTTSTTSGPGTTPSPVPTTSTTSAPTTSTTSGPGTTPSAVPTTSITSAPTTSTNSAPIS |
| STTSATTTSRISGPETTPSPVPTASTTSASTTSTTSGPGTTPSPVPTTSTISVPTTSTTSASTTSTTSASTTSTTSG |
| PGTTPSPVPTTSTTSAPTTSTTSAPTTSTISAPTTSTTSATTTSTTSAPTPRRTSAPTTSTISASTTSTTSATTTST |
| TSATTTSTISAPTTSTTLSPTTSTTSTTITSTTSAPISSTTSTPQTSTTSAPTTSTTSGPGTTSSPVPTTSTTSAPT |
| TSTTSAPTTRTTSVPTSSTTSTATTSTTSGPGTTPSPVPTTSTTSAPTTRTTSAPTTSTTSAPTTSTTSAPTSSTTS |
| ATTTSTISVPTTSTTSVPGTTPSFVPTTSTISVPTTSTTSASTTSTTSGPGTTPSPVPTTSTTSAPTTSTTSAPTTS |
| TISAPTTSTPSAPTTSTTLAPTTSTTSAPTTSTTSTPTSSTTSSPQTSTTSASTTSITSGPGTTPSPVPTTSTTSAP |
| TTSTTSAATTSTISAPTTSTTSAPTTSTTSASTASKTSGLGTTPSPIPTTSTTSPPTTSTTSASTASKTSGPGTTPS |
| PVPTTSTIFAPRTSTTSASTTSTTPGPGTTPSPVPTTSTASVSKTSTSHVSISKTTHSQPVTRDCHLRCTWTKWFDI |
| DFPSPGPHGGDKETYNNIIRSGEKICRRPEEITRLQCRAESHPEVSIEHLGQVVQCSREEGLVCRNQDQQGPFKMCL |
| NYEVRVLCCETPKGCPVTSTPVTAPSTPSGRATSPTQSTSSWQKSRTTTLVTTSTTSTPQTSTTSAPTTSTTSAPTT |
| STTSAPTTSTTSTPQTSISSSAPTSSTTSAPTSSTISARTTSIISAPTTSTTSSPTTSTTSATTTSTTSAPTSSTTST |
| PQTSKTSAATSSTTSGSGTTPSPVTTTSTASVSKTSTSHVSVSKTTHSQPVTRDCHPRCTWTKWFDVDFPSPGPHGG |
| DKETYNNIIRSGEKICRRPEEITRLQCRAKSHPEVSIEHLGQVVQCSREEGLVCRNQDQQGPFKMCLNYEVRVLCCE |
| TPKGCPVTSTSVTAPSTPSGRATSPTQSTSSWQKSRTTTLVTSSITSTTQTSTTSAPTTSTTPASIPSTTSAPTTST |
| TSAPTTSTTSAPTTSTTSTPQTTTSAPTSSTTSAPTTSTISAPTTSTISAPTTSTTSAPTASTTSAPTSTSSAPTT |
| NTTSAPTTSTTSAPITSTISAPTTSTTSTPQTSTISSPTTSTTSTPQTSTTSSPTTSTTSAPTTSTTSAPTTSTTST |
| PQTSTSSAPTSSTTSAPTASTISAPTTSTTSFHTTSTTSPPTSSTSSTPQTSKTSAATSSTTSGSOTTPSPVPTTST |
| ASVSKTSTSHVSVSKTTHSQPVTRDCHPRCTWTKWFDVDFPSPGPHGGDKETYNNIIRSGEKICRRPEEITRLQCRA |
| ESHPEVSIEHLGQVVQCSREEGLVCRNQDQQGPFKMCLNYEVRVLCCETPKGCPVTSTPVTAPSTPSGRATSPTQST |
| SSWQKSRTTTINTTSTTSTPQTSTTSAPTTSTIPASTPSTTSAPTTSTTSAPTTSTTSAPTHRTTSGPTTSTTLAPT |
| TSTTSAPTTSTNSAPTTSTISASTTSTISAPTTSTISSPTSSTTSTPQTSKTSAATSSTTSGSGTTPSPVPTTSTTS |
| ASTTSTTSAPTTSTTSGPGTTPSPVPSTSTTSAATTSTTSAPTTRTTSAPTSSMTSGPGTTPSPVPTTSTTSAPTTS |
| TTSGPGTTPSPVPTTSTTSAPITSTTSGPGSTPSPVPTTSTTSAPTTSTTSASTASTTSGPOTTPSPVPTTSTTSAP |
| TTRTTSASTASTTSGPGSTPSPVPTTSTTSAPTTRTTPASTASTTSGPGTTPSPVPTTSTTSASTTSTISLPTTSTT |
| SAPITSMTSGPGTTPSPVPTTSTTSAPTTSTTSASTASTTSGPGTTPSPVPTTSTTSAPTTSTTSASTASTTSGPGT |
| SLSPVPTTSTTSAPTTSTTSCPGTTPSPVPTTSTTSAPTTSTTSCPGTTPSPVPTTSTTSPVSKTSTSHLSVSKTTHS |
| QPVTSDCHPLCAWTKWFDVDFPSPOPHGGDKETYNNTIRSGEKTCRRPEETTRLQCRAESHPEVNTEHLGQVVQCSR |
| EEGLVCRNQDQQGPFKMCLNYEVRVLCCETPROCPVTSVTPYGTSPTNALYPSLSTSMVSASVASTSVASSSVASSS |
| VAYSTQTCFCNVADRLYPAGSTIYRHRDLAGHCYYALCSQDCQVVRGVDSDCPSTTLPPAPATSPSISTSEPVTELG |
| CPNAVPPRKKGETWATPNCSEATCEGNNVISLRPRTCPRVEKPTCANGYPAVKVADQDGCCHHYQCQCVCSGWGDPH |
| YITFDGTYYTFLDNCTYVLVQQIVPVYGHFRVLVDNYFCCAEDGLSCPRSIILEYHQDRVVLTRKPVHGVMTNEIIF |

TABLE 1-continued

MUC5AC Amino Acid Sequence

```
NNKVVSPGFRKNGIVVSRIGVKMYATIPELGVQVMFSGLIFSVEVPFSKFANNTEGQCGTCTNDRKDECRTPRGTVV
ASCSEMSGLWNVSIPDQPACHRPHPTPTTVGPTTVGSTTVGPTTVGSTTVGPTTPPAPCLPSPICQLILSKVFEPCH
TVIPPLLFYEGCVFDRCHMTDLDVVCSSLELYAALCASHDICIDWRGRTGHMCPFTCPADKVYQPCGPSNPSYCYGN
DSASLGALPEAGPITEGCFCPEGMTLFSTSAQVCVPTGCPRCLGPHGEPVKVGHTVGMDCQECTCEAATWTLTCRPK
LCPLPPACPLPGFVPVPAAPQAGQCCPWSCACNTSRCPAPVGCPEGARAIPTYQEGACCPVQNCSWITVCSINGTLY
QPGAVVSSSLCETCRCELPGGPPSDAFVVSCETQICNTHCPVGFEYQEQSGQCCGTCVQVACVTNTSKSPAHLFYPG
ETWSDAGNHCVTHQCEKHQDGLVVVTTKKACPPLSCSLDEARMSKDGCCRFCPPPPPPYQNQSTCAVYHRSLIIQQQ
GCSSSEPVRLAYCRGNCGDSSSMYSLEGNTVEHRCQCCQELRTSLRNVTLHCTDGSSRAFSYTEVEECGCMGRRCPA
PGDTQHSEEAEPEPSQEAESGSWERGVPVSPMH (SEQ ID NO: 16)
```

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class II genes encode MHC class II proteins which are expressed on the surface of professional antigen presenting cells (APCs). Non-limiting examples of professional APCs include monocytes, macrophages, dendritic cells (DCs), and B lymphocytes. Some endothelial and epithelial cells can also express MHC class II molecules after inflammatory signals are activated. Humans lacking functional MHC class II molecules are extremely susceptible to an array of infectious diseases and typically die at a young age.

As used herein, an "HLA class II molecule" or "MHC class II molecule" refers to a protein product of a wild-type or variant HLA class II gene encoding an MHC class II molecule. Accordingly, "HLA class II molecule" and "MHC class II molecule" are used interchangeably herein. A typical MHC Class II molecule comprises two protein chains: an alpha chain and a beta chain. In general, naturally occurring alpha chains and beta chains each comprise a transmembrane domain, which anchors the alpha/beta chain to the cell surface, and an extracellular domain, which carries the antigen and interacts with a TCR and/or CD4 expressed on a T cell.

Both the MEW Class II alpha and beta chains are encoded by the HLA gene complex. The HLA complex is located within the 6p21.3 region on the short arm of human chromosome 6 and contains more than 220 genes of diverse function. The HLA gene complex is highly variant, with over 20,000 HLA alleles and related alleles, including over 250 MHC class II alpha chain alleles and 5,000 MEW class II beta chain alleles, known in the art, encoding thousands of MEW class II proteins (see, e.g., hla.alleles.org, last visited May 20, 2019, which is incorporated by reference herein in its entirety). For example one such HLA-DP allele, DP4 is the most frequently found allele in many ethnic groups.

Three loci in the HLA complex encode MHC Class II proteins: HLA-DP, HLA-DQ, and HLA-DR. HLA-DO and HLA-DM encode proteins that associate with the MEW class II molecule and support its configuration and function.

When the MEW class II molecule is complexed with an antigen peptide, the 10-30 amino acid long antigen peptide binds the peptide-binding groove and is presented extracellularly to CD4+ cells. Both the alpha- and beta-chains fold into two separate domains; alpha-1 and alpha-2 for the alpha polypeptide, and beta-1 and beta-2 for the beta polypeptide. The open-ended peptide-binding groove which holds the presented antigen is found between the alpha-1 and beta-1 domains. Upon interaction with a CD4+ T cell, the MEW class II complex interacts with a T cell receptor (TCR) expressed on the surface of the T cell. In addition, the beta chain of the MHC class II molecule weakly interacts ($K_D$>2 mM) with CD4 expressed on the surface of the T cell. The canonical CD4 amino acid sequence (UniProt-P01730) is provided in Table 2 (SEQ ID NO: 17).

TABLE 2

Human CD4 Amino Acid Sequence

```
MNRGVPFRHLLLVLQLALLPAATQGKKVVLGKKGDTVELTCTASQKKSI
QFHWKNSNQIKILGNQGSFLTKGPSKLNDRADSRRSLWDQGNFPLIIKN
LKIEDSDTYICEVEDQKEEVQLLVFGLTANSDTHLLQGQSLTLTLESPP
GSSPSVQCRSPRGKNIQGGKTLSVSQLELQDSGTWTCTVLQNQKKVEFK
IDIVVLAFQKASSIVYKKEGEQVEFSFPLAFTVEKLTGSGELWWQAERA
SSSKSWITFDLKNKEVSVKRVTQDPKLQMGKKLPLHLTLPQALPQYAGS
GNLTLALEAKTGKLHQEVNLVVMRATQLQKNLTCEVWGPTSPKLMLSLK
LENKEAKVSKREKAVWVLNPEAGMWQCLLSDSGQVLLESNIKVLPTWST
PVQPMALIVLGGVAGLLLFIGLGIFFCVRCRHRRRQAERMSQIKRLLSE
KKTCQCPHRFQKTCSPI (SEQ ID NO: 17)
```

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some aspects, the methods of the present invention can be used to reduce the tumor size of a tumor derived from, for example, bone cancer, renal cancer, prostate cancer, breast cancer, colon cancer, lung cancer, cutaneous or intraocular malignant melanoma, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory.

A refractory cancer refers to a cancer that is not amendable to surgical intervention, and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" or "progressive disease," which can be abbreviated as PD, as used herein, refers to a worsening of one or more symptom associated with a particular disease. For example, disease progression for a subject afflicted with a cancer can include an increase in the number or size of one or more malignant lesions, tumor metastasis, and death.

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

Other examples of analytes and cytokines of the present invention include, but are not limited to chemokine (C—C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO—, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some aspects, the cell that is modified is a lymphocyte, e.g., a T cell or a modified cell that expresses CD4, which can either be obtained from a patient or a donor. The cell can be modified to express an exogenous construct, such as, e.g., a T cell receptor (TCR) disclosed herein, which is incorporated into the cell's genome. In some aspects, the cell is modified to express CD4.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD4 and a TCR disclosed herein. In some aspects, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD4 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MEW Class II molecule loaded with a peptide, an anti-CD4 antibody, a superagonist anti-CD2 antibody, a superagonist anti-CD28 antibody, and a superagonist anti-CD3 antibody.

The terms "conditioning" and "pre-conditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy. In one aspect, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1 (sICAM-1), soluble vascular adhesion molecule 1 (sVCAM-1), or any combination thereof. In another aspect, "conditioning" comprises increasing a serum level of IL-7, IL-15, IP-10, MCP-1, PLGF, CRP, or any combination thereof.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one aspect, "treatment" or "treating" includes a partial remission. In another aspect, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to T Cell Receptors (TCRs) or antigen binding portions thereof that specifically bind to an epitope on MUC5AC, nucleic acid molecules that encode the same, and cells that comprise the TCR or the nucleic acid molecule. Some aspects of the present disclosure are directed to methods of treating a cancer in a subject in need thereof, comprising administering to the subject a cell comprising the TCRs described herein. Other aspects of the present disclosure are directed to an epitope of MUC5AC that the TCRs bind to and HLA class II molecules complexed to a peptide comprising the epitope of MUC5AC.

The T-cell receptor, or TCR, is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains (that is, it is a heterodimer). In 95% of human T cells, the TCR consists of an alpha (a) chain and a beta (β) chain (encoded by TRA and TRB, respectively), whereas in 5% of human T cells, the TCR consists of gamma and delta (γ/δ) chains (encoded by TRG and TRD, respectively). This ratio changes during ontogeny and in diseased states (such as leukemia). It also differs between species. Orthologues of the 4 loci have been mapped in various species. Each locus can produce a variety of polypeptides with constant and variable regions.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

II.A. Nucleic Acid Molecules

Certain aspects of the present disclosure are directed to nucleic acid molecules comprising (i) a first nucleotide sequence encoding a recombinant TCR or an antigen binding portion thereof that specifically binds human MUC5AC ("anti-MUC5AC TCR"); and (ii) a second nucleotide sequence, wherein the second nucleotide sequence or the polypeptide encoded by the second nucleotide sequence inhibits the expression of an endogenous TCR. In some aspects, the second nucleotide sequence is a non-naturally occurring sequence. In other aspects, the second nucleotide sequence is synthetic. In yet other aspects, the second nucleotide sequence comprises a sequence that targets a nucleotide sequence encoding the endogenous TCR. In some aspects, the anti-MUC5AC TCR cross competes for binding to human MUC5AC with a reference TCR. In some aspects, the anti-MUC5AC TCR binds the same epitope or an overlapping epitope of human MUC5AC as a reference TCR.

In some aspects, the reference TCR comprises an alpha chain and a beta chain; wherein the alpha chain comprises a complementarity determining region 1 (CDR1), a CDR2, and a CDR3; wherein the beta chain comprises a CDR1, a CDR2, and a CDR3; and wherein the reference TCR comprises the alpha chain CDR3 set forth in SEQ ID NO: 7 and the beta chain CDR3 set forth in SEQ ID NO: 10. In some aspects, the alpha chain CDR1, CDR2, and CDR3 sequences present in the an amino acid sequence set forth in SEQ ID NO: 1, and reference TCR comprises the beta chain CDR1, CDR2, and CDR3 sequences present in the amino acid sequence set forth in SEQ ID NO: 2. In some aspects, the reference TCR comprises an alpha chain and a beta chain, wherein the alpha chain comprises an amino acid sequence as set forth in SEQ ID NO: 1 and the beta chain comprises an amino acid sequence as set forth in SEQ ID NO: 2.

TABLE 3

| | Alpha Chain and Beta Chain TCR Sequences | |
|---|---|---|
| SEQ ID NO: | TCR Chain | Sequence |
| 1 | Alpha Chain (amino acid) | QTVTQSQPEMSVQEAETVTLSCTYDTSESNYYLFWYKQPPSRQMILVIRQEAYKQQNAT ENRFSVNFQKAAKSFSLKISDSQLGDTAMYFCAFMKRAETSGSRLTFGEGTQLTVNPDI QNPDPAVYQLRDSKSSDKSVCLFTDFDSQTNVSQSKDSDVYITDKTVLDMRSMDFKSNS AVAWSNKSDFACANAFNNSIIPEDTFFPSPESSCDVKLVEKSFETDTNLNFQNLSVIGF RILLLKVAGFNLLMTLRLWSS |

TABLE 3-continued

Alpha Chain and Beta Chain TCR Sequences

| SEQ ID NO: | TCR Chain | Sequence |
|---|---|---|
| 18 | Alpha Chain (nucleotide) | CAGACAGTCACTCAGTCTCAACCAGAGATGTCTGTGCAGGAGGCAGAGACTGTGACCCT GAGTTGCACATATGACACCAGTGAGAGTAATTATTATTTGTTCTGGTACAAACAGCCTC CCAGCAGGCAGATGATTCTCGTTATTCGCCAAGAAGCTTATAAGCAACAGAATGCAACG GAGAATCGTTTCTCTGTGAACTTCCAGAAAGCAGCCAAATCCTTCAGTCTCAAGATCTC AGACTCACAGCTGGGGGACACTGCGATGTATTTCTGTGCTTTCATGAAGCGGGCCGAAA CCAGTGGCTCTAGGTTGACCTTTGGGGAAGGAACACAGCTCACAGTGAATCCTGATATC CAGAACCCTGACCCTGCCGTGTACCAGCTGAGAGACTCTAAATCCAGTGACAAGTCTGT CTGCCTATTCACCGATTTTGATTCTCAAACAAATGTGTCACAAAGTAAGGATTCTGATG TGTATATCACAGACAAAACTGTGCTAGACATGAGGTCTATGGACTTCAAGAGCAACAGT GCTGTGGCCTGGAGCAACAAATCTGACTTTGCATGTGCAAACGCCTTCAACAACAGCAT TATTCCAGAAGACACCTTCTTCCCCAGCCCAGAAAGTTCCTGTGATGTCAAGCTGGTCG AGAAAAGCTTTGAAACAGATACGAACCTAAACTTTCAAAACCTGTCAGTGATTGGGTTC CGAATCCTCCTCCTGAAAGTGGCCGGGTTTAATCTGCTCATGACGCTGCGGCTGTGGTC CAGC |
| 21 | Alpha Chain Signal Peptide (amino acid) | MTRVSLLWAVVVSTCLESGMA |
| 23 | Alpha Chain Sigma Peptide (nucleotide) | ATGACACGTGTTAGCTTGCTGTGGGCAGTCGTGGTCTCCACCTGTCTTGAATCCGGCAT GGCC |
| 2 | Beta Chain (amino acid) | NAGVTQTPKFRVLKTGQSMTLLCAQDMNHEYMYWYRQDPGMGLRLIHYSVGEGTTAKGE VPDGYNVSRLKKQNFLLGLESAAPSQTSVYFCASSYWPTRETQYFGPGTRLLVLEDLKN VFPPEVAVFEPSEAEISHTQKATLVCLATGFYPDHVELSWWVNGKEVHSGVSTDPQPLK EQPALNDSRYCLSSRLRVSATFWQNPRNHFRCQVQFYGLSENDEWTQDRAKPVTQIVSA EAWGRADCGFTSESYQQGVLSATILYEILLGKATLYAVLVSALVLMAMVKRKDSRG |
| 19 | Beta Chain (nucleotide) | AATGCTGGTGTCACTCAGACCCCAAAATTCCGGGTCCTGAAGACAGGACAGAGCATGAC ACTGCTGTGTGCTCAGGATATGAACCATGAATACATGTACTGGTATCGACAAGACCCAG GCATGGGGCTGAGGCTGATTCATTACTCAGTTGGTGAGGGTACAACTGCCAAAGGAGAG GTCCCTGATGGCTACAATGTCTCCAGATTAAAAAAACAGAATTTCCTGCTGGGGTTGGA GTCGGCTGCTCCCTCCCAAACATCTGTGTACTTCTGTGCCAGCAGTTACTGGCCGACGC GGGAGACCCAGTACTTCGGGCCAGGCACGCGGCTCCTGGTGCTCGAGGACCTGAAAAAC GTGTTCCCACCCGAGGTCGCTGTGTTTGAGCCATCAGAAGCAGAGATCTCCCACACCCA AAAGGCCACACTGGTATGCCTGGCCACAGGCTTCTACCCCGACCACGTGGAGCTGAGCT GGTGGGTGAATGGGAAGGAGGTGCACAGTGGGGTCAGCACAGACCCGCAGCCCCTCAAG GAGCAGCCCGCCCTCAATGACTCCAGATACTGCCTGAGCAGCCGCCTGAGGGTCTCGGC CACCTTCTGGCAGAACCCCCGCAACCACTTCCGCTGTCAAGTCCAGTTCTACGGGCTCT CGGAGAATGACGAGTGGACCCAGGATAGGGCCAAACCTGTCACCCAGATCGTCAGCGCC GAGGCCTGGGGTAGAGCAGACTGTGGCTTCACCTCCGAGTCTTACCAGCAAGGGGTCCT GTCTGCCACCATCCTCTATGAGATCTTGCTAGGGAAGGCCACCTTGTATGCCGTGCTGG TCAGTGCCCTCGTGCTGATGGCCATGGTCAAGAGAAAGGATAGCAGAGGC |
| 22 | Beta Chain Signal Peptide (amino acid) | MGAVASALSFSAGPV |
| 24 | Beta Chain Signal Peptide (nucleotide) | ATGGGGGCTGTAGCATCAGCTTTGTCCTTCTCTGCAGGTCCAGTG |
| 20 | Signal Peptide (Fibroin-L derived) | MMRPIVLVLLFATSALA |

II.A.1. TCR Encoded by the First Nucleotide Sequence

The present disclosure is directed to a TCR encoded by the first nucleotide sequence described herein. In some aspects, the anti-MUC5AC TCR encoded by the first nucleotide sequence comprises an alpha chain and a beta chain, wherein the alpha chain comprises a variable domain comprising an alpha chain CDR1, an alpha chain CDR2, and an alpha chain CDR3; and wherein the beta chain comprises variable domain comprising a beta chain CDR1, a beta chain CDR2, and a beta chain CDR3. In some aspects, the anti-MUC5AC TCR comprises an alpha chain CDR3 comprising an amino acid sequence as set forth in SEQ ID NO: 7 (CAFMKRAETSGSRLTF). In some aspects, the anti-MUC5AC TCR comprises a beta chain CDR3 comprising an amino acid sequence as set forth in SEQ ID NO: 10 (CASSYWPTRETQYF). In some aspects, the non-CDR regions in the alpha chain and/or the beta chain are further modified, e.g., substitution or mutation of one amino acid, two amino acids, three amino acids, four amino acids, five amino acids, or six amino acids, thereby the alpha chain and/or the beta chain are not naturally occurring. In some aspects, the substitutions or mutations can improve the TCRs described herein in various ways, e.g., binding affinity, binding specificity, stability, viscosity, or any combination thereof.

In some aspects, the anti-MUC5AC TCR encoded by the first nucleotide sequence comprises an alpha chain CDR1, wherein the alpha chain CDR1 of the anti-MUC5AC TCR comprises an amino acid sequence as set forth in SEQ ID NO: 5 (TSESNYY). In some aspects, the anti-MUC5AC TCR encoded by the first nucleotide sequence comprises a beta chain CDR1, wherein the beta chain CDR1 of the anti-MUC5AC TCR comprises an amino acid sequence as set forth in SEQ ID NO: 8 (MNHEY).

In some aspects, the anti-MUC5AC TCR encoded by the first nucleotide sequence comprises an alpha chain CDR2, wherein the alpha chain CDR2 of the anti-MUC5AC TCR comprises an amino acid sequence as set forth in SEQ ID NO: 6 (QEAYKQQN). In some aspects, the anti-MUC5AC TCR encoded by the first nucleotide sequence comprises a beta chain CDR2, wherein the beta chain CDR2 of the anti-MUC5AC TCR comprises an amino acid sequence as set forth in SEQ ID NO: 9 (SVGEGT).

In some aspects, the anti-MUC5AC TCR encoded by the first nucleotide sequence comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some aspects, the anti-MUC5AC TCR encoded by the first nucleotide sequence comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR encoded by the first nucleotide sequence comprises an alpha chain variable domain present in the alpha chain amino acid sequence set forth in SEQ ID NO: 1.

In some aspects, the anti-MUC5AC TCR encoded by the first nucleotide sequence comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some aspects, the anti-MUC5AC TCR encoded by the first nucleotide sequence comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti-MUC5AC TCR encoded by the first nucleotide sequence comprises a beta chain variable domain present in the amino acid sequence set forth in SEQ ID NO: 2.

In some aspects, the anti-MUC5AC TCR encoded by the first nucleotide further comprises an alpha chain constant region, a beta chain constant region, or both an alpha chain constant region and a beta chain constant region. In some aspects, the anti-MUC5AC TCR encoded by the first nucleotide sequence comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some aspects, the anti-MUC5AC TCR encoded by the first nucleotide sequence comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR encoded by the first nucleotide sequence comprises an alpha chain constant region present in the alpha chain amino acid sequence set forth in SEQ ID NO: 1. In some aspects, the anti-MUC5AC TCR encoded by the first nucleotide further comprises an alpha constant region that is different from endogenous, e.g., naturally occurring, constant regions of the alpha chain. In some aspects, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some aspects, the anti-MUC5AC TCR encoded by the first nucleotide sequence comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some aspects, the anti-MUC5AC TCR encoded by the first nucleotide sequence comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti-MUC5AC TCR encoded by the first nucleotide sequence comprises a beta chain constant region present in the amino acid sequence set forth in SEQ ID NO: 2. In some aspects, the anti-MUC5AC TCR encoded by the first nucleotide further comprises a beta constant region that is different from endogenous, e.g., naturally occurring, constant regions of the beta chain. In some aspects, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain aspects, the anti-MUC5AC TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some aspects, the anti-MUC5AC TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR encoded by the first nucleotide sequence comprises an alpha chain comprising the amino acid sequence set forth in SEQ ID NO: 1.

In certain aspects, the anti-MUC5AC TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some aspects, the anti-MUC5AC TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti-MUC5AC TCR encoded by the first nucleotide sequence comprises a beta chain comprising the amino acid sequence set forth in SEQ ID NO: 2.

In some aspects, the anti-MUC5AC TCR encoded by the first nucleotide sequence comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

In some aspects, the alpha chain of the anti-MUC5AC TCR encoded by the first nucleotide sequence further comprises a signal peptide. Any signal peptide can be used in the anti-MUC5AC TCR alpha chains disclosed herein. In some aspects the signal peptide is a naturally occurring TCR alpha chain signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 21. In some aspects, the signal peptide is a heterologous signal peptide, e.g., a signal peptide derived from a protein other than a TCR alpha chain. In some aspects, the signal peptide is a synthetic signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 20 or 22. In some aspects, the alpha chain of MUC5AC TCR encoded by the first nucleotide sequence does not comprise a signal peptide.

In some aspects, the signal peptide of the alpha chain is encoded by a nucleic acid sequence having at least about 50%, at least about 55%, at least about 60%, at least about 65%, at least about 70%, at least about 75%, at least about 80%, at least about 85%, at least about 90%, at least about 95%, at least about 96%, at least about 97% at least about 98%, at least about 99%, or about 100% sequence identity with the nucleic acid sequence set forth in SEQ ID NO: 23 or 24.

In some aspects, the beta chain of the anti-MUC5AC TCR encoded by the first nucleotide sequence further comprises a signal peptide. Any signal peptide can be used in the anti-MUC5AC TCR beta chains disclosed herein. In some aspects the signal peptide is a naturally occurring TCR beta chain signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 22. In some aspects, the signal peptide is a heterologous signal peptide, e.g., a signal peptide derived from a protein other than a TCR beta chain. In some aspects, the signal peptide is a synthetic signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 20 or 21. In some aspects, the beta chain of MUC5AC TCR encoded by the first nucleotide sequence does not comprise a signal peptide.

In some aspects, the signal peptide of the beta chain is encoded by a nucleic acid sequence having at least about 50%, at least about 55%, at least about 60%, at least about 65%, at least about 70%, at least about 75%, at least about 80%, at least about 85%, at least about 90%, at least about 95%, at least about 96%, at least about 97% at least about 98%, at least about 99%, or about 100% sequence identity with the nucleic acid sequence set forth in SEQ ID NO: 23 or 24.

In some aspects, each of the alpha chain and the beta chain of the anti-MUC5AC TCR encoded by the first nucleotide sequence further comprises a signal peptide. In some aspects, the signal peptide of the alpha chain is the same as the signal peptide of the beta chain. In some aspects, the signal peptide of the alpha chain is different from the signal peptide of the beta chain.

II.A.2. Epitopes

In some aspects, the anti-MUC5AC TCR encoded by the first nucleotide sequence binds the same epitope as a reference TCR. In some aspects, the anti-MUC5AC TCR binds to an epitope of MUC5AC comprising the amino acid sequence set forth in SEQ ID NO: 13 (SGWGD-PHYITFDGTYYTFLD). In some aspects, the anti-MUC5AC TCR binds to an epitope of MUC5AC consisting of an amino acid sequence as set forth in SEQ ID NO: 13. In some aspects, the epitope consists of amino acid residues 4922-4941 of MUC5AC (SEQ ID NO: 16), e.g., "MUC5AC$_{4922\text{-}4941}$."

In certain aspects, the epitope is part of a larger polypeptide, e.g., a peptide that comprises the epitope sequence and (i) one or more additional amino acids N-terminal to the epitope sequence and/or (ii) one or more additional amino acids C-terminal to the epitope sequence. In some aspects, the polypeptide comprising the epitope is at least about 10 amino acids, at least about 11 amino acids, at least about 12 amino acids, at least about 13 amino acids, at least about 14 amino acids, at least about 15 amino acids, at least about 16 amino acids, at least about 17 amino acids, at least about 18 amino acids, at least about 19 amino acids, at least about 20 amino acids, at least about 25 amino acids, at least about 30 amino acids, at least about 35 amino acids, at least about 40 amino acids, at least about 45 amino acids, or at least about 50 amino acids in length. In certain aspects, the polypeptide comprising the epitope is at least about 5 to at least about 10, at least about 5 to at least about 15, at least about 5 to at least about 20, at least about 10 to at least about 15, at least about 10 to at least about 20, at least about 10 to at least about 25, at least about 10 to at least about 30, at least about 10 to at least about 35, at least about 10 to at least about 40, at least about 10 to at least about 45, at least about 10 to at least about 50, at least about 15 to at least about 20, at least about 15 to at least about 25, at least about 15 to at least about 30, at least about 15 to at least about 35, at least about 15 to at least about 40, at least about 15 to at least about 45, or at least about 15 to at least about 50 amino acids in length.

In certain aspects, the polypeptide comprising the epitope comprises the epitope and at least about 1, at least about 2, at least about 3, at least about 4, at least about 5, at least about 6, at least about 7, at least about 8, at least about 9, at least about 10, at least about 11, at least about 12, at least about 13, at least about 14, at least about 15 additional amino acids N-terminal to the epitope. In certain aspects, the polypeptide comprising the epitope comprises the epitope and at least about 1, at least about 2, at least about 3, at least about 4, at least about 5, at least about 6, at least about 7, at least about 8, at least about 9, at least about 10, at least about 11, at least about 12, at least about 13, at least about 14, at least about 15 additional amino acids C-terminal to the epitope.

In certain aspects, the epitope is complexed with an HLA class II molecule. The human leukocyte antigen (HLA) system (the major histocompatibility complex [MHC] in humans) is an important part of the immune system and is controlled by genes located on chromosome 6. It encodes cell surface molecules specialized to present antigenic peptides to the T-cell receptor (TCR) on T cells. (See also Overview of the Immune System.) MHC molecules that present antigen (Ag) are divided into 2 main classes: Class I MHC molecules and Class II MHC molecules.

Class II MHC molecules are present as transmembrane glycoproteins on the surface of professional antigen presenting cells (APCs). Intact class II molecules consist of an alpha chain and a beta chain. The gene encoding the alpha chain of MHC II class molecules is composed of 5 exons, and the gene encoding the beta chain is composed of 6 exons. Exon 1 encodes the leader peptide, exons 2 and 3 encode the two extracellular domains, and exons 4 and 5 contribute to the transmembrane domain and cytoplasmic tail for each of the alpha and beta subunits. Three loci in the HLA complex encode MHC class II proteins: HLA-DR, HLA-DQ, and HLA-DP. T cells that express CD4 molecules react with class II MHC molecules. These lymphocytes often have a cytotoxic function and activate a response to eliminate self-cells infected with intracellular pathogens or to destroy extracellular parasites. Because only professional antigen presenting cells (APCs) express class II MHC molecules, only these cells present antigen for CD4 T cells (CD4 binds to the nonpolymorphic part of the alpha-2 and beta-2 domains of the alpha and beta chains of an MHC class II molecule respectively).

In some aspects, the HLA class II alpha and beta chains are selected from an HLA-DR, HLA-DP, and HLA-DQ allele. In certain aspects, the HLA class II alpha chain is an HLA-DR alpha chain. In some aspects the HLA class II beta chain is an HLA-DR beta chain. In certain aspects, the HLA class II alpha chain is an HLA-DP alpha chain. In some aspects the HLA class II beta chain is an HLA-DP beta chain. In certain aspects, the HLA class II alpha chain is an HLA-DQ alpha chain. In some aspects the HLA class II beta chain is an HLA-DQ beta chain.

Many HLA-DR, HLA-DP, and HLA-DQ alleles are known in the art, and any of the known alleles can be used in the present disclosure. An updated list of HLA alleles is available at hla.alleles.org/(last visited on Jun. 18, 2019), which is incorporated by reference herein in its entirety.

II.A.3 The Second Nucleotide Sequence

The second nucleotide sequence of the nucleic acid molecule disclosed herein can be any sequence or can encode for any polypeptide that is capable of inhibiting the expression of an endogenous TCR. In some aspects, the second nucleotide sequence is one or more siRNAs. In some aspects, the one or more siRNAs are complementary to a target sequence within a nucleotide sequence encoding a constant region of an endogenous TCR. In certain aspects, the one or more siRNAs are complementary to a target sequence within a nucleotide sequence encoding a constant region of wild-type, human TCR. In some aspects, the one or more siRNAs are complementary to a target sequence within a nucleotide sequence encoding a constant region of the alpha chain of wild-type TCR. In some aspects, the one or more siRNAs are complementary to a target sequence within a nucleotide sequence encoding a constant region of the beta chain of wild-type TCR. In some aspects, the one or more siRNAs comprise (i) one or more siRNA's that are complementary to a target sequence within a nucleotide sequence encoding a constant region of the alpha chain of wild-type TCR and (ii) one or more siRNA's that are complementary to a target sequence within a nucleotide sequence encoding a constant region of the beta chain of wild-type TCR.

In some aspects, the one or more siRNAs comprise a nucleotide sequence selected from the group consisting of SEQ ID NOs: 25-28 (Table 4). In some aspects, the second nucleotide sequence of the nucleic acid molecule encodes one or more siRNAs, wherein the one or more siRNAs are complementary to a target sequence within a nucleotide sequence encoding a constant region of the alpha chain of wild-type TCR, and wherein the one or more siRNAs comprise the nucleic acid sequences set forth in SEQ ID NOs: 25 and 26.

TABLE 4

| siRNA Sequences | | |
| --- | --- | --- |
| SEQ ID NO: | siRNA | Sequence (Nucleotides 1-19 are ribonucleotides; nucleotides 20-21 are deoxyribonucleotides) |
| 25 | siRNA-TCRa-1 | GUAAGGAUUCUGAUGUGUAUU |
| 26 | siRNA-TCRa-2 | UACACAUCAGAAUCCUUACUU |
| 27 | siRNA-TCRb-1 | CCACCAUCCUCUAUGAGAUUU |
| 28 | siRNA-TCRb-2 | AUCUCAUAGAGGAUGGUGGUU |

In some aspects, the second nucleotide sequence of the nucleic acid molecule encodes one or more siRNAs, wherein the one or more siRNAs are complementary to a target sequence within a nucleotide sequence encoding a constant region of the beta chain of wild-type TCR, and wherein the one or more siRNAs comprise the nucleic acid sequences set forth in SEQ ID NOs: 27 and 28. In some aspects, the second nucleotide sequence of the nucleic acid molecule encodes one or more siRNAs, wherein the one or more siRNAs comprise (i) one or more siRNAs that are complementary to a target sequence within a nucleotide sequence encoding a constant region of the alpha chain of wild-type TCR, wherein the one or more siRNAs comprise the nucleic acid sequences set forth in SEQ ID NOs: 29 and 30; and (ii) one or more siRNAs that are complementary to a target sequence within a nucleotide sequence encoding a constant region of the beta chain of wild-type TCR, wherein the one or more siRNAs comprise the nucleic acid sequences set forth in SEQ ID NOs: 27 and 28.

In some aspects, the second nucleotide sequence of the nucleic acid molecule comprises SEQ ID NOs: 25-28. In some aspects, the second nucleotide sequence comprises SEQ ID NOs: 25-28, wherein one or more of SEQ ID NOs: 25-28 is separated by one or more nucleic acids that do not encode an siRNA. In certain aspects, the one or more siRNAs are selected from the siRNAs disclosed in U.S. Publication No. 2010/0273213 A1, which is incorporated by reference herein in its entirety.

In some aspects, the second nucleotide sequence of the nucleic acid molecule encodes a protein, wherein the protein is capable of inhibiting the expression of an endogenous, e.g., wild-type, TCR. In some aspects, the second nucleotide sequence encodes Cas9.

II.A.3 Vectors

Certain aspects of the present disclosure are directed to vectors comprising a nucleic acid molecule disclosed herein. In some aspects, the vector is a viral vector. In some aspects, the vector is a viral particle or a virus. In some aspects, the vector is a mammalian vector. In some aspects, the vector is a bacterial vector.

In certain aspects, the vector is a retroviral vector. In some aspects, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular aspects, the vector is an AAV vector. In some aspects, the vector is a lentivirus. In particular aspects, the vector is an AAV vector. In some aspects, the vector is a Sendai virus. In some aspects, the vector is a hybrid vector. Examples of hybrid vectors that can be used in the present disclosure can be found in Huang and Kamihira, Biotechnol. Adv. 31(2): 208-23 (2103), which is incorporated by reference herein in its entirety.

II.B. Recombinant T Cell Receptors (TCRs)

Certain aspects of the present disclosure are directed to recombinant T cell receptors (TCRs) or an antigen binding portion thereof that specifically bind human MUC5AC ("an anti-MUC5AC TCR"). In some aspects, the anti-MUC5AC TCR is encoded by the a nucleic acid molecule disclosed herein.

In some aspects, the anti-MUC5AC TCR cross competes for binding to human MUC5AC with a reference TCR. In some aspects, the anti-MUC5AC TCR binds the same epitope or an overlapping epitope of human MUC5AC as a reference TCR. In some aspects, the reference TCR comprises an alpha chain and a beta chain, and the alpha chain comprises of the reference TCR comprises an amino acid sequence as set forth in SEQ ID NO: 1. In some aspects, the beta chain of the reference TCR comprises an amino acid sequence as set forth in SEQ ID NO: 2.

In some aspects, the anti-MUC5AC TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1. In some aspects, the anti-MUC5AC TCR comprises an alpha chain and a beta chain, wherein the alpha chain comprises a constant region, and wherein the beta chain comprises a constant region; wherein the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some aspects, the anti-MUC5AC TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some aspects, the alpha chain of the anti-MUC5AC TCR comprises a variable domain comprising an alpha chain CDR1, an alpha chain CDR2, and an alpha chain CDR3; and the beta chain of the anti-MUC5AC TCR comprises a variable domain comprising a beta chain CDR1, a beta chain CDR2, and a beta chain CDR3. In some aspects, the anti-MUC5AC TCR comprises an alpha chain CDR3 comprising an amino acid sequence as set forth in SEQ ID NO: 7. In some aspects, the anti-MUC5AC TCR comprises a beta chain CDR3 comprising an amino acid sequence as set forth in SEQ ID NO: 10.

In some aspects, the alpha chain CDR1 of the anti-MUC5AC TCR comprises an amino acid sequence as set forth in SEQ ID NO: 5. In some aspects, the beta chain CDR1 of the anti-MUC5AC TCR comprises an amino acid sequence as set forth in SEQ ID NO: 8.

In some aspects, the alpha chain CDR2 of the anti-MUC5AC TCR comprises an amino acid sequence as set forth in SEQ ID NO: 6. In some aspects, the beta chain CDR2 of the anti-MUC5AC TCR comprises an amino acid sequence as set forth in SEQ ID NO: 9.

In some aspects, the anti-MUC5AC TCR comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some aspects, the anti-MUC5AC TCR comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR comprises an alpha chain variable domain present in the alpha chain amino acid sequence set forth in SEQ ID NO: 1.

In some aspects, the anti-MUC5AC TCR comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some aspects, the anti-MUC5AC TCR comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti-MUC5AC TCR comprises a beta chain variable domain present in the beta chain amino acid sequence set forth in SEQ ID NO: 2.

In some aspects, the anti-MUC5AC TCR encoded by the first nucleotide further comprises an alpha chain constant region, a beta chain constant region, or both an alpha chain constant region and a beta chain constant region. In some aspects, the anti-MUC5AC TCR comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some aspects, the anti-MUC5AC TCR comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR comprises an alpha chain constant region present in the alpha chain amino acid sequence set forth in SEQ ID NO: 1. In some aspects, the anti-MUC5AC TCR encoded by the first nucleotide further comprises an alpha constant region that is different from endogenous, e.g., naturally occurring, constant regions of the alpha chain. In some aspects, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some aspects, the anti-MUC5AC TCR comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some aspects, the anti-MUC5AC TCR comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti- MUC5AC TCR comprises a beta chain constant region present in the beta chain amino acid sequence set forth in SEQ ID NO: 2. In some aspects, the anti-MUC5AC TCR encoded by the first nucleotide further comprises a beta constant region that is different from endogenous, e.g., naturally occurring, constant regions of the beta chain. In some aspects, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain aspects, the anti-MUC5AC TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some aspects, the anti-MUC5AC TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-MUC5AC TCR comprises an alpha chain CDR3 comprising an amino acid sequence as set forth in SEQ ID NO: 7. In some aspects, the anti-MUC5AC TCR comprises an alpha chain comprising the amino acid sequence set forth in SEQ ID NO: 1.

In certain aspects, the anti-MUC5AC TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some aspects, the anti-MUC5AC TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-MUC5AC TCR comprises a beta chain CDR3 comprising an amino acid sequence as set forth in SEQ ID NO: 10. In some aspects, the anti-MUC5AC TCR comprises a beta chain comprising the amino acid sequence set forth in SEQ ID NO: 2.

In some aspects, the anti-MUC5AC TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.B.2. Epitopes

In some aspects, the anti-MUC5AC TCR binds the same epitope as a reference TCR. In some aspects, the anti-MUC5AC TCR binds to an epitope of MUC5AC comprising the amino acid sequence set forth in SEQ ID NO: 13. In some aspects, the anti-MUC5AC TCR binds to an epitope of MUC5AC consisting of an amino acid sequence as set forth in SEQ ID NO: 13. In some aspects, the epitope consists of amino acid residues 4922-4941 of MUC5AC (SEQ ID NO: 16), e.g., "MUC5AC$_{4922\text{-}4941}$."

In certain aspects, the epitope is complexed with an HLA class II molecule. In some aspects, the HLA class II molecule comprises an alpha chain and a beta chain. In some aspects, the alpha chain is selected from an HLA-DR alpha chain, an HLA-DP alpha chain, and an HLA-DQ alpha chain. In some aspects, the beta chain is selected from an HLA-DR beta chain, an HLA-DP beta chain, and an HLA-DQ beta chain. In certain aspects, the HLA class II molecule comprises an HLA-DR alpha chain and an HLA-DR beta chain. In certain aspects, the HLA class II molecule comprises an HLA-DP alpha chain and an HLA-DP beta chain. In certain aspects, the HLA class II molecule comprises an HLA-DQ alpha chain and an HLA-DQ beta chain.

Many HLA-DR, HLA-DP, and HLA-DQ alleles are known in the art, and any of the known alleles can be used in the present disclosure. An updated list of HLA alleles is available at hla.alleles.org/(last visited on Feb. 27, 2019), which is incorporated by reference herein in its entirety.

II.B.3. Bispecific T Cell Receptors (TCRs)

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein. In some aspects, the first antigen-binding domain comprises a single chain variable fragment ("scFv").

In some aspects, the second antigen-binding domain binds specifically to a protein expressed on the surface of a T cell. Any protein expressed on the surface of a T cell can be targeted by the bispecific antibody disclosed herein. In certain aspects, the protein expressed on the surface of a T cell is not expressed by other cells. In some aspects, the protein expressed on the surface of a T cell is expressed on the surface of one or more other human immune cells. In some aspects, the protein expressed on the surface of a T cell is expressed on the surface of one or more other human immune cells, but it is not expressed on the surface of a human non-immune cell. In some aspects, the second antigen-binding domain binds specifically to a protein expressed on the surface of a T cell selected from CD3, CD4, CD2, CD5, CD6, CD8, CD11a (LFA-1α), CD43, CD45, and CD53. In certain aspects, the second antigen-binding domain binds specifically to CD3. In certain aspects, the second antigen-binding domain binds specifically to CD4. In some aspects, the second antigen-binding domain comprises an scFv.

In some aspects, the first antigen-binding domain and the second antigen-binding domain are linked or associated by a covalent bond. In some aspects, the first antigen-binding domain and the second antigen-binding domain are linked by a peptide bond.

II.C. Cells Expressing TCRs

Certain aspects of the present disclosure are directed to cells comprising a nucleic acid molecule disclosed herein, a vector disclosed herein, a recombinant TCR disclosed herein, a bispecific TCR disclosed herein, or any combination thereof. Any cell can be used in the present disclosure.

In certain aspects, the cell expresses CD4. CD4 expression can be naturally occurring, e.g., the CD4 is expressed from a nucleic acid sequence that is endogenously expressed by the cell. For example, T cells, monocytes, macrophages, dendritic cells, and natural killer (NK) cells naturally express CD4. Thus, in some aspects, the cell is a T cell, a monocyte, a macrophage, a dendritic cell, or a natural killer cell. In certain aspects, the cell is a T cell selected from a natural killer T (NKT) cell and an innate lymphoid cell (ILC). In some aspects, the cell is a monocyte. In some aspects, the cell is a macrophage. In some aspects, the cell is a dendritic cell.

In some aspects, the T cell is isolated from a human subject. In some aspects, the human subject is the same subject that will ultimately receive the T cell therapy. In other aspects, the subject is a donor subject, wherein the donor subject is not the same subject that will receive the T cell therapy.

In some aspects, the cell is a cell that does not naturally express CD4, wherein the cell has been modified to express CD4. In some aspects, the cell comprises a transgene encoding CD4, wherein the transgene is expressed by the cell. In some aspects, the cell comprises a transgene encoding a protein that activates expression of endogenous CD4 by the cell. In some aspects, the cell comprises a transgene encoding a protein or siRNA that inhibits an inhibitor of CD4 expression in the cell. In some aspects, the transgene is incorporated into the genome of the cell. In some aspects, the transgene is not incorporated into the genome of the cell.

In some aspects, the cell that is modified to express CD4 is isolated from a human subject. In some aspects, the human subject is the same subject that will ultimately receive the cell therapy. In other aspects, the subject is a donor subject, wherein the donor subject is not the same subject that will receive the cell therapy.

II.D. HLA Class II Molecules

Certain aspects of the present disclosure are directed to a HLA class II molecule complexed to a peptide, wherein the peptide comprises the amino acid sequence set forth in SEQ ID NO: 13. In some aspects, the peptide consists of the amino acid sequence set forth in SEQ ID NO: 13.

In some aspects, the HLA Class II molecule is an HLA-DR, HLA-DP, or an HLA-DQ allele. In some aspects, the HLA class II molecule is any HLA allele disclosed at hla.alleles.org/(last visited on Feb. 27, 2019)

In some aspects, the HLA Class II molecule comprises an alpha chain and a beta chain. In some aspects, the sequence of the alpha chain is selected from any of the HLA alpha chain protein sequences available at hla.alleles.org (last visited Feb. 27, 2019).

II.D.1. HLA-DP Class II Molecules

In some aspects, the alpha chain is an HLA-DP alpha chain. Any HLA-DP alpha chain allele known in the art can be used in the compositions and methods disclosed herein. In some aspects, the alpha chain is selected from an HLA-DPA1*01, HLA-DPA1*02, HLA-DPA1*03, and HLA-DPA1*04 allele. In certain aspects, the DP alpha chain comprises an HLA-DPA1*01 allele. In certain aspects, the DP alpha chain comprises an HLA-DPA1*02 allele. In certain aspects, the DP alpha chain comprises an HLA-DPA1*03 allele. In certain aspects, the DP alpha chain comprises an HLA-DPA1*04 allele.

In certain aspects, the DP alpha chain is selected from DPA1*01:03:01:01, DPA1*01:03:01:02, DPA1*01:03:01:03, DPA1*01:03:01:04, DPA1*01:03:01:05, DPA1*01:03:01:06, DPA1*01:03:01:07, DPA1*01:03:01:08, DPA1*01:03:01:09, DPA1*01:03:01:10, DPA1*01:03:01:11, DPA1*01:03:01:12, DPA1*01:03:01:13, DPA1*01:03:01:14, DPA1*01:03:01:15, DPA1*01:03:01:16, DPA1*01:03:01:17, DPA1*01:03:01:18Q, DPA1*01:03:01:19, DPA1*01:03:01:20, DPA1*01:03:01:21, DPA1*01:03:01:22, DPA1*01:03:01:23, DPA1*01:03:02, DPA1*01:03:03, DPA1*01:03:04, DPA1*01:03:05, DPA1*01:03:06, DPA1*01:03:07, DPA1*01:03:08, DPA1*01:03:09, DPA1*01:04, DPA1*01:05, DPA1*01:06:01, DPA1*01:06:02, DPA1*01:07, DPA1*01:08, DPA1*01:09, DPA1*01:10, DPA1*01:11, DPA1*01:12, DPA1*01:13, DPA1*01:14, DPA1*01:15, DPA1*01:16, DPA1*01:17, DPA1*01:18, DPA1*01:19, DPA1*02:01:01:01, DPA1*02:01:01:02, DPA1*02:01:01:03, DPA1*02:01:01:04, DPA1*02:01:01:05, DPA1*02:01:01:06, DPA1*02:01:01:07, DPA1*02:01:01:08, DPA1*02:01:01:09, DPA1*02:01:01:10, DPA1*02:01:01:11, DPA1*02:01:02:01, DPA1*02:01:02:02, DPA1*02:01:03, DPA1*02:01:04, DPA1*02:01:05, DPA1*02:01:06, DPA1*02:01:07, DPA1*02:01:08:01, DPA1*02:01:08:02, DPA1*02:02:02:01, DPA1*02:02:02:02, DPA1*02:02:02:03, DPA1*02:02:02:04, DPA1*02:02:02:05, DPA1*02:02:03, DPA1*02:02:04, DPA1*02:02:05, DPA1*02:02:06, DPA1*02:03, DPA1*02:04, DPA1*02:05, DPA1*02:06, DPA1*02:07:01:01, DPA1*02:07:01:02, DPA1*02:07:01:03, DPA1*02:08, DPA1*02:09, DPA1*02:10, DPA1*02:11, DPA1*02:12, DPA1*02:13N, DPA1*02:14, DPA1*02:15, DPA1*02:16, DPA1*03:01:01:01, DPA1*03:01:01:02, DPA1*03:01:01:03, DPA1*03:01:01:04, DPA1*03:01:01:05, DPA1*03:01:02, DPA1*03:02, DPA1*03:03, DPA1*03:04, DPA1*04:01:01:01, DPA1*04:01:01:02, DPA1*04:01:01:03, DPA1*04:02, or any combination thereof.

In some aspects, the beta chain is an HLA-DP beta chain. Any HLA-DP beta chain allele known in the art can be used in the compositions and methods disclosed herein. In certain aspects, the DP beta chain comprises an allele selected from an DPB1*01, DPB1*02, DPB1*03, DPB1*04, DPB1*05, DPB1*06, DPB1*08, DPB1*09, DPB1*10, DPB1*100, DPB1*101, DPB1*102, DPB1*103, DPB1*104, DPB1*105, DPB1*106, DPB1*107, DPB1*108, DPB1*109, DPB1*11, DPB1*110, DPB1*111, DPB1*112, DPB1*113, DPB1*114, DPB1*115, DPB1*116, DPB1*117, DPB1*118, DPB1*119, DPB1*120, DPB1*121, DPB1*122, DPB1*123, DPB1*124, DPB1*125, DPB1*126, DPB1*127, DPB1*128, DPB1*129, DPB1*13, DPB1*130, DPB1*131, DPB1*132, DPB1*133, DPB1*134, DPB1*135, DPB1*136, DPB1*137, DPB1*138, DPB1*139, DPB1*14, DPB1*140, DPB1*141, DPB1*142, DPB1*143, DPB1*144, DPB1*145, DPB1*146, DPB1*147, DPB1*148, DPB1*149, DPB1*15, DPB1*150, DPB1*151, DPB1*152, DPB1*153, DPB1*154, DPB1*155, DPB1*156, DPB1*157, DPB1*158, DPB1*159, DPB1*16, DPB1*160, DPB1*161, DPB1*162, DPB1*163, DPB1*164, DPB1*165, DPB1*166, DPB1*167, DPB1*168, DPB1*169, DPB1*17, DPB1*170, DPB1*171, DPB1*172, DPB1*173, DPB1*174, DPB1*175, DPB1*176, DPB1*177, DPB1*178, DPB1*179, DPB1*18, DPB1*180, DPB1*181, DPB1*182, DPB1*183, DPB1*184, DPB1*185, DPB1*186, DPB1*187, DPB1*188, DPB1*189, DPB1*19, DPB1*190, DPB1*191, DPB1*192, DPB1*193, DPB1*194, DPB1*195, DPB1*196, DPB1*197, DPB1*198, DPB1*199, DPB1*20, DPB1*200, DPB1*201, DPB1*202, DPB1*203, DPB1*204, DPB1*205, DPB1*206, DPB1*207, DPB1*208, DPB1*209, DPB1*21, DPB1*210, DPB1*211, DPB1*212, DPB1*213, DPB1*214, DPB1*215, DPB1*216, DPB1*217, DPB1*218, DPB1*219, DPB1*22, DPB1*220, DPB1*221, DPB1*222, DPB1*223, DPB1*224, DPB1*225, DPB1*226, DPB1*227, DPB1*228, DPB1*229, DPB1*23, DPB1*230, DPB1*231, DPB1*232, DPB1*233, DPB1*234, DPB1*235, DPB1*236, DPB1*237, DPB1*238, DPB1*239, DPB1*24, DPB1*240, DPB1*241, DPB1*242, DPB1*243, DPB1*244, DPB1*245, DPB1*246, DPB1*247, DPB1*248, DPB1*249, DPB1*25, DPB1*250, DPB1*251, DPB1*252, DPB1*253, DPB1*254, DPB1*255, DPB1*256, DPB1*257, DPB1*258, DPB1*259, DPB1*26, DPB1*260, DPB1*261, DPB1*262, DPB1*263, DPB1*264, DPB1*265, DPB1*266, DPB1*267, DPB1*268, DPB1*269, DPB1*27, DPB1*270, DPB1*271, DPB1*272, DPB1*273, DPB1*274, DPB1*275, DPB1*276, DPB1*277, DPB1*278, DPB1*279, DPB1*28, DPB1*280, DPB1*281, DPB1*282, DPB1*283, DPB1*284, DPB1*285, DPB1*286, DPB1*287, DPB1*288, DPB1*289, DPB1*29, DPB1*290, DPB1*291, DPB1*292, DPB1*293, DPB1*294, DPB1*295, DPB1*296, DPB1*297, DPB1*298, DPB1*299, DPB1*30, DPB1*300, DPB1*301, DPB1*302, DPB1*303, DPB1*304, DPB1*305, DPB1*306, DPB1*307, DPB1*308, DPB1*309, DPB1*31, DPB1*310, DPB1*311, DPB1*312, DPB1*313, DPB1*314, DPB1*315, DPB1*316, DPB1*317, DPB1*318, DPB1*319, DPB1*32, DPB1*320, DPB1*321, DPB1*322, DPB1*323, DPB1*324, DPB1*325, DPB1*326, DPB1*327, DPB1*328, DPB1*329, DPB1*33, DPB1*330, DPB1*331, DPB1*332, DPB1*333, DPB1*334, DPB1*335, DPB1*336, DPB1*337, DPB1*338, DPB1*339, DPB1*34, DPB1*340, DPB1*341, DPB1*342, DPB1*343, DPB1*344, DPB1*345, DPB1*346, DPB1*347, DPB1*348, DPB1*349, DPB1*35, DPB1*350, DPB1*351, DPB1*352, DPB1*353, DPB1*354, DPB1*355, DPB1*356, DPB1*357, DPB1*358, DPB1*359, DPB1*36, DPB1*360, DPB1*361, DPB1*362, DPB1*363, DPB1*364, DPB1*365, DPB1*366, DPB1*367, DPB1*368, DPB1*369, DPB1*37, DPB1*370, DPB1*371, DPB1*372, DPB1*373, DPB1*374, DPB1*375, DPB1*376, DPB1*377, DPB1*378, DPB1*379, DPB1*38, DPB1*380, DPB1*381, DPB1*382, DPB1*383, DPB1*384, DPB1*385, DPB1*386, DPB1*387, DPB1*388, DPB1*389, DPB1*39, DPB1*390, DPB1*391, DPB1*392, DPB1*393, DPB1*394, DPB1*395, DPB1*396, DPB1*397, DPB1*398, DPB1*399, DPB1*40, DPB1*400, DPB1*401, DPB1*402, DPB1*403, DPB1*404, DPB1*405, DPB1*406, DPB1*407, DPB1*408, DPB1*409, DPB1*41, DPB1*410, DPB1*411, DPB1*412, DPB1*413, DPB1*414, DPB1*415, DPB1*416, DPB1*417, DPB1*418, DPB1*419, DPB1*420, DPB1*421, DPB1*422, DPB1*423, DPB1*424, DPB1*425, DPB1*426, DPB1*427, DPB1*428, DPB1*429, DPB1*430, DPB1*431, DPB1*432, DPB1*433, DPB1*434, DPB1*435, DPB1*436, DPB1*437, DPB1*438, DPB1*439, DPB1*44, DPB1*440, DPB1*441, DPB1*442, DPB1*443, DPB1*444, DPB1*445, DPB1*446, DPB1*447, DPB1*448, DPB1*449, DPB1*45, DPB1*450, DPB1*451, DPB1*452, DPB1*453, DPB1*454, DPB1*455, DPB1*456, DPB1*457, DPB1*458, DPB1*459, DPB1*46, DPB1*460, DPB1*461, DPB1*462, DPB1*463, DPB1*464, DPB1*465, DPB1*466, DPB1*467, DPB1*468, DPB1*469, DPB1*47, DPB1*470, DPB1*471, DPB1*472, DPB1*473, DPB1*474, DPB1*475, DPB1*476, DPB1*477, DPB1*478, DPB1*479, DPB1*48, DPB1*480, DPB1*481, DPB1*482, DPB1*483, DPB1*484, DPB1*485, DPB1*486, DPB1*487, DPB1*488, DPB1*489, DPB1*49, DPB1*490, DPB1*491, DPB1*492, DPB1*493, DPB1*494, DPB1*495, DPB1*496, DPB1*497, DPB1*498, DPB1*499, DPB1*50, DPB1*500, DPB1*501, DPB1*502, DPB1*503, DPB1*504, DPB1*505, DPB1*506, DPB1*507, DPB1*508, DPB1*509, DPB1*51, DPB1*510, DPB1*511, DPB1*512, DPB1*513, DPB1*514, DPB1*515, DPB1*516, DPB1*517, DPB1*518, DPB1*519, DPB1*52, DPB1*520, DPB1*521, DPB1*522, DPB1*523, DPB1*524, DPB1*525, DPB1*526, DPB1*527, DPB1*528, DPB1*529, DPB1*53, DPB1*530, DPB1*531, DPB1*532, DPB1*533, DPB1*534, DPB1*535, DPB1*536, DPB1*537, DPB1*538, DPB1*539, DPB1*54, DPB1*540, DPB1*541, DPB1*542, DPB1*543, DPB1*544, DPB1*545, DPB1*546, DPB1*547, DPB1*548, DPB1*549, DPB1*55, DPB1*550, DPB1*551, DPB1*552, DPB1*553, DPB1*554, DPB1*555, DPB1*556, DPB1*557, DPB1*558, DPB1*559, DPB1*56, DPB1*560, DPB1*561, DPB1*562, DPB1*563, DPB1*564, DPB1*565, DPB1*566, DPB1*567, DPB1*568, DPB1*569, DPB1*57, DPB1*570, DPB1*571, DPB1*572, DPB1*573, DPB1*574, DPB1*575, DPB1*576, DPB1*577, DPB1*578, DPB1*579, DPB1*58, DPB1*580, DPB1*581, DPB1*582, DPB1*583, DPB1*584, DPB1*585, DPB1*586, DPB1*587, DPB1*588, DPB1*589, DPB1*59, DPB1*590, DPB1*591, DPB1*592, DPB1*593, DPB1*594, DPB1*595, DPB1*596, DPB1*597, DPB1*598, DPB1*599, DPB1*60, DPB1*600, DPB1*601, DPB1*602, DPB1*603, DPB1*604, DPB1*605, DPB1*606, DPB1*607, DPB1*608, DPB1*609, DPB1*61, DPB1*610, DPB1*611, DPB1*612, DPB1*613, DPB1*614, DPB1*615, DPB1*616, DPB1*617, DPB1*618, DPB1*619, DPB1*62, DPB1*620, DPB1*621, DPB1*622, DPB1*623, DPB1*624, DPB1*625, DPB1*626, DPB1*627, DPB1*628, DPB1*629, DPB1*63, DPB1*630, DPB1*631, DPB1*632, DPB1*633, DPB1*634, DPB1*635, DPB1*636, DPB1*637, DPB1*638, DPB1*639, DPB1*64, DPB1*640, DPB1*641, DPB1*642, DPB1*643, DPB1*644, DPB1*645, DPB1*646, DPB1*647, DPB1*648, DPB1*649, DPB1*65, DPB1*650, DPB1*651, DPB1*652, DPB1*653, DPB1*654, DPB1*655, DPB1*656, DPB1*657, DPB1*658, DPB1*659, DPB1*66, DPB1*660, DPB1*661, DPB1*662, DPB1*663, DPB1*664, DPB1*665, DPB1*666, DPB1*667, DPB1*668, DPB1*669, DPB1*67, DPB1*670, DPB1*671, DPB1*672, DPB1*673, DPB1*674, DPB1*675, DPB1*676, DPB1*677, DPB1*678, DPB1*679, DPB1*68, DPB1*680, DPB1*681, DPB1*682, DPB1*683, DPB1*684, DPB1*685, DPB1*686, DPB1*687, DPB1*688, DPB1*689, DPB1*69, DPB1*690, DPB1*691, DPB1*692, DPB1*693, DPB1*694, DPB1*695, DPB1*696, DPB1*697, DPB1*698, DPB1*699, DPB1*70, DPB1*700, DPB1*701, DPB1*702, DPB1*703, DPB1*704, DPB1*705, DPB1*706, DPB1*707, DPB1*708, DPB1*709, DPB1*71, DPB1*710, DPB1*711, DPB1*712, DPB1*713, DPB1*714, DPB1*715, DPB1*716, DPB1*717, DPB1*718, DPB1*719, DPB1*72, DPB1*720, DPB1*721, DPB1*722, DPB1*723, DPB1*724, DPB1*725, DPB1*726, DPB1*727, DPB1*728, DPB1*729, DPB1*73, DPB1*730, DPB1*731, DPB1*732, DPB1*733, DPB1*734, DPB1*735, DPB1*736, DPB1*737, DPB1*738, DPB1*739, DPB1*74, DPB1*740, DPB1*741, DPB1*742, DPB1*743, DPB1*744, DPB1*745, DPB1*746, DPB1*747, DPB1*748, DPB1*749, DPB1*75, DPB1*750, DPB1*751, DPB1*752, DPB1*753, DPB1*754, DPB1*755, DPB1*756, DPB1*757, DPB1*758, DPB1*759, DPB1*76, DPB1*760, DPB1*761, DPB1*762, DPB1*763, DPB1*764, DPB1*765, DPB1*766, DPB1*767, DPB1*768, DPB1*769, DPB1*77, DPB1*770, DPB1*771, DPB1*772, DPB1*773, DPB1*774, DPB1*775, DPB1*776, DPB1*777, DPB1*778, DPB1*779, DPB1*78, DPB1*780, DPB1*781, DPB1*782, DPB1*783, DPB1*784, DPB1*785, DPB1*786, DPB1*787, DPB1*788, DPB1*789, DPB1*79, DPB1*790, DPB1*791, DPB1*792, DPB1*794, DPB1*795, DPB1*796, DPB1*797, DPB1*798, DPB1*799, DPB1*80, DPB1*800, DPB1*801, DPB1*802, DPB1*803, DPB1*804, DPB1*805, DPB1*806, DPB1*807, DPB1*808, DPB1*809, DPB1*81, DPB1*810, DPB1*811, DPB1*812, DPB1*813, DPB1*814, DPB1*815, DPB1*816, DPB1*817, DPB1*818, DPB1*819, DPB1*82, DPB1*820, DPB1*821, DPB1*822, DPB1*823, DPB1*824, DPB1*825, DPB1*826, DPB1*827, DPB1*828, DPB1*829, DPB1*83, DPB1*830, DPB1*831, DPB1*832, DPB1*833, DPB1*834, DPB1*835, DPB1*836, DPB1*837, DPB1*838, DPB1*839, DPB1*84, DPB1*840, DPB1*841, DPB1*842, DPB1*843, DPB1*844, DPB1*845, DPB1*846, DPB1*847, DPB1*848, DPB1*849, DPB1*85, DPB1*850, DPB1*851, DPB1*852, DPB1*853, DPB1*854, DPB1*855, DPB1*856, DPB1*857, DPB1*858, DPB1*859, DPB1*86, DPB1*860, DPB1*861, DPB1*862, DPB1*863, DPB1*864, DPB1*865, DPB1*866, DPB1*867, DPB1*868, DPB1*869, DPB1*87, DPB1*870, DPB1*871, DPB1*872, DPB1*873, DPB1*874, DPB1*875, DPB1*876, DPB1*877, DPB1*878, DPB1*879, DPB1*88, DPB1*880, DPB1*881, DPB1*882, DPB1*883, DPB1*884, DPB1*885, DPB1*886, DPB1*887, DPB1*888, DPB1*889, DPB1*89, DPB1*890, DPB1*891, DPB1*892, DPB1*893, DPB1*894, DPB1*895, DPB1*896, DPB1*897, DPB1*898, DPB1*899, DPB1*90, DPB1*900, DPB1*901, DPB1*902, DPB1*903, DPB1*904, DPB1*905, DPB1*906, DPB1*907, DPB1*908, DPB1*909, DPB1*91, DPB1*910, DPB1*911, DPB1*912, DPB1*913, DPB1*914, DPB1*915, DPB1*916, DPB1*917, DPB1*918, DPB1*919, DPB1*92, DPB1*920, DPB1*921, DPB1*922, DPB1*923, DPB1*924, DPB1*925, DPB1*926, DPB1*927, DPB1*928, DPB1*929, DPB1*93, DPB1*930, DPB1*931, DPB1*932, DPB1*933, DPB1*934, DPB1*935, DPB1*936, DPB1*937, DPB1*938, DPB1*939, DPB1*94, DPB1*940, DPB1*941, DPB1*942, DPB1*943, DPB1*944, DPB1*945, DPB1*946, DPB1*947, DPB1*948, DPB1*949, DPB1*95, DPB1*950, DPB1*951, DPB1*952, DPB1*953, DPB1*954, DPB1*955, DPB1*956, DPB1*957, DPB1*958, DPB1*959, DPB1*96, DPB1*960, DPB1*961, DPB1*962, DPB1*963, DPB1*964, DPB1*965, DPB1*97, DPB1*98, and DPB1*99. In some aspects, the DP beta chain comprises an HLA-DPB1*01, HLA-DPB1*02, HLA-DPB1*01, HLA-DPB1*03, HLA-DPB1*04, HLA-DPB1*05, HLA-DPB1*06, HLA-DPB1*08, HLA-DPB1*09 allele, and any combination thereof. In certain aspects, the DP beta chain comprises an HLA-DPB1*04 allele. In particular aspects, the DP beta chain comprises an HLA-DPB1*04:01 allele.

In some aspects, the DP beta chain comprises an allele selected from DPB1*01:01:01:01, DPB1*01:01:01:02, DPB1*01:01:01:03, DPB1*01:01:01:04, DPB1*01:01:01: 05, DPB1*01:01:01:06, DPB1*01:01:01:07, DPB1*01:01: 01:08, DPB1*01:01:01:09, DPB1*01:01:01:10, DPB1*01: 01:02:01, DPB1*01:01:02:02, DPB1*01:01:03, DPB1*01: 01:04, DPB1*01:01:05, DPB1*01:01:06, DPB1*02:01:02: 01, DPB1*02:01:02:02, DPB1*02:01:02:03, DPB1*02:01: 02:04, DPB1*02:01:02:05, DPB1*02:01:02:06, DPB1*02: 01:02:07, DPB1*02:01:02:08, DPB1*02:01:02:09, DPB1*02:01:02:10, DPB1*02:01:02:11, DPB1*02:01:02: 12, DPB1*02:01:02:13, DPB1*02:01:02:14, DPB1*02:01:

02:15, DPB1*02:01:02:16, DPB1*02:01:02:17, DPB1*02:01:02:18, DPB1*02:01:02:19, DPB1*02:01:02:20, DPB1*02:01:02:21, DPB1*02:01:02:22, DPB1*02:01:02:23, DPB1*02:01:02:24, DPB1*02:01:02:25, DPB1*02:01:02:26, DPB1*02:01:02:27, DPB1*02:01:02:28, DPB1*02:01:02:29, DPB1*02:01:02:30, DPB1*02:01:02:31, DPB1*02:01:02:32, DPB1*02:01:02:33, DPB1*02:01:02:34, DPB1*02:01:02:35, DPB1*02:01:02:36, DPB1*02:01:02:37, DPB1*02:01:02:38, DPB1*02:01:02:39, DPB1*02:01:02:40, DPB1*02:01:02:41, DPB1*02:01:02:42, DPB1*02:01:02:43, DPB1*02:01:03, DPB1*02:01:04, DPB1*02:01:05, DPB1*02:01:06, DPB1*02:01:07, DPB1*02:01:08, DPB1*02:01:09, DPB1*02:01:10, DPB1*02:01:11, DPB1*02:01:12, DPB1*02:01:13, DPB1*02:01:14, DPB1*02:01:15, DPB1*02:01:16, DPB1*02:01:17, DPB1*02:01:18, DPB1*02:01:19, DPB1*02:01:20, DPB1*02:01:21, DPB1*02:01:22, DPB1*02:01:23, DPB1*02:01:24, DPB1*02:01:25, DPB1*02:01:26, DPB1*02:01:27, DPB1*02:01:28, DPB1*02:01:29, DPB1*02:01:30, DPB1*02:01:31, DPB1*02:01:32, DPB1*02:01:33, DPB1*02:01:34, DPB1*02:01:35, DPB1*02:01:36, DPB1*02:01:37, DPB1*02:01:38, DPB1*02:01:39, DPB1*02:01:40, DPB1*02:01:41, DPB1*02:01:42, DPB1*02:01:43, DPB1*02:02:01:01, DPB1*02:02:01:02, DPB1*02:02:01:03, DPB1*02:02:01:04, DPB1*02:02:01:05, DPB1*02:02:01:06, DPB1*02:02:01:07, DPB1*02:02:02, DPB1*02:02:03, DPB1*03:01:01:01, DPB1*03:01:01:02, DPB1*03:01:01:03, DPB1*03:01:01:04, DPB1*03:01:01:05, DPB1*03:01:01:06, DPB1*03:01:01:07, DPB1*03:01:01:08, DPB1*03:01:01:09, DPB1*03:01:01:10, DPB1*03:01:01:11, DPB1*03:01:02, DPB1*03:01:03, DPB1*03:01:04, DPB1*03:01:05, DPB1*03:01:06, DPB1*03:01:07, DPB1*03:01:08, DPB1*03:01:09, DPB1*03:01:10, DPB1*03:01:11, DPB1*03:01:12, DPB1*04:01:01:01, DPB1*04:01:01:02, DPB1*04:01:01:03, DPB1*04:01:01:04, DPB1*04:01:01:05, DPB1*04:01:01:06, DPB1*04:01:01:07, DPB1*04:01:01:08, DPB1*04:01:01:09, DPB1*04:01:01:10, DPB1*04:01:01:11, DPB1*04:01:01:12, DPB1*04:01:01:13, DPB1*04:01:01:14, DPB1*04:01:01:15, DPB1*04:01:01:16, DPB1*04:01:01:17, DPB1*04:01:01:18, DPB1*04:01:01:19, DPB1*04:01:01:20, DPB1*04:01:01:21, DPB1*04:01:01:22, DPB1*04:01:01:23, DPB1*04:01:01:24N, DPB1*04:01:01:25, DPB1*04:01:01:26, DPB1*04:01:01:27, DPB1*04:01:01:28, DPB1*04:01:01:29, DPB1*04:01:01:30, DPB1*04:01:01:31, DPB1*04:01:01:32, DPB1*04:01:01:33, DPB1*04:01:01:34, DPB1*04:01:02, DPB1*04:01:03, DPB1*04:01:04:01, DPB1*04:01:04:02, DPB1*04:01:05, DPB1*04:01:06, DPB1*04:01:07, DPB1*04:01:08, DPB1*04:01:09, DPB1*04:01:10, DPB1*04:01:11, DPB1*04:01:12, DPB1*04:01:13, DPB1*04:01:14, DPB1*04:01:15, DPB1*04:01:16, DPB1*04:01:17, DPB1*04:01:18, DPB1*04:01:19, DPB1*04:01:20, DPB1*04:01:21, DPB1*04:01:22, DPB1*04:01:23, DPB1*04:01:24, DPB1*04:01:25, DPB1*04:01:26, DPB1*04:01:27, DPB1*04:01:28, DPB1*04:01:29, DPB1*04:01:30, DPB1*04:01:31, DPB1*04:01:32, DPB1*04:01:33, DPB1*04:01:34, DPB1*04:01:35, DPB1*04:01:36, DPB1*04:01:37, DPB1*04:01:38, DPB1*04:01:39, DPB1*04:01:40, DPB1*04:02:01:01, DPB1*04:02:01:02, DPB1*04:02:01:03, DPB1*04:02:01:04, DPB1*04:02:01:05, DPB1*04:02:01:06, DPB1*04:02:01:07, DPB1*04:02:01:08, DPB1*04:02:01:09, DPB1*04:02:01:10, DPB1*04:02:01:11, DPB1*04:02:01:12, DPB1*04:02:01:13, DPB1*04:02:01:14, DPB1*04:02:02, DPB1*04:02:03, DPB1*04:02:04, DPB1*04:02:05, DPB1*04:02:06,

DPB1*04:02:07, DPB1*04:02:08, DPB1*04:02:09, DPB1*04:02:10, DPB1*04:02:11, DPB1*04:02:12, DPB1*04:02:13, DPB1*04:02:14, DPB1*05:01:01:01, DPB1*05:01:01:02, DPB1*05:01:01:03, DPB1*05:01:01:04, DPB1*05:01:01:05, DPB1*05:01:01:06, DPB1*05:01:01:07, DPB1*05:01:01:08, DPB1*05:01:01:09, DPB1*05:01:01:10, DPB1*05:01:02, DPB1*05:01:03, DPB1*05:01:04, DPB1*05:01:05, DPB1*05:01:06, DPB1*05:01:07, DPB1*05:01:08, DPB1*05:01:09, DPB1*06:01:01:01, DPB1*06:01:01:02, DPB1*06:01:01:03, DPB1*06:01:02, DPB1*06:01:03, DPB1*06:01:04, DPB1*06:01:05, DPB1*08:01, DPB1*09:01:01, DPB1*09:01:02, DPB1*09:01:03, DPB1*09:01:04, DPB1*100:01, DPB1*101:01, DPB1*102:01, DPB1*103:01, DPB1*104:01:01:01, DPB1*104:01:01:02, DPB1*104:01:01:03, DPB1*104:01:01:04, DPB1*104:01:01:05, DPB1*104:01:01:06, DPB1*104:01:02, DPB1*105:01:01:01, DPB1*105:01:01:02, DPB1*105:01:01:03, DPB1*105:01:01:04, DPB1*105:01:01:05, DPB1*105:01:01:06, DPB1*105:01:01:07, DPB1*105:01:01:08, DPB1*105:01:01:09, DPB1*105:01:01:10, DPB1*106:01, DPB1*107:01, DPB1*108:01, DPB1*109:01, DPB1*10:01:01:01, DPB1*10:01:01:02, DPB1*10:01:02, DPB1*10:01:03, DPB1*10:01:04, DPB1*110:01, DPB1*111:01, DPB1*112:01, DPB1*113:01, DPB1*114:01, DPB1*115:01, DPB1*116:01, DPB1*117:01, DPB1*118:01, DPB1*119:01, DPB1*11:01:01:01, DPB1*11:01:01:02, DPB1*11:01:02, DPB1*11:01:03, DPB1*11:01:04, DPB1*120:01N, DPB1*121:01, DPB1*122:01, DPB1*123:01, DPB1*124:01:01:01, DPB1*124:01:01:02, DPB1*124:01:02:01, DPB1*124:01:02:02, DPB1*125:01, DPB1*126:01:01:01, DPB1*126:01:01:02, DPB1*127:01, DPB1*128:01, DPB1*129:01, DPB1*130:01, DPB1*131:01:01:01, DPB1*131:01:01:02, DPB1*131:01:02, DPB1*131:01:03, DPB1*132:01, DPB1*133:01, DPB1*134:01, DPB1*135:01, DPB1*136:01, DPB1*137:01, DPB1*138:01, DPB1*139:01, DPB1*13:01:01:01, DPB1*13:01:01:02, DPB1*13:01:01:03, DPB1*13:01:01:04, DPB1*13:01:01:05, DPB1*13:01:01:06, DPB1*13:01:01:07, DPB1*13:01:01:08, DPB1*13:01:02, DPB1*13:01:03, DPB1*140:01, DPB1*141:01, DPB1*142:01, DPB1*143:01, DPB1*144:01, DPB1*145:01, DPB1*146:01, DPB1*147:01, DPB1*148:01, DPB1*149:01, DPB1*14:01:01:01, DPB1*14:01:01:02, DPB1*14:01:01:03, DPB1*14:01:02, DPB1*14:01:03, DPB1*14:01:04, DPB1*14:01:05, DPB1*14:01:06, DPB1*14:01:07, DPB1*14:01:08, DPB1*14:01:09, DPB1*150:01, DPB1*151:01, DPB1*152:01, DPB1*153:01, DPB1*154:01N, DPB1*155:01:01, DPB1*155:01:02, DPB1*156:01, DPB1*157:01, DPB1*158:01, DPB1*159:01N, DPB1*15:01:01:01, DPB1*15:01:01:02, DPB1*15:01:01:03, DPB1*15:01:01:04, DPB1*15:01:02, DPB1*15:01:03, DPB1*160:01, DPB1*161:01N, DPB1*162:01:01, DPB1*162:01:02, DPB1*163:01, DPB1*164:01, DPB1*165:01, DPB1*166:01, DPB1*167:01, DPB1*168:01, DPB1*169:01, DPB1*16:01:01:01, DPB1*16:01:01:02, DPB1*16:01:02, DPB1*16:01:03, DPB1*170:01, DPB1*171:01, DPB1*172:01, DPB1*173:01, DPB1*174:01, DPB1*175:01, DPB1*176:01, DPB1*177:01, DPB1*178:01, DPB1*179:01, DPB1*17:01:01:01, DPB1*17:01:01:02, DPB1*17:01:02, DPB1*17:01:03, DPB1*180:01, DPB1*181:01, DPB1*182:01, DPB1*183:01, DPB1*184:01, DPB1*185:01, DPB1*186:01, DPB1*187:01, DPB1*188:01, DPB1*189:01, DPB1*18:01:01:01, DPB1*18:01:01:02, DPB1*18:01:01:03, DPB1*18:01:02, DPB1*18:01:03, DPB1*190:01, DPB1*191:01, DPB1*192:01, DPB1*193:01, DPB1*194:01, DPB1*195:01, DPB1*196:01, DPB1*197:01,

DPB1*198:01, DPB1*199:01, DPB1*19:01:01:01, DPB1*19:01:01:02, DPB1*19:01:01:03, DPB1*200:01, DPB1*201:01, DPB1*202:01, DPB1*203:01:01, DPB1*203:01:02, DPB1*204:01, DPB1*205:01, DPB1*206:01, DPB1*207:01, DPB1*208:01, DPB1*209:01, DPB1*20:01:01:01, DPB1*20:01:01:02, DPB1*20:01:02, DPB1*20:01:03, DPB1*20:01:04, DPB1*210:01, DPB1*211:01, DPB1*212:01, DPB1*213:01:01, DPB1*213:01:02, DPB1*214:01, DPB1*215:01, DPB1*216:01N, DPB1*217:01, DPB1*218:01N, DPB1*219:01, DPB1*21:01, DPB1*220:01, DPB1*221:01, DPB1*222:01, DPB1*223:01, DPB1*224:01, DPB1*225:01, DPB1*226:01, DPB1*227:01:01, DPB1*227:01:02, DPB1*228:01, DPB1*229:01, DPB1*22:01:01:01, DPB1*22:01:01:02, DPB1*230:01, DPB1*231:01, DPB1*232:01, DPB1*233:01, DPB1*234:01, DPB1*235:01, DPB1*236:01:01, DPB1*236:01:02, DPB1*237:01, DPB1*238:01, DPB1*239:01, DPB1*23:01:01:01, DPB1*23:01:01:02, DPB1*23:01:02, DPB1*240:01, DPB1*241:01, DPB1*242:01, DPB1*243:01, DPB1*244:01, DPB1*245:01, DPB1*246:01, DPB1*247:01, DPB1*248:01, DPB1*249:01, DPB1*24:01, DPB1*250:01, DPB1*251:01, DPB1*252:01, DPB1*253:01, DPB1*254:01, DPB1*255:01, DPB1*256:01, DPB1*257:01, DPB1*258:01, DPB1*259:01, DPB1*25:01, DPB1*260:01, DPB1*261:01, DPB1*262:01, DPB1*263:01, DPB1*264:01, DPB1*265:01, DPB1*266:01, DPB1*267:01, DPB1*268:01, DPB1*269:01, DPB1*26:01:01, DPB1*26:01:02, DPB1*26:01:03, DPB1*270:01, DPB1*271:01, DPB1*272:01, DPB1*273:01, DPB1*274:01, DPB1*275:01, DPB1*276:01, DPB1*277:01, DPB1*278:01, DPB1*279:01:01, DPB1*279:01:02, DPB1*27:01, DPB1*280:01, DPB1*281:01, DPB1*282:01, DPB1*283:01, DPB1*284:01, DPB1*285:01, DPB1*286:01, DPB1*287:01, DPB1*288:01, DPB1*289:01, DPB1*28:01, DPB1*290:01, DPB1*291:01, DPB1*292:01, DPB1*293:01, DPB1*294:01, DPB1*295:01, DPB1*296:01, DPB1*297:01, DPB1*298:01, DPB1*299:01, DPB1*29:01, DPB1*300:01, DPB1*301:01, DPB1*302:01, DPB1*303:01, DPB1*304:01, DPB1*305:01, DPB1*306:01, DPB1*307:01, DPB1*308:01, DPB1*309:01, DPB1*30:01:01:01, DPB1*30:01:01:02, DPB1*310:01, DPB1*311:01, DPB1*312:01, DPB1*313:01, DPB1*314:01, DPB1*315:01, DPB1*316:01, DPB1*317:01, DPB1*318:01, DPB1*319:01, DPB1*31:01:01:01, DPB1*31:01:01:02, DPB1*320:01, DPB1*321:01, DPB1*322:01, DPB1*323:01, DPB1*324:01, DPB1*325:01, DPB1*326:01, DPB1*327:01, DPB1*328:01N, DPB1*329:01, DPB1*32:01, DPB1*330:01, DPB1*331:01, DPB1*332:01, DPB1*333:01, DPB1*334:01, DPB1*335:01, DPB1*336:01, DPB1*337:01, DPB1*338:01, DPB1*339:01, DPB1*33:01:01:01, DPB1*33:01:01:02, DPB1*33:01:01:03, DPB1*33:01:01:04, DPB1*33:01:01:05, DPB1*340:01, DPB1*341:01, DPB1*342:01, DPB1*343:01, DPB1*344:01, DPB1*345:01, DPB1*346:01, DPB1*347:01, DPB1*348:01:01, DPB1*348:01:02, DPB1*349:01, DPB1*34:01:01:01, DPB1*34:01:01:02, DPB1*34:01:02, DPB1*350:01, DPB1*351:01, DPB1*352:01:01, DPB1*352:01:02, DPB1*353:01, DPB1*354:01:01, DPB1*354:01:02, DPB1*355:01, DPB1*356:01, DPB1*357:01N, DPB1*358:01, DPB1*359:01, DPB1*35:01:01, DPB1*360:01, DPB1*361:01, DPB1*362:01, DPB1*363:01, DPB1*364:01, DPB1*365:01, DPB1*366:01, DPB1*367:01, DPB1*368:01, DPB1*369:01, DPB1*36:01, DPB1*370:01, DPB1*371:01, DPB1*372:01, DPB1*373:01, DPB1*374:01, DPB1*375:01, DPB1*376:01, DPB1*377:01, DPB1*378:01, DPB1*379:01,

DPB1*37:01, DPB1*380:01, DPB1*381:01, DPB1*382:01N, DPB1*383:01, DPB1*384:01, DPB1*385:01, DPB1*386:01, DPB1*387:01, DPB1*388:01, DPB1*389:01, DPB1*38:01, DPB1*390:01, DPB1*391:01, DPB1*392:01, DPB1*393:01, DPB1*394:01, DPB1*395:01, DPB1*396:01, DPB1*397:01, DPB1*398:01, DPB1*399:01, DPB1*39:01:01:01, DPB1*39:01:01:02, DPB1*39:01:01:03, DPB1*39:01:01:04, DPB1*39:01:02, DPB1*39:01:03, DPB1*400:01, DPB1*401:01N, DPB1*402:01, DPB1*403:01N, DPB1*404:01, DPB1*405:01, DPB1*406:01, DPB1*407:01, DPB1*408:01, DPB1*409:01, DPB1*40:01:01:01, DPB1*40:01:01:02, DPB1*40:01:01:03, DPB1*40:01:02, DPB1*410:01, DPB1*411:01, DPB1*412:01, DPB1*413:01, DPB1*414:01:01:01, DPB1*414:01:01:02, DPB1*415:01, DPB1*416:01:01:01, DPB1*416:01:01:02, DPB1*416:01:01:03, DPB1*416:01:02, DPB1*417:01:01, DPB1*417:01:02, DPB1*418:01, DPB1*419:01, DPB1*41:01:01:01, DPB1*41:01:01:02, DPB1*41:01:02, DPB1*420:01, DPB1*421:01, DPB1*422:01, DPB1*423:01:01, DPB1*423:01:02, DPB1*424:01, DPB1*425:01, DPB1*426:01, DPB1*427:01, DPB1*428:01, DPB1*429:01, DPB1*430:01, DPB1*431:01, DPB1*432:01, DPB1*433:01, DPB1*434:01, DPB1*435:01, DPB1*436:01, DPB1*437:01, DPB1*438:01, DPB1*439:01, DPB1*440:01, DPB1*441:01, DPB1*442:01, DPB1*443:01, DPB1*444:01, DPB1*445:01, DPB1*446:01, DPB1*447:01, DPB1*448:01, DPB1*449:01, DPB1*44:01, DPB1*450:01N, DPB1*451:01, DPB1*452:01, DPB1*453:01, DPB1*454:01, DPB1*455:01N, DPB1*456:01, DPB1*457:01, DPB1*458:01, DPB1*459:01, DPB1*45:01, DPB1*460:01, DPB1*461:01, DPB1*462:01, DPB1*463:01:01:01, DPB1*463:01:01:02, DPB1*463:01:01:03, DPB1*464:01, DPB1*465:01, DPB1*466:01, DPB1*467:01, DPB1*468:01, DPB1*469:01, DPB1*46:01:01, DPB1*46:01:02, DPB1*470:01, DPB1*471:01, DPB1*472:01, DPB1*473:01, DPB1*474:01, DPB1*475:01, DPB1*476:01, DPB1*477:01, DPB1*478:01, DPB1*479:01, DPB1*47:01:01:01, DPB1*47:01:01:02, DPB1*47:01:01:03, DPB1*480:01, DPB1*481:01, DPB1*482:01, DPB1*483:01, DPB1*484:01, DPB1*485:01, DPB1*486:01, DPB1*487:01, DPB1*488:01, DPB1*489:01, DPB1*48:01, DPB1*490:01, DPB1*491:01, DPB1*492:01, DPB1*493:01, DPB1*494:01, DPB1*495:01, DPB1*496:01, DPB1*497:01, DPB1*498:01, DPB1*499:01, DPB1*49:01:01:01, DPB1*49:01:01:02, DPB1*49:01:01:03, DPB1*500:01, DPB1*501:01, DPB1*502:01, DPB1*503:01, DPB1*504:01, DPB1*505:01, DPB1*506:01, DPB1*507:01N, DPB1*508:01, DPB1*509:01, DPB1*50:01, DPB1*510:01, DPB1*511:01, DPB1*512:01, DPB1*513:01, DPB1*514:01, DPB1*515:01, DPB1*516:01, DPB1*517:01, DPB1*518:01, DPB1*519:01, DPB1*51:01:01:01, DPB1*51:01:01:02, DPB1*520:01, DPB1*521:01, DPB1*522:01, DPB1*523:01:01, DPB1*523:01:02, DPB1*524:01, DPB1*525:01, DPB1*526:01, DPB1*527:01, DPB1*528:01, DPB1*529:01, DPB1*52:01, DPB1*530:01, DPB1*531:01, DPB1*532:01, DPB1*533:01, DPB1*534:01, DPB1*535:01, DPB1*536:01, DPB1*537:01, DPB1*538:01, DPB1*539:01, DPB1*53:01, DPB1*540:01, DPB1*541:01, DPB1*542:01, DPB1*543:01, DPB1*544:01, DPB1*545:01, DPB1*546:01, DPB1*547:01, DPB1*548:01, DPB1*549:01, DPB1*54:01, DPB1*550:01, DPB1*551:01N, DPB1*552:01, DPB1*553:01, DPB1*554:01, DPB1*555:01, DPB1*556:01, DPB1*557:01, DPB1*558:01, DPB1*559:01, DPB1*55:01:01:01, DPB1*55:01:01:02, DPB1*55:01:01:03, DPB1*55:01:01:04, DPB1*55:01:01:

05, DPB1*55:01:02, DPB1*560:01, DPB1*561:01, DPB1*562:01, DPB1*563:01, DPB1*564:01, DPB1*565: 01, DPB1*566:01, DPB1*567:01, DPB1*568:01, DPB1*569:01, DPB1*56:01, DPB1*570:01N, DPB1*571: 01, DPB1*572:01, DPB1*573:01, DPB1*574:01, DPB1*575:01, DPB1*576:01, DPB1*577:01, DPB1*578: 01, DPB1*579:01, DPB1*57:01, DPB1*580:01, DPB1*581:01, DPB1*582:01, DPB1*583:01, DPB1*584: 01:01:01, DPB1*584:01:01:02, DPB1*584:01:01:03, DPB1*584:01:02:01, DPB1*584:01:02:02, DPB1*585:01: 01:01, DPB1*585:01:01:02, DPB1*586:01, DPB1*587:01, DPB1*588:01, DPB1*589:01, DPB1*58:01, DPB1*590:01, DPB1*591:01, DPB1*592:01, DPB1*593:01, DPB1*594: 01, DPB1*595:01, DPB1*596:01, DPB1*597:01, DPB1*598:01N, DPB1*599:01, DPB1*59:01, DPB1*600: 01, DPB1*601:01, DPB1*602:01, DPB1*603:01, DPB1*604:01, DPB1*605:01, DPB1*606:01, DPB1*607: 01, DPB1*608:01, DPB1*609:01, DPB1*60:01, DPB1*610:01, DPB1*611:01, DPB1*612:01, DPB1*613: 01, DPB1*614:01, DPB1*615:01, DPB1*616:01, DPB1*617:01, DPB1*618:01, DPB1*619:01, DPB1*61: 01N, DPB1*620:01, DPB1*621:01, DPB1*622:01, DPB1*623:01, DPB1*624:01, DPB1*625:01, DPB1*626: 01, DPB1*627:01, DPB1*628:01, DPB1*629:01, DPB1*62:01, DPB1*630:01, DPB1*631:01, DPB1*632:01, DPB1*633:01, DPB1*634:01, DPB1*635:01, DPB1*636: 01, DPB1*637:01, DPB1*638:01, DPB1*639:01, DPB1*63:01, DPB1*640:01, DPB1*641:01, DPB1*642:01, DPB1*643:01, DPB1*644:01, DPB1*645:01, DPB1*646: 01, DPB1*647:01, DPB1*648:01:01:01, DPB1*648:01:01: 02, DPB1*649:01, DPB1*64:01N, DPB1*650:01, DPB1*651:01, DPB1*652:01, DPB1*653:01, DPB1*654: 01, DPB1*655:01, DPB1*656:01, DPB1*657:01N, DPB1*658:01, DPB1*659:01, DPB1*65:01:01, DPB1*65: 01:02, DPB1*660:01, DPB1*661:01N, DPB1*662:01, DPB1*663:01, DPB1*664:01, DPB1*665:01, DPB1*666: 01, DPB1*667:01, DPB1*668:01:01:01, DPB1*668:01:01: 02, DPB1*669:01, DPB1*66:01, DPB1*670:01, DPB1*671:01, DPB1*672:01, DPB1*673:01, DPB1*674: 01, DPB1*675:01, DPB1*676:01, DPB1*677:01, DPB1*678:01, DPB1*679:01, DPB1*67:01, DPB1*680:01, DPB1*681:01, DPB1*682:01, DPB1*683:01, DPB1*684: 01, DPB1*685:01, DPB1*686:01, DPB1*687:01, DPB1*688:01, DPB1*689:01, DPB1*68:01, DPB1*690:01, DPB1*691:01N, DPB1*692:01, DPB1*693:01N, DPB1*694:01, DPB1*695:01, DPB1*696:01N, DPB1*697: 01Q, DPB1*698:01, DPB1*699:01, DPB1*69:01:01:01, DPB1*69:01:01:02, DPB1*700:01N, DPB1*701:01, DPB1*702:01, DPB1*703:01, DPB1*704:01, DPB1*705: 01, DPB1*706:01, DPB1*707:01, DPB1*708:01, DPB1*709:01, DPB1*70:01, DPB1*710:01, DPB1*711:01, DPB1*712:01N, DPB1*713:01, DPB1*714:01, DPB1*715: 01, DPB1*716:01, DPB1*717:01, DPB1*718:01, DPB1*719:01, DPB1*71:01:01, DPB1*71:01:02, DPB1*720:01, DPB1*721:01, DPB1*722:01, DPB1*723: 01, DPB1*724:01N, DPB1*725:01, DPB1*726:01, DPB1*727:01, DPB1*728:01, DPB1*729:01, DPB1*72: 01:01:01, DPB1*72:01:01:02, DPB1*72:01:01:03, DPB1*730:01, DPB1*731:01, DPB1*732:01N, DPB1*733: 01, DPB1*734:01, DPB1*735:01, DPB1*736:01, DPB1*737:01, DPB1*738:01N, DPB1*739:01, DPB1*73: 01, DPB1*740:01, DPB1*741:01, DPB1*742:01, DPB1*743:01N, DPB1*744:01, DPB1*745:01, DPB1*746: 01, DPB1*747:01, DPB1*748:01N, DPB1*749:01, DPB1*74:01, DPB1*750:01, DPB1*751:01, DPB1*752:01, DPB1*753:01, DPB1*754:01N, DPB1*755:01, DPB1*756: 01N, DPB1*757:01, DPB1*758:01, DPB1*759:01,

DPB1*75:01, DPB1*760:01, DPB1*761:01, DPB1*762:01, DPB1*763:01, DPB1*764:01, DPB1*765:01, DPB1*766: 01, DPB1*767:01, DPB1*768:01, DPB1*769:01, DPB1*76:01, DPB1*770:01, DPB1*771:01, DPB1*772:01, DPB1*773:01, DPB1*774:01, DPB1*775:01, DPB1*776: 01, DPB1*777:01N, DPB1*778:01, DPB1*779:01, DPB1*77:01, DPB1*780:01, DPB1*781:01, DPB1*782:01, DPB1*783:01, DPB1*784:01, DPB1*785:01, DPB1*786: 01:01N, DPB1*786:01:02N, DPB1*787:01, DPB1*788:01, DPB1*789:01, DPB1*78:01, DPB1*790:01, DPB1*791:01, DPB1*792:01N, DPB1*794:01N, DPB1*795:01, DPB1*796:01, DPB1*797:01, DPB1*798:01, DPB1*799: 01, DPB1*79:01, DPB1*800:01N, DPB1*801:01, DPB1*802:01, DPB1*803:01, DPB1*804:01, DPB1*805: 01, DPB1*806:01:01:01, DPB1*806:01:01:02, DPB1*807: 01, DPB1*808:01, DPB1*809:01, DPB1*80:01, DPB1*810:01, DPB1*811:01, DPB1*812:01, DPB1*813: 01, DPB1*814:01, DPB1*815:01, DPB1*816:01, DPB1*817:01, DPB1*818:01, DPB1*819:01, DPB1*81: 01:01:01, DPB1*81:01:01:02, DPB1*81:01:02, DPB1*820: 01, DPB1*821:01N, DPB1*822:01, DPB1*823:01, DPB1*824:01, DPB1*825:01, DPB1*826:01, DPB1*827: 01, DPB1*828:01, DPB1*829:01, DPB1*82:01, DPB1*830:01, DPB1*831:01N, DPB1*832:01, DPB1*833: 01, DPB1*834:01, DPB1*835:01, DPB1*836:01, DPB1*837:01, DPB1*838:01N, DPB1*839:01, DPB1*83: 01, DPB1*840:01, DPB1*841:01, DPB1*842:01, DPB1*843:01, DPB1*844:01N, DPB1*845:01, DPB1*846: 01, DPB1*847:01, DPB1*848:01, DPB1*849:01, DPB1*84:01, DPB1*850:01, DPB1*851:01, DPB1*852:01, DPB1*853:01, DPB1*854:01, DPB1*855:01, DPB1*856: 01, DPB1*857:01, DPB1*858:01, DPB1*859:01, DPB1*85:01:01:01, DPB1*85:01:01:02, DPB1*85:01:02, DPB1*860:01, DPB1*861:01, DPB1*862:01N, DPB1*863: 01, DPB1*864:01, DPB1*865:01N, DPB1*866:01N, DPB1*867:01N, DPB1*868:01N, DPB1*869:01N, DPB1*86:01, DPB1*870:01N, DPB1*871:01N, DPB1*872:01N, DPB1*873:01N, DPB1*874:01N, DPB1*875:01N, DPB1*876:01N, DPB1*877:01N, DPB1*878:01N, DPB1*879:01:01:01, DPB1*879:01:01: 02, DPB1*879:01:01:03, DPB1*87:01, DPB1*880:01, DPB1*881:01, DPB1*882:01, DPB1*883:01, DPB1*884: 01, DPB1*885:01, DPB1*886:01, DPB1*887:01, DPB1*888:01, DPB1*889:01, DPB1*88:01, DPB1*890:01, DPB1*891:01, DPB1*892:01, DPB1*893:01, DPB1*894: 01N, DPB1*895:01, DPB1*896:01, DPB1*897:01, DPB1*898:01, DPB1*899:01, DPB1*89:01, DPB1*900:01, DPB1*901:01, DPB1*902:01, DPB1*903:01, DPB1*904: 01, DPB1*905:01, DPB1*906:01, DPB1*907:01, DPB1*908:01, DPB1*909:01, DPB1*90:01:01, DPB1*90: 01:02, DPB1*910:01, DPB1*911:01N, DPB1*912:01, DPB1*913:01, DPB1*914:01, DPB1*915:01, DPB1*916: 01, DPB1*917:01N, DPB1*918:01, DPB1*919:01N, DPB1*91:01:01:01, DPB1*91:01:01:02, DPB1*920:01, DPB1*921:01, DPB1*922:01, DPB1*923:01, DPB1*924: 01, DPB1*925:01N, DPB1*926:01, DPB1*927:01, DPB1*928:01, DPB1*929:01, DPB1*92:01, DPB1*930:01, DPB1*931:01, DPB1*932:01, DPB1*933:01, DPB1*934: 01Q, DPB1*935:01Q, DPB1*936:01Q, DPB1*937:01, DPB1*938:01, DPB1*939:01N, DPB1*93:01, DPB1*940: 01, DPB1*941:01N, DPB1*942:01, DPB1*943:01, DPB1*944:01, DPB1*945:01, DPB1*946:01, DPB1*947: 01, DPB1*948:01, DPB1*949:01, DPB1*94:01, DPB1*950:01N, DPB1*951:01, DPB1*952:01, DPB1*953: 01, DPB1*954:01, DPB1*955:01, DPB1*956:01, DPB1*957:01, DPB1*958:01, DPB1*959:01N, DPB1*95: 01, DPB1*960:01N, DPB1*961:01, DPB1*962:01,

DPB1*963:01, DPB1*964:01, DPB1*965:01:01:01, DPB1*965:01:01:02, DPB1*96:01, DPB1*97:01, DPB1*98:01, DPB1*99:01, and any combination thereof.

II.D.2. HLA-DQ Class II Molecules

In some aspects, the alpha chain is an HLA-DQ alpha chain. Any HLA-DQ alpha chain allele known in the art can be used in the compositions and methods disclosed herein. In some aspects, the alpha chain is selected from an HLA-DQA1*01, HLA-DQA1*02, HLA-DQA1*03, HLA-DQA1*04, HLA-DQA1*05, and HLA-DQA1*06 allele. In some aspects, the alpha chain is an HLA-DQA1 allele selected from *01:01:01:01, *01:01:01:02, *01:01:01:03, *01:01:01:05, *01:01:01:06, *01:01:02, *01:01:03, *01:01:04, *01:01:05, *01:02:01:01, *01:02:01:02, *01:02:01:03, *01:02:01:04, *01:02:01:05, *01:02:01:06, *01:02:01:07, *01:02:01:08, *01:02:01:09, *01:02:01:10, *01:02:01:11, *01:02:01:12, *01:02:02:01, *01:02:02:02, *01:02:02:03, *01:02:02:04, *01:02:03, *01:02:04, *01:03:01:01, *01:03:01:02, *01:03:01:03, *01:03:01:04, *01:03:01:05, *01:03:01:06, *01:03:01:07, *01:03:01:08, *01:03:01:09, *01:04:01:01, *01:04:01:02, *01:04:01:03, *01:04:01:04, *01:04:02, *01:05:01, *01:05:02, *01:06, *01:07Q, *01:08, *01:09, *01:10, *01:11, *01:12, *01:13, *01:14, *01:15N, *01:16N, *01:17, *01:18, *01:19, *01:20, *01:21, *01:22, *01:23, *01:24, *01:25, *01:26, *02:01:01:01, *02:01:01:02, *02:01:02, *02:02N, *02:03, *03:01:01, *03:01:03, *03:02:01:01, *03:02:01:02, *03:03:01:01, *03:03:01:02, *03:03:01:03, *03:03:01:04, *03:03:01:05, *03:03:01:06, *03:03:01:07, *03:03:02, *03:04, *03:05, *03:06, *03:07, *04:01:01:01, *04:01:01:02, *04:01:01:03, *04:01:01:04, *04:01:01:05, *04:01:01:06, *04:01:01:07, *04:01:01:08, *04:01:02:01, *04:01:02:02, *04:01:03, *04:02, *04:03N, *04:04, *04:05, *05:01:01:01, *05:01:01:02, *05:01:01:03, *05:01:01:04, *05:01:02, *05:01:04, *05:01:05, *05:01:06, *05:02, *05:03:01:01, *05:03:01:02, *05:04, *05:05:01:01, *05:05:01:02, *05:05:01:03, *05:05:01:04, *05:05:01:05, *05:05:01:06, *05:05:01:07, *05:05:01:08, *05:05:01:09, *05:05:01:10, *05:05:01:11, *05:05:01:12, *05:05:01:13, *05:05:01:14, *05:05:01:15, *05:05:01:16, *05:05:01:17, *05:05:01:18, *05:05:01:19, *05:05:01:20, *05:06:01:01, *05:06:01:02, *05:07, *05:08, *05:09, *05:10, *05:11, *05:12, *05:13, *05:14, *05:15N, *06:01:01:01, *06:01:01:02, *06:01:03, *06:01:01:04, *06:01:02, *06:02, and any combination thereof.

In some aspects, the beta chain is an HLA-DQ beta chain. Any HLA-DQ beta chain allele known in the art can be used in the compositions and methods disclosed herein. In some aspects the beta chain is selected from an HLA-DQB1*02, HLA-DQB1*03, HLA-DQB1*04, HLA-DQB1*05, and HLA-DQB1*06 allele.

In certain aspects, the DQ beta chain comprises an allele selected from DQB1*02:01:01, DQB1*02:01:02, DQB1*02:01:03, DQB1*02:01:04, DQB1*02:01:05, DQB1*02:01:06, DQB1*02:01:07, DQB1*02:01:08, DQB1*02:01:09, DQB1*02:01:10, DQB1*02:01:11, DQB1*02:01:12, DQB1*02:01:13, DQB1*02:01:14, DQB1*02:01:15, DQB1*02:01:16, DQB1*02:01:17, DQB1*02:01:18, DQB1*02:01:19, DQB1*02:01:20, DQB1*02:01:21, DQB1*02:01:22, DQB1*02:01:23, DQB1*02:01:24, DQB1*02:01:25, DQB1*02:01:26, DQB1*02:01:27, DQB1*02:01:28, DQB1*02:01:29, DQB1*02:01:30, DQB1*02:01:31, DQB1*02:02:01:01, DQB1*02:02:01:02, DQB1*02:02:01:03, DQB1*02:02:01:04, DQB1*02:02:02, DQB1*02:02:03, DQB1*02:02:04, DQB1*02:02:05, DQB1*02:02:06, DQB1*02:02:07, DQB1*02:02:08, DQB1*02:02:09, DQB1*02:03:01, DQB1*02:03:02, DQB1*02:04, DQB1*02:05, DQB1*02:06, DQB1*02:07:01, DQB1*02:07:02, DQB1*02:08, DQB1*02:09, DQB1*02:10, DQB1*02:100, DQB1*02:101, DQB1*02:102, DQB1*02:103, DQB1*02:104, DQB1*02:105, DQB1*02:106, DQB1*02:107, DQB1*02:108, DQB1*02:109, DQB1*02:11, DQB1*02:110, DQB1*02:111, DQB1*02:112, DQB1*02:113, DQB1*02:114, DQB1*02:115, DQB1*02:116, DQB1*02:117, DQB1*02:118, DQB1*02:119, DQB1*02:12, DQB1*02:120, DQB1*02:121, DQB1*02:122, DQB1*02:123, DQB1*02:124, DQB1*02:125, DQB1*02:126, DQB1*02:127, DQB1*02:128, DQB1*02:129N, DQB1*02:13, DQB1*02:130, DQB1*02:131, DQB1*02:132N, DQB1*02:133, DQB1*02:134N, DQB1*02:135, DQB1*02:136, DQB1*02:137, DQB1*02:138, DQB1*02:139, DQB1*02:140, DQB1*02:141, DQB1*02:142, DQB1*02:14:01, DQB1*02:14:02, DQB1*02:15, DQB1*02:16, DQB1*02:17, DQB1*02:18N, DQB1*02:19, DQB1*02:20N, DQB1*02:21, DQB1*02:22, DQB1*02:23, DQB1*02:24, DQB1*02:25, DQB1*02:26, DQB1*02:27, DQB1*02:28, DQB1*02:29, DQB1*02:30, DQB1*02:31, DQB1*02:32, DQB1*02:33, DQB1*02:34, DQB1*02:35, DQB1*02:36, DQB1*02:37, DQB1*02:38, DQB1*02:39, DQB1*02:40, DQB1*02:41, DQB1*02:42, DQB1*02:43, DQB1*02:44, DQB1*02:45, DQB1*02:46, DQB1*02:47, DQB1*02:48, DQB1*02:49, DQB1*02:50, DQB1*02:51, DQB1*02:52, DQB1*02:53Q, DQB1*02:54, DQB1*02:55, DQB1*02:56, DQB1*02:57, DQB1*02:58N, DQB1*02:59, DQB1*02:60, DQB1*02:61, DQB1*02:62, DQB1*02:63, DQB1*02:64, DQB1*02:65, DQB1*02:66, DQB1*02:67NX, DQB1*02:68, DQB1*02:69, DQB1*02:70, DQB1*02:71, DQB1*02:72, DQB1*02:73, DQB1*02:74, DQB1*02:75, DQB1*02:76, DQB1*02:77, DQB1*02:78, DQB1*02:79, DQB1*02:80, DQB1*02:81, DQB1*02:82, DQB1*02:83, DQB1*02:84, DQB1*02:85, DQB1*02:86, DQB1*02:87, DQB1*02:88, DQB1*02:89:01, DQB1*02:89:02, DQB1*02:90, DQB1*02:91, DQB1*02:92, DQB1*02:93, DQB1*02:94, DQB1*02:95, DQB1*02:96N, DQB1*02:97, DQB1*02:98, DQB1*02:99, DQB1*03:01:01:01, DQB1*03:01:01:02, DQB1*03:01:01:03, DQB1*03:01:01:04, DQB1*03:01:01:05, DQB1*03:01:01:06, DQB1*03:01:01:07, DQB1*03:01:01:08, DQB1*03:01:01:09, DQB1*03:01:01:10, DQB1*03:01:01:11, DQB1*03:01:01:12, DQB1*03:01:01:14, DQB1*03:01:01:15, DQB1*03:01:01:16, DQB1*03:01:01:17, DQB1*03:01:01:18, DQB1*03:01:01:19, DQB1*03:01:01:20, DQB1*03:01:02, DQB1*03:01:03, DQB1*03:01:04, DQB1*03:01:05, DQB1*03:01:06, DQB1*03:01:07, DQB1*03:01:08, DQB1*03:01:09, DQB1*03:01:10, DQB1*03:01:11, DQB1*03:01:12, DQB1*03:01:13, DQB1*03:01:14, DQB1*03:01:15, DQB1*03:01:16, DQB1*03:01:17, DQB1*03:01:18, DQB1*03:01:19, DQB1*03:01:20, DQB1*03:01:21, DQB1*03:01:22, DQB1*03:01:23, DQB1*03:01:24, DQB1*03:01:25, DQB1*03:01:26, DQB1*03:01:27, DQB1*03:01:28, DQB1*03:01:29, DQB1*03:01:30, DQB1*03:01:31, DQB1*03:01:32, DQB1*03:01:33, DQB1*03:01:34, DQB1*03:01:35, DQB1*03:01:36, DQB1*03:01:37, DQB1*03:01:38, DQB1*03:01:39, DQB1*03:01:40, DQB1*03:01:41, DQB1*03:01:42, DQB1*03:01:43, DQB1*03:01:44, DQB1*03:01:45, DQB1*03:01:46, DQB1*03:02:01:01, DQB1*03:02:01:02, DQB1*03:02:01:03, DQB1*03:02:01:04, DQB1*03:02:01:05, DQB1*03:02:01:06, DQB1*03:02:01:07, DQB1*03:02:01:08, DQB1*03:02:02, DQB1*03:02:03, DQB1*03:02:04, DQB1*03:02:05, DQB1*03:02:06, DQB1*03:02:07, DQB1*03:02:08, DQB1*03:02:09, DQB1*03:02:10, DQB1*03:02:11, DQB1*03:02:12, DQB1*03:02:13, DQB1*03:02:14, DQB1*03:02:15, DQB1*03:02:16, DQB1*03:02:17, DQB1*03:02:18, DQB1*03:02:19, DQB1*03:02:20, DQB1*03:02:21, DQB1*03:02:22, DQB1*03:02:23, DQB1*03:02:24, DQB1*03:02:25, DQB1*03:02:26, DQB1*03:02:27, DQB1*03:02:28, DQB1*03:02:29, DQB1*03:02:30, DQB1*03:03:02:01, DQB1*03:03:02:02, DQB1*03:03:02: 03, DQB1*03:03:02:04, DQB1*03:03:02:05, DQB1*03:03: 03, DQB1*03:03:04, DQB1*03:03:05, DQB1*03:03:06, DQB1*03:03:07, DQB1*03:03:08, DQB1*03:03:09, DQB1*03:03:10, DQB1*03:03:11, DQB1*03:03:12, DQB1*03:03:13, DQB1*03:03:14, DQB1*03:03:15, DQB1*03:03:16, DQB1*03:03:17, DQB1*03:03:18, DQB1*03:03:19, DQB1*03:03:20, DQB1*03:03:21, DQB1*03:04:01, DQB1*03:04:02, DQB1*03:04:03, DQB1*03:04:04, DQB1*03:05:01, DQB1*03:05:02, DQB1*03:05:03, DQB1*03:05:04, DQB1*03:06, DQB1*03:07, DQB1*03:08, DQB1*03:09, DQB1*03:100, DQB1*03:101, DQB1*03:102, DQB1*03:103, DQB1*03: 104, DQB1*03:105, DQB1*03:106, DQB1*03:107, DQB1*03:108, DQB1*03:109, DQB1*03:10:01, DQB1*03:10:02:01, DQB1*03:10:02:02, DQB1*03:11, DQB1*03:110, DQB1*03:111, DQB1*03:112, DQB1*03: 113, DQB1*03:114, DQB1*03:115, DQB1*03:116, DQB1*03:117, DQB1*03:118N, DQB1*03:119, DQB1*03:12, DQB1*03:120, DQB1*03:121, DQB1*03: 122, DQB1*03:123, DQB1*03:124, DQB1*03:125, DQB1*03:126, DQB1*03:127, DQB1*03:128, DQB1*03: 129, DQB1*03:13, DQB1*03:130, DQB1*03:131, DQB1*03:132, DQB1*03:133, DQB1*03:134, DQB1*03: 135, DQB1*03:136, DQB1*03:137, DQB1*03:138, DQB1*03:139, DQB1*03:140, DQB1*03:141, DQB1*03: 142, DQB1*03:143, DQB1*03:144, DQB1*03:145, DQB1*03:146, DQB1*03:147, DQB1*03:148, DQB1*03: 149, DQB1*03:14:01, DQB1*03:14:02, DQB1*03:15, DQB1*03:150, DQB1*03:151, DQB1*03:152, DQB1*03: 153, DQB1*03:154, DQB1*03:155, DQB1*03:156, DQB1*03:157, DQB1*03:158, DQB1*03:159, DQB1*03: 16, DQB1*03:160, DQB1*03:161, DQB1*03:162, DQB1*03:163, DQB1*03:164, DQB1*03:165, DQB1*03: 166, DQB1*03:167, DQB1*03:168, DQB1*03:169, DQB1*03:170, DQB1*03:171, DQB1*03:172, DQB1*03: 173, DQB1*03:174, DQB1*03:175, DQB1*03:176, DQB1*03:177, DQB1*03:178, DQB1*03:179, DQB1*03: 17:01, DQB1*03:17:02, DQB1*03:18, DQB1*03:180, DQB1*03:181, DQB1*03:182, DQB1*03:183, DQB1*03: 184, DQB1*03:185, DQB1*03:186, DQB1*03:187, DQB1*03:188, DQB1*03:189, DQB1*03:190, DQB1*03: 191, DQB1*03:192, DQB1*03:193, DQB1*03:194, DQB1*03:195, DQB1*03:196, DQB1*03:197Q, DQB1*03:198:01, DQB1*03:198:02, DQB1*03:199, DQB1*03:19:01, DQB1*03:19:02, DQB1*03:19:03, DQB1*03:19:04, DQB1*03:20, DQB1*03:200, DQB1*03: 201, DQB1*03:202, DQB1*03:203, DQB1*03:204, DQB1*03:205, DQB1*03:206, DQB1*03:207, DQB1*03: 208, DQB1*03:209, DQB1*03:21, DQB1*03:210, DQB1*03:211, DQB1*03:212, DQB1*03:213NX, DQB1*03:214, DQB1*03:215, DQB1*03:216, DQB1*03: 217, DQB1*03:218, DQB1*03:219, DQB1*03:220, DQB1*03:221, DQB1*03:222, DQB1*03:223, DQB1*03: 224, DQB1*03:225, DQB1*03:226, DQB1*03:227, DQB1*03:228, DQB1*03:229, DQB1*03:22:01, DQB1*03:22:02, DQB1*03:230, DQB1*03:231, DQB1*03:232, DQB1*03:233, DQB1*03:234, DQB1*03: 235, DQB1*03:236, DQB1*03:237N, DQB1*03:238, DQB1*03:239, DQB1*03:23:01, DQB1*03:23:02, DQB1*03:23:03, DQB1*03:24, DQB1*03:240, DQB1*03: 241, DQB1*03:242, DQB1*03:243, DQB1*03:244, DQB1*03:245, DQB1*03:246, DQB1*03:247, DQB1*03: 248, DQB1*03:249, DQB1*03:250, DQB1*03:251, DQB1*03:252, DQB1*03:253, DQB1*03:254, DQB1*03: 255, DQB1*03:256, DQB1*03:257, DQB1*03:258, DQB1*03:259, DQB1*03:25:01, DQB1*03:25:02, DQB1*03:26, DQB1*03:260, DQB1*03:261, DQB1*03: 262, DQB1*03:263, DQB1*03:264, DQB1*03:265, DQB1*03:266, DQB1*03:267, DQB1*03:268, DQB1*03: 269N, DQB1*03:27, DQB1*03:270, DQB1*03:271, DQB1*03:272, DQB1*03:273, DQB1*03:274, DQB1*03: 275, DQB1*03:277, DQB1*03:278, DQB1*03:279, DQB1*03:28, DQB1*03:280, DQB1*03:281, DQB1*03: 282N, DQB1*03:283, DQB1*03:284, DQB1*03:285, DQB1*03:286, DQB1*03:287, DQB1*03:288, DQB1*03: 289, DQB1*03:29, DQB1*03:290, DQB1*03:291, DQB1*03:292, DQB1*03:293, DQB1*03:294, DQB1*03: 295, DQB1*03:296, DQB1*03:297, DQB1*03:298, DQB1*03:299, DQB1*03:30, DQB1*03:300, DQB1*03: 301, DQB1*03:302, DQB1*03:303N, DQB1*03:304, DQB1*03:305, DQB1*03:306, DQB1*03:307, DQB1*03: 308, DQB1*03:309, DQB1*03:31, DQB1*03:310N, DQB1*03:311, DQB1*03:312, DQB1*03:313, DQB1*03: 314, DQB1*03:315, DQB1*03:316, DQB1*03:317:01, DQB1*03:317:02, DQB1*03:318, DQB1*03:319, DQB1*03:32, DQB1*03:320, DQB1*03:321, DQB1*03: 322, DQB1*03:323, DQB1*03:324, DQB1*03:326, DQB1*03:327, DQB1*03:328, DQB1*03:329, DQB1*03: 33, DQB1*03:330, DQB1*03:331, DQB1*03:332, DQB1*03:333, DQB1*03:334N4 bp, DQB1*03:335, DQB1*03:336, DQB1*03:337, DQB1*03:338N, DQB1*03:339N, DQB1*03:34, DQB1*03:340N, DQB1*03:341, DQB1*03:342, DQB1*03:343, DQB1*03: 344, DQB1*03:345, DQB1*03:346, DQB1*03:347, DQB1*03:348, DQB1*03:349, DQB1*03:35, DQB1*03: 350, DQB1*03:351, DQB1*03:352, DQB1*03:353, DQB1*03:354N, DQB1*03:355, DQB1*03:356NX, DQB1*03:357N, DQB1*03:358N, DQB1*03:36, DQB1*03:37, DQB1*03:38:01, DQB1*03:38:02, DQB1*03:39, DQB1*03:40, DQB1*03:41, DQB1*03:42, DQB1*03:43, DQB1*03:44, DQB1*03:45, DQB1*03:46, DQB1*03:47, DQB1*03:48, DQB1*03:49, DQB1*03:50, DQB1*03:51, DQB1*03:52, DQB1*03:53, DQB1*03:54, DQB1*03:55, DQB1*03:56, DQB1*03:57, DQB1*03:58, DQB1*03:59, DQB1*03:60, DQB1*03:61, DQB1*03:62, DQB1*03:63, DQB1*03:64, DQB1*03:65, DQB1*03:66N, DQB1*03:67, DQB1*03:68, DQB1*03:69, DQB1*03:70, DQB1*03:71, DQB1*03:72, DQB1*03:73, DQB1*03:74, DQB1*03:75, DQB1*03:76, DQB1*03:77, DQB1*03:78, DQB1*03:79, DQB1*03:80, DQB1*03:81, DQB1*03:82, DQB1*03:83, DQB1*03:84N, DQB1*03:85, DQB1*03:86, DQB1*03:87, DQB1*03:88, DQB1*03:89, DQB1*03:90N, DQB1*03:91Q, DQB1*03:92, DQB1*03:93, DQB1*03:94, DQB1*03:95N, DQB1*03:96, DQB1*03:97, DQB1*03:98, DQB1*03:99Q, DQB1*04:01:01:01, DQB1*04:01:01:02, DQB1*04:01:02, DQB1*04:01:03, DQB1*04:01:04, DQB1*04:01:05, DQB1*04:02:01:01, DQB1*04:02:01:04, DQB1*04:02:01:05, DQB1*04:02:01:06, DQB1*04:02:01: 07, DQB1*04:02:01:08, DQB1*04:02:01:09, DQB1*04:02: 01:10, DQB1*04:02:02, DQB1*04:02:03, DQB1*04:02:04, DQB1*04:02:05, DQB1*04:02:06, DQB1*04:02:07, DQB1*04:02:08, DQB1*04:02:09, DQB1*04:02:10, DQB1*04:02:11, DQB1*04:02:12, DQB1*04:02:13, DQB1*04:02:14, DQB1*04:02:15, DQB1*04:02:16, DQB1*04:02:17, DQB1*04:02:18, DQB1*04:03:01, DQB1*04:03:02, DQB1*04:03:03, DQB1*04:04, DQB1*04:05, DQB1*04:06, DQB1*04:07, DQB1*04:08, DQB1*04:09, DQB1*04:10, DQB1*04:11, DQB1*04:12, DQB1*04:13, DQB1*04:14, DQB1*04:15, DQB1*04:16, DQB1*04:17, DQB1*04:18, DQB1*04:19, DQB1*04:20, DQB1*04:21, DQB1*04:22, DQB1*04:23, DQB1*04:24, DQB1*04:25N, DQB1*04:26, DQB1*04:27, DQB1*04:28, DQB1*04:29, DQB1*04:30, DQB1*04:31, DQB1*04:32, DQB1*04:33, DQB1*04:34, DQB1*04:35, DQB1*04:36N, DQB1*04:37, DQB1*04:38, DQB1*04:39, DQB1*04:40, DQB1*04:41N, DQB1*04:42, DQB1*04:43, DQB1*04:44, DQB1*04:45, DQB1*04:46N, DQB1*04:47, DQB1*04:48, DQB1*04:49, DQB1*04:50, DQB1*04:51, DQB1*04:52, DQB1*04:53, DQB1*04:54, DQB1*04:55, DQB1*04:56, DQB1*04:57, DQB1*04:58, DQB1*04:59N, DQB1*04:60, DQB1*04:61, DQB1*04:62, DQB1*05:01:01:01, DQB1*05:01:01:02, DQB1*05:01:01:03, DQB1*05:01:01:04, DQB1*05:01:01:05, DQB1*05:01:02, DQB1*05:01:03, DQB1*05:01:04, DQB1*05:01:05, DQB1*05:01:06, DQB1*05:01:07, DQB1*05:01:08, DQB1*05:01:09, DQB1*05:01:10, DQB1*05:01:11, DQB1*05:01:12, DQB1*05:01:13, DQB1*05:01:14, DQB1*05:01:15, DQB1*05:01:16, DQB1*05:01:17, DQB1*05:01:18, DQB1*05:01:19, DQB1*05:01:20, DQB1*05:01:21, DQB1*05:01:22, DQB1*05:01:23, DQB1*05:01:24:01, DQB1*05:01:24:02, DQB1*05:01:25, DQB1*05:01:26, DQB1*05:01:27, DQB1*05:01:28, DQB1*05:01:29, DQB1*05:01:30, DQB1*05:01:31, DQB1*05:01:32, DQB1*05:01:33, DQB1*05:01:34, DQB1*05:02:01:01, DQB1*05:02:01:02, DQB1*05:02:01:03, DQB1*05:02:01:04, DQB1*05:02:01:05, DQB1*05:02:01:06, DQB1*05:02:02, DQB1*05:02:03, DQB1*05:02:04, DQB1*05:02:05, DQB1*05:02:06, DQB1*05:02:07, DQB1*05:02:08, DQB1*05:02:09, DQB1*05:02:10, DQB1*05:02:11, DQB1*05:02:12, DQB1*05:02:13, DQB1*05:02:14, DQB1*05:02:15, DQB1*05:02:16, DQB1*05:02:17, DQB1*05:02:18, DQB1*05:02:19, DQB1*05:03:01:01, DQB1*05:03:01:02, DQB1*05:03:01:03, DQB1*05:03:02, DQB1*05:03:03, DQB1*05:03:04, DQB1*05:03:05, DQB1*05:03:06, DQB1*05:03:07, DQB1*05:03:08, DQB1*05:03:09, DQB1*05:03:10, DQB1*05:03:11, DQB1*05:03:12, DQB1*05:03:13, DQB1*05:03:14, DQB1*05:03:15, DQB1*05:03:16, DQB1*05:03:17, DQB1*05:03:18, DQB1*05:03:19, DQB1*05:03:20, DQB1*05:04, DQB1*05:05:01, DQB1*05:05:02, DQB1*05:06:01, DQB1*05:06:02, DQB1*05:07, DQB1*05:08, DQB1*05:09, DQB1*05:10, DQB1*05:100, DQB1*05:101, DQB1*05:102, DQB1*05:103, DQB1*05:104, DQB1*05:105, DQB1*05:106, DQB1*05:107, DQB1*05:108, DQB1*05:109, DQB1*05:110N, DQB1*05:111, DQB1*05:112, DQB1*05:113, DQB1*05:114, DQB1*05:115, DQB1*05:116, DQB1*05:117, DQB1*05:118, DQB1*05:119, DQB1*05:11:01, DQB1*05:11:02, DQB1*05:12, DQB1*05:120, DQB1*05:121, DQB1*05:122, DQB1*05:123, DQB1*05:124, DQB1*05:125, DQB1*05:126, DQB1*05:127, DQB1*05:128N, DQB1*05:129, DQB1*05:13, DQB1*05:130, DQB1*05:131, DQB1*05:132Q, DQB1*05:133, DQB1*05:134, DQB1*05:135, DQB1*05:136, DQB1*05:137, DQB1*05:138, DQB1*05:139, DQB1*05:14, DQB1*05:140, DQB1*05:141, DQB1*05:142, DQB1*05:143, DQB1*05:144, DQB1*05:145, DQB1*05:146, DQB1*05:147, DQB1*05:148, DQB1*05:149, DQB1*05:15, DQB1*05:150, DQB1*05:151, DQB1*05:152, DQB1*05:153, DQB1*05:154, DQB1*05:155, DQB1*05:156, DQB1*05:157, DQB1*05:158, DQB1*05:159, DQB1*05:16, DQB1*05:160, DQB1*05:161, DQB1*05:162, DQB1*05:163, DQB1*05:164, DQB1*05:165, DQB1*05:166, DQB1*05:167, DQB1*05:168, DQB1*05:169, DQB1*05:17, DQB1*05:170, DQB1*05:171, DQB1*05:172, DQB1*05:173, DQB1*05:174, DQB1*05:175, DQB1*05:176, DQB1*05:177, DQB1*05:178, DQB1*05:179, DQB1*05:18, DQB1*05:180, DQB1*05:181, DQB1*05:182, DQB1*05:183, DQB1*05:184, DQB1*05:185N, DQB1*05:186, DQB1*05:187, DQB1*05:188, DQB1*05:189, DQB1*05:19, DQB1*05:190, DQB1*05:191, DQB1*05:192, DQB1*05:193, DQB1*05:194, DQB1*05:195, DQB1*05:196, DQB1*05:197, DQB1*05:198, DQB1*05:199, DQB1*05:20, DQB1*05:200, DQB1*05:201, DQB1*05:202, DQB1*05:203, DQB1*05:204, DQB1*05:205, DQB1*05:206N, DQB1*05:207, DQB1*05:208N5 bp, DQB1*05:209, DQB1*05:21, DQB1*05:210, DQB1*05:211, DQB1*05:212, DQB1*05:213, DQB1*05:214, DQB1*05:215N, DQB1*05:216, DQB1*05:217, DQB1*05:22, DQB1*05:23, DQB1*05:24, DQB1*05:25, DQB1*05:26, DQB1*05:27, DQB1*05:28, DQB1*05:29, DQB1*05:30, DQB1*05:31, DQB1*05:32, DQB1*05:33, DQB1*05:34, DQB1*05:35, DQB1*05:36, DQB1*05:37, DQB1*05:38, DQB1*05:39, DQB1*05:40, DQB1*05:41N, DQB1*05:42, DQB1*05:43:01, DQB1*05:43:02, DQB1*05:44, DQB1*05:45, DQB1*05:46, DQB1*05:47, DQB1*05:48, DQB1*05:49, DQB1*05:50, DQB1*05:51, DQB1*05:52, DQB1*05:53, DQB1*05:54, DQB1*05:55, DQB1*05:56, DQB1*05:57, DQB1*05:58, DQB1*05:59, DQB1*05:60, DQB1*05:61, DQB1*05:62, DQB1*05:63, DQB1*05:64, DQB1*05:65, DQB1*05:66:01, DQB1*05:66:02, DQB1*05:67, DQB1*05:68, DQB1*05:69, DQB1*05:70, DQB1*05:71, DQB1*05:72, DQB1*05:73, DQB1*05:74, DQB1*05:75, DQB1*05:76, DQB1*05:77, DQB1*05:78, DQB1*05:79, DQB1*05:80, DQB1*05:81, DQB1*05:82, DQB1*05:83, DQB1*05:84, DQB1*05:85, DQB1*05:86, DQB1*05:87Q, DQB1*05:88, DQB1*05:89:01, DQB1*05:89:02, DQB1*05:90N, DQB1*05:91, DQB1*05:92, DQB1*05:93, DQB1*05:94, DQB1*05:95, DQB1*05:96, DQB1*05:97, DQB1*05:98, DQB1*05:99, DQB1*06:01:01:01, DQB1*06:01:01:02, DQB1*06:01:02, DQB1*06:01:03, DQB1*06:01:04, DQB1*06:01:05, DQB1*06:01:06, DQB1*06:01:07, DQB1*06:01:08, DQB1*06:01:09, DQB1*06:01:10, DQB1*06:01:11, DQB1*06:01:12, DQB1*06:01:13, DQB1*06:01:14, DQB1*06:01:15, DQB1*06:01:16, DQB1*06:01:17, DQB1*06:01:18, DQB1*06:01:19, DQB1*06:01:20, DQB1*06:01:21, DQB1*06:02:01:01, DQB1*06:02:01:02, DQB1*06:02:01:03, DQB1*06:02:01:04, DQB1*06:02:02, DQB1*06:02:03, DQB1*06:02:04, DQB1*06:02:05, DQB1*06:02:06, DQB1*06:02:07, DQB1*06:02:08, DQB1*06:02:09, DQB1*06:02:10, DQB1*06:02:11, DQB1*06:02:12, DQB1*06:02:13, DQB1*06:02:14, DQB1*06:02:15, DQB1*06:02:16, DQB1*06:02:17, DQB1*06:02:18, DQB1*06:02:19, DQB1*06:02:20, DQB1*06:02:21, DQB1*06:02:22, DQB1*06:02:23, DQB1*06:02:24, DQB1*06:02:25, DQB1*06:02:26, DQB1*06:02:27, DQB1*06:02:28, DQB1*06:02:29, DQB1*06:02:30, DQB1*06:02:31, DQB1*06:02:32, DQB1*06:02:33, DQB1*06:02:34, DQB1*06:02:35, DQB1*06:02:36, DQB1*06:02:37, DQB1*06:02:38, DQB1*06:03:01:01, DQB1*06:03:01:02, DQB1*06:03:01:03, DQB1*06:03:02, DQB1*06:03:03, DQB1*06:03:04, DQB1*06:03:05, DQB1*06:03:06, DQB1*06:03:07, DQB1*06:03:08, DQB1*06:03:09, DQB1*06:03:10, DQB1*06:03:11, DQB1*06:03:12, DQB1*06:03:13, DQB1*06:03:14, DQB1*06:03:15, DQB1*06:03:16, DQB1*06:03:17, DQB1*06:03:18, DQB1*06:03:19, DQB1*06:03:20, DQB1*06:03:21, DQB1*06:03:22, DQB1*06:03:23, DQB1*06:03:24, DQB1*06:03:25, DQB1*06:03:26, DQB1*06:03:27, DQB1*06:03:28, DQB1*06:03:29, DQB1*06:03:30, DQB1*06:03:31, DQB1*06:03:32, DQB1*06:03:33, DQB1*06:03:34, DQB1*06:03:35, DQB1*06:04:01, DQB1*06:04:02, DQB1*06:04:03, DQB1*06:04:04, DQB1*06:04:05, DQB1*06:04:06, DQB1*06:04:07, DQB1*06:04:08, DQB1*06:04:09, DQB1*06:04:10, DQB1*06:04:11, DQB1*06:04:12, DQB1*06:05:01, DQB1*06:05:02, DQB1*06:06, DQB1*06:07:01, DQB1*06:07:02, DQB1*06:08:01, DQB1*06:08:02, DQB1*06:08:03, DQB1*06:09:01:01, DQB1*06:09:01:02, DQB1*06:09:02, DQB1*06:09:03, DQB1*06:09:04, DQB1*06:09:05, DQB1*06:09:06, DQB1*06:09:07, DQB1*06:09:08, DQB1*06:09:09, DQB1*06:09:10, DQB1*06:10, DQB1*06:100, DQB1*06:101, DQB1*06:102N, DQB1*06:103, DQB1*06:104, DQB1*06:105, DQB1*06:106, DQB1*06:107, DQB1*06:108, DQB1*06:109, DQB1*06:110, DQB1*06:111, DQB1*06:112N, DQB1*06:113, DQB1*06:114, DQB1*06:115, DQB1*06:116, DQB1*06:117, DQB1*06:118:01, DQB1*06:118:02, DQB1*06:118:03, DQB1*06:119, DQB1*06:11:01, DQB1*06:11:02, DQB1*06:11:03, DQB1*06:11:04, DQB1*06:12, DQB1*06:120, DQB1*06:121, DQB1*06:122, DQB1*06:123, DQB1*06:124, DQB1*06:125, DQB1*06:126, DQB1*06:127, DQB1*06:128, DQB1*06:129, DQB1*06:130, DQB1*06:131, DQB1*06:132, DQB1*06:133, DQB1*06:134, DQB1*06:135, DQB1*06:136, DQB1*06:137, DQB1*06:138, DQB1*06:139, DQB1*06:13:01, DQB1*06:13:02, DQB1*06:13:03, DQB1*06:140, DQB1*06:141, DQB1*06:142, DQB1*06:143, DQB1*06:144N, DQB1*06:145, DQB1*06:146:01, DQB1*06:146:02, DQB1*06:147, DQB1*06:148, DQB1*06:149, DQB1*06:14:01, DQB1*06:14:02, DQB1*06:14:03, DQB1*06:150, DQB1*06:151, DQB1*06:152, DQB1*06:153:01, DQB1*06:153:02, DQB1*06:154, DQB1*06:155, DQB1*06:156, DQB1*06:157, DQB1*06:158N, DQB1*06:159, DQB1*06:15:01, DQB1*06:15:02, DQB1*06:16, DQB1*06:160, DQB1*06:161, DQB1*06:162, DQB1*06:163, DQB1*06:164, DQB1*06:165, DQB1*06:166, DQB1*06:167, DQB1*06:168, DQB1*06:169, DQB1*06:17, DQB1*06:170, DQB1*06:171, DQB1*06:172, DQB1*06:173, DQB1*06:174, DQB1*06:175, DQB1*06:176, DQB1*06:177, DQB1*06:178, DQB1*06:179N, DQB1*06:180, DQB1*06:181, DQB1*06:182, DQB1*06:183, DQB1*06:184, DQB1*06:185, DQB1*06:186, DQB1*06:187, DQB1*06:188, DQB1*06:189, DQB1*06:18:01, DQB1*06:18:02, DQB1*06:190:01, DQB1*06:190:02, DQB1*06:191, DQB1*06:192, DQB1*06:193N, DQB1*06:194, DQB1*06:195, DQB1*06:196, DQB1*06:197, DQB1*06:198, DQB1*06:199, DQB1*06:19:01, DQB1*06:19:02, DQB1*06:20, DQB1*06:200, DQB1*06:201, DQB1*06:202, DQB1*06:203, DQB1*06:204, DQB1*06:205, DQB1*06:206:01, DQB1*06:206:02, DQB1*06:207, DQB1*06:208, DQB1*06:209, DQB1*06:21, DQB1*06:210, DQB1*06:211, DQB1*06:212, DQB1*06:213, DQB1*06:214, DQB1*06:215, DQB1*06:216N, DQB1*06:217, DQB1*06:218, DQB1*06:219, DQB1*06:221, DQB1*06:222, DQB1*06:223, DQB1*06:224, DQB1*06:225, DQB1*06:226, DQB1*06:227, DQB1*06:228, DQB1*06:229, DQB1*06:22:01, DQB1*06:22:02, DQB1*06:22:03, DQB1*06:23, DQB1*06:230, DQB1*06:231, DQB1*06:232, DQB1*06:233, DQB1*06:234, DQB1*06:235, DQB1*06:236, DQB1*06:237, DQB1*06:238, DQB1*06:239, DQB1*06:24, DQB1*06:240, DQB1*06:241, DQB1*06:242, DQB1*06:243, DQB1*06:

244, DQB1*06:245, DQB1*06:246, DQB1*06:247, DQB1*06:248, DQB1*06:249, DQB1*06:25, DQB1*06:250, DQB1*06:251, DQB1*06:252N, DQB1*06:253, DQB1*06:254, DQB1*06:255, DQB1*06:256, DQB1*06:257, DQB1*06:258, DQB1*06:259, DQB1*06:260, DQB1*06:261, DQB1*06:262, DQB1*06:263, DQB1*06:264, DQB1*06:265, DQB1*06:266, DQB1*06:267, DQB1*06:268, DQB1*06:269, DQB1*06:26N, DQB1*06:270:01, DQB1*06:270:02, DQB1*06:271, DQB1*06:272, DQB1*06:273, DQB1*06:274, DQB1*06:275, DQB1*06:276, DQB1*06:277, DQB1*06:278, DQB1*06:279, DQB1*06:27:01, DQB1*06:27:02, DQB1*06:28, DQB1*06:280, DQB1*06:281, DQB1*06:282, DQB1*06:283, DQB1*06:284, DQB1*06:285, DQB1*06:286, DQB1*06:287, DQB1*06:288, DQB1*06:289, DQB1*06:29, DQB1*06:290, DQB1*06:291, DQB1*06:292, DQB1*06:293, DQB1*06:294, DQB1*06:295, DQB1*06:296, DQB1*06:297, DQB1*06:298, DQB1*06:299, DQB1*06:30, DQB1*06:300, DQB1*06:301, DQB1*06:302, DQB1*06:303N, DQB1*06:304N, DQB1*06:305, DQB1*06:306N, DQB1*06:307, DQB1*06:308N, DQB1*06:309, DQB1*06:31, DQB1*06:310, DQB1*06:311, DQB1*06:312, DQB1*06:313, DQB1*06:314, DQB1*06:315, DQB1*06:316, DQB1*06:317N, DQB1*06:318, DQB1*06:319, DQB1*06:320, DQB1*06:321, DQB1*06:322, DQB1*06:323, DQB1*06:324, DQB1*06:325, DQB1*06:326, DQB1*06:32:01, DQB1*06:32:02, DQB1*06:33, DQB1*06:34, DQB1*06:35, DQB1*06:36, DQB1*06:37, DQB1*06:38, DQB1*06:39, DQB1*06:40, DQB1*06:41, DQB1*06:42, DQB1*06:43, DQB1*06:44, DQB1*06:45, DQB1*06:46, DQB1*06:47, DQB1*06:48:01, DQB1*06:48:02, DQB1*06:49, DQB1*06:50, DQB1*06:51:01, DQB1*06:51:02, DQB1*06:52, DQB1*06:53:01, DQB1*06:53:02, DQB1*06:54N, DQB1*06:55, DQB1*06:56, DQB1*06:57, DQB1*06:58, DQB1*06:59, DQB1*06:60, DQB1*06:61, DQB1*06:62, DQB1*06:63, DQB1*06:64, DQB1*06:65, DQB1*06:66, DQB1*06:67, DQB1*06:68, DQB1*06:69:01, DQB1*06:69:02, DQB1*06:70, DQB1*06:71, DQB1*06:72, DQB1*06:73, DQB1*06:74, DQB1*06:75NX, DQB1*06:76, DQB1*06:77N, DQB1*06:78, DQB1*06:79:01, DQB1*06:79:02, DQB1*06:80, DQB1*06:81, DQB1*06:82, DQB1*06:83, DQB1*06:84, DQB1*06:85, DQB1*06:86, DQB1*06:87, DQB1*06:88, DQB1*06:89, DQB1*06:90, DQB1*06:91, DQB1*06:92:01, DQB1*06:92:02, DQB1*06:93, DQB1*06:94, DQB1*06:95, DQB1*06:96:01, DQB1*06:96:02, DQB1*06:97, DQB1*06:98, DQB1*06:99:01, DQB1*06:99:02, and any combination thereof.

II.D.3. HLA-DR Class II Molecules

In some aspects, the alpha chain is an HLA-DR alpha chain. Any HLA-DR alpha chain allele known in the art can be used in the compositions and methods disclosed herein. In some aspects, the alpha chain is an HLA-DRA*01 allele. In some aspects, the alpha chain is an HLA-DRA1 allele selected from *01:01:01:01, *01:01:01:02, *01:01:01:03, *01:01:02, *01:02:01, *01:02:02, *01:02:03, and any combination thereof.

In some aspects, the beta chain is an HLA-DR beta chain. Any HLA-DR beta chain allele known in the art can be used in the compositions and methods disclosed herein. In some aspects the beta chain is selected from an HLA-DRB1*01, HLA-DRB1*03, HLA-DRB1*04, HLA-DRB1*07, HLA-DRB1*08, HLA-DRB1*09, HLA-DRB1*10, HLA-DRB1*11, HLA-DRB1*12, HLA-DRB1*13, HLA- DRB1*14, HLA-DRB1*15, and HLA-DRB1*16 allele. In some aspects, the beta chain is a DRB3 allele. In some aspects, the beta chain is a DRB4 allele. In some aspects, the beta chain is a DRB5 allele.

In some aspects the beta chain is selected from DRB1*01:01:01, DRB1*01:01:02, DRB1*01:01:03, DRB1*01:01:04, DRB1*01:01:05, DRB1*01:01:06, DRB1*01:01:07, DRB1*01:01:08, DRB1*01:01:09, DRB1*01:01:10, DRB1*01:01:11, DRB1*01:01:12, DRB1*01:01:13, DRB1*01:01:14, DRB1*01:01:15, DRB1*01:01:16, DRB1*01:01:17, DRB1*01:01:18, DRB1*01:01:19, DRB1*01:01:20, DRB1*01:01:21, DRB1*01:01:22, DRB1*01:01:23, DRB1*01:01:24, DRB1*01:01:25, DRB1*01:01:26, DRB1*01:01:27, DRB1*01:01:28, DRB1*01:01:29, DRB1*01:01:30, DRB1*01:01:31, DRB1*01:01:32, DRB1*01:01:33, DRB1*01:02:01:01, DRB1*01:02:01:02, DRB1*01:02:02, DRB1*01:02:03, DRB1*01:02:04, DRB1*01:02:05, DRB1*01:02:06, DRB1*01:02:07, DRB1*01:02:08, DRB1*01:02:09, DRB1*01:02:10, DRB1*01:02:11, DRB1*01:02:12, DRB1*01:02:13, DRB1*01:03:01, DRB1*01:03:02, DRB1*01:03:03, DRB1*01:03:04, DRB1*01:04, DRB1*01:05, DRB1*01:06, DRB1*01:07, DRB1*01:08, DRB1*01:09, DRB1*01:10, DRB1*01:100, DRB1*01:11:01, DRB1*01:11:02, DRB1*01:12, DRB1*01:13, DRB1*01:14, DRB1*01:15, DRB1*01:16, DRB1*01:17, DRB1*01:18:01, DRB1*01:18:02, DRB1*01:19, DRB1*01:20:01, DRB1*01:20:02, DRB1*01:21, DRB1*01:22, DRB1*01:23, DRB1*01:24:01, DRB1*01:24:02, DRB1*01:25, DRB1*01:26, DRB1*01:27, DRB1*01:28, DRB1*01:29:01, DRB1*01:29:02, DRB1*01:30, DRB1*01:31, DRB1*01:32, DRB1*01:33N, DRB1*01:34, DRB1*01:35, DRB1*01:36, DRB1*01:37, DRB1*01:38, DRB1*01:39N, DRB1*01:40N, DRB1*01:41, DRB1*01:42, DRB1*01:43, DRB1*01:44:01, DRB1*01:44:02, DRB1*01:45, DRB1*01:46, DRB1*01:47, DRB1*01:48, DRB1*01:49, DRB1*01:50, DRB1*01:51, DRB1*01:52N, DRB1*01:53, DRB1*01:54, DRB1*01:55, DRB1*01:56, DRB1*01:57, DRB1*01:58, DRB1*01:59, DRB1*01:60, DRB1*01:61, DRB1*01:62N, DRB1*01:63, DRB1*01:64, DRB1*01:65:01, DRB1*01:65:02, DRB1*01:66, DRB1*01:67, DRB1*01:68N, DRB1*01:69, DRB1*01:70, DRB1*01:71, DRB1*01:72, DRB1*01:73, DRB1*01:74, DRB1*01:75, DRB1*01:76, DRB1*01:77, DRB1*01:78, DRB1*01:79, DRB1*01:80, DRB1*01:81, DRB1*01:82, DRB1*01:83, DRB1*01:84, DRB1*01:85, DRB1*01:86, DRB5*01:87, DRB1*01:88, DRB1*01:89, DRB1*01:90, DRB1*01:91Q, DRB1*01:92, DRB1*01:93, DRB1*01:94, DRB1*01:95, DRB1*01:96, DRB1*01:97, DRB1*01:98, DRB1*01:99, DRB1*03:01:01:01, DRB1*03:01:01:02, DRB1*03:01:01:03, DRB1*03:01:02, DRB1*03:01:03, DRB1*03:01:04, DRB1*03:01:05, DRB1*03:01:06, DRB1*03:01:07, DRB1*03:01:08, DRB1*03:01:09, DRB1*03:01:10, DRB1*03:01:11, DRB1*03:01:12, DRB1*03:01:13, DRB1*03:01:14, DRB1*03:01:15, DRB1*03:01:16, DRB1*03:01:17, DRB1*03:01:18, DRB1*03:01:19, DRB1*03:01:20, DRB1*03:01:21, DRB1*03:01:22, DRB1*03:01:23, DRB1*03:01:24, DRB1*03:01:25, DRB1*03:01:26, DRB1*03:01:27, DRB1*03:01:28, DRB1*03:02:01, DRB1*03:02:02, DRB1*03:02:03, DRB1*03:03, DRB1*03:04:01, DRB1*03:04:02, DRB1*03:05:01, DRB1*03:05:02, DRB1*03:05:03, DRB1*03:06, DRB1*03:07:01, DRB1*03:07:02, DRB1*03:08, DRB1*03:09, DRB1*03:10, DRB1*03:100:01, DRB1*03:100:02, DRB1*03:101, DRB1*03:102, DRB1*03:103, DRB1*03:104, DRB1*03:105, DRB1*03:106, DRB1*03:

107, DRB1*03:108, DRB1*03:109, DRB1*03:110, DRB1*03:111, DRB1*03:112, DRB1*03:113, DRB1*03:114, DRB1*03:115, DRB1*03:116, DRB1*03:117, DRB1*03:118, DRB1*03:119, DRB1*03:11:01, DRB1*03:12, DRB1*03:120, DRB1*03:121, DRB1*03:122, DRB1*03:123, DRB1*03:124, DRB1*03:125, DRB1*03:126, DRB1*03:127, DRB1*03:128, DRB1*03:129, DRB1*03:130, DRB1*03:131, DRB1*03:132, DRB1*03:133, DRB1*03:134, DRB1*03:135, DRB1*03:136, DRB1*03:137, DRB1*03:138, DRB1*03:139, DRB1*03:13:01, DRB1*03:13:02, DRB1*03:14, DRB1*03:140, DRB1*03:141, DRB1*03:142, DRB1*03:143, DRB1*03:144, DRB1*03:145, DRB1*03:146, DRB1*03:147, DRB1*03:148, DRB1*03:149, DRB1*03:150, DRB1*03:151, DRB1*03:152, DRB1*03:153, DRB1*03:154, DRB1*03:155, DRB1*03:156N, DRB1*03:157, DRB1*03:158, DRB1*03:15:01, DRB1*03:15:02, DRB1*03:16, DRB1*03:17, DRB1*03:18, DRB1*03:19, DRB1*03:20, DRB1*03:21, DRB1*03:22, DRB1*03:23, DRB1*03:24, DRB1*03:25:01, DRB1*03:25:02, DRB1*03:26, DRB1*03:27, DRB1*03:28, DRB1*03:29, DRB1*03:30, DRB1*03:31, DRB1*03:32, DRB1*03:33, DRB1*03:34, DRB1*03:35, DRB1*03:36, DRB1*03:37, DRB1*03:38, DRB1*03:39, DRB1*03:40, DRB1*03:41:01, DRB1*03:41:02, DRB1*03:42, DRB1*03:43, DRB1*03:44, DRB1*03:45, DRB1*03:46, DRB1*03:47, DRB1*03:48, DRB1*03:49, DRB1*03:50, DRB1*03:51, DRB1*03:52, DRB1*03:53, DRB1*03:54, DRB1*03:55, DRB1*03:56, DRB1*03:57, DRB1*03:58, DRB1*03:59, DRB1*03:60, DRB1*03:61, DRB1*03:62, DRB1*03:63, DRB1*03:64, DRB1*03:65, DRB1*03:66, DRB1*03:67N, DRB1*03:68N, DRB1*03:69, DRB1*03:70, DRB1*03:71:01, DRB1*03:71:02, DRB1*03:72, DRB1*03:73, DRB1*03:74, DRB1*03:75, DRB1*03:76, DRB1*03:77, DRB1*03:78, DRB1*03:79, DRB1*03:80, DRB1*03:81, DRB1*03:82, DRB1*03:83, DRB1*03:84, DRB1*03:85, DRB1*03:86, DRB1*03:87, DRB1*03:88, DRB1*03:89, DRB1*03:90, DRB1*03:91, DRB1*03:92, DRB1*03:93, DRB1*03:94, DRB1*03:95, DRB1*03:96, DRB1*03:97, DRB1*03:98, DRB1*03:99, DRB1*04:01:01:01, DRB1*04:01:01:02, DRB1*04:01:01:03, DRB1*04:01:02, DRB1*04:01:03, DRB1*04:01:04, DRB1*04:01:05, DRB1*04:01:06, DRB1*04:01:07, DRB1*04:01:08, DRB1*04:01:09, DRB1*04:01:10, DRB1*04:01:11, DRB1*04:01:12, DRB1*04:01:13, DRB1*04:01:14, DRB1*04:01:15, DRB1*04:01:16, DRB1*04:01:17, DRB1*04:01:18, DRB1*04:01:19, DRB1*04:01:20, DRB1*04:01:21, DRB1*04:02:01, DRB1*04:02:02, DRB1*04:02:03, DRB1*04:02:04, DRB1*04:02:05, DRB1*04:02:06, DRB1*04:03:01:01, DRB1*04:03:01:02, DRB1*04:03:02, DRB1*04:03:03, DRB1*04:03:04, DRB1*04:03:05, DRB1*04:03:06, DRB1*04:03:07, DRB1*04:03:08, DRB1*04:03:09, DRB1*04:03:10, DRB1*04:03:11, DRB1*04:03:12, DRB1*04:03:13, DRB1*04:03:14, DRB1*04:03:15, DRB1*04:04:01, DRB1*04:04:02, DRB1*04:04:03, DRB1*04:04:04, DRB1*04:04:05, DRB1*04:04:06, DRB1*04:04:07, DRB1*04:04:08, DRB1*04:04:09, DRB1*04:04:10, DRB1*04:04:11, DRB1*04:04:12, DRB1*04:04:13, DRB1*04:04:14, DRB1*04:04:15, DRB1*04:05:01:01, DRB1*04:05:01:02, DRB1*04:05:01:03, DRB1*04:05:02, DRB1*04:05:03, DRB1*04:05:04, DRB1*04:05:05, DRB1*04:05:06, DRB1*04:05:07, DRB1*04:05:08, DRB1*04:05:09, DRB1*04:05:10, DRB1*04:05:11, DRB1*04:05:13, DRB1*04:05:14, DRB1*04:05:15, DRB1*04:05:16, DRB1*04:05:17, DRB1*04:05:18, DRB1*04:05:19, DRB1*04:05:20, DRB1*04:06:01, DRB1*04:06:02,

DRB1*04:06:03, DRB1*04:06:04, DRB1*04:06:05, DRB1*04:06:06, DRB1*04:06:07, DRB1*04:07:01:01, DRB1*04:07:01:02, DRB1*04:07:02, DRB1*04:07:03, DRB1*04:07:04, DRB1*04:07:05, DRB1*04:07:06, DRB1*04:08:01, DRB1*04:08:02, DRB1*04:08:03, DRB1*04:08:04, DRB1*04:09, DRB1*04:100, DRB1*04: 101, DRB1*04:102, DRB1*04:103, DRB1*04:104, DRB1*04:105:01, DRB1*04:105:02, DRB1*04:106, DRB1*04:107, DRB1*04:108, DRB1*04:109, DRB1*04: 10:01, DRB1*04:10:02, DRB1*04:10:03, DRB1*04:110, DRB1*04:111, DRB1*04:112, DRB1*04:113, DRB1*04: 114, DRB1*04:115, DRB1*04:116, DRB1*04:117, DRB1*04:118, DRB1*04:119N, DRB1*04:11:01, DRB1*04:11:02, DRB1*04:11:03, DRB1*04:11:04, DRB1*04:11:05, DRB1*04:12, DRB1*04:120N, DRB1*04:121, DRB1*04:122, DRB1*04:123, DRB1*04: 124, DRB1*04:125, DRB1*04:126, DRB1*04:127, DRB1*04:128, DRB1*04:129, DRB1*04:13, DRB1*04: 130, DRB1*04:131:01, DRB1*04:131:02, DRB1*04:132, DRB1*04:133, DRB1*04:134, DRB1*04:135, DRB1*04: 136, DRB1*04:137, DRB1*04:138, DRB1*04:139, DRB1*04:14, DRB1*04:140, DRB1*04:141, DRB1*04: 142N, DRB1*04:143, DRB1*04:144, DRB1*04:145, DRB1*04:146, DRB1*04:147, DRB1*04:148, DRB1*04: 149, DRB1*04:15, DRB1*04:150, DRB1*04:151, DRB1*04:152, DRB1*04:153, DRB1*04:154, DRB1*04: 155, DRB1*04:156, DRB1*04:157N, DRB1*04:158N, DRB1*04:159, DRB1*04:16, DRB1*04:160, DRB1*04: 161, DRB1*04:162, DRB1*04:163, DRB1*04:164, DRB1*04:165, DRB1*04:166, DRB1*04:167, DRB1*04: 168, DRB1*04:169, DRB1*04:170, DRB1*04:171, DRB1*04:172, DRB1*04:173, DRB1*04:174, DRB1*04: 175, DRB1*04:176, DRB1*04:177, DRB1*04:178N, DRB1*04:179, DRB1*04:17:01, DRB1*04:17:02, DRB1*04:18, DRB1*04:180, DRB1*04:181, DRB1*04: 182, DRB1*04:183, DRB1*04:184, DRB1*04:185, DRB1*04:186N, DRB1*04:187, DRB1*04:188, DRB1*04: 189, DRB1*04:19, DRB1*04:190, DRB1*04:191, DRB1*04:192, DRB1*04:193, DRB1*04:194, DRB1*04: 195, DRB1*04:196, DRB1*04:197, DRB1*04:198, DRB1*04:199, DRB1*04:20, DRB1*04:200, DRB1*04: 201, DRB1*04:202, DRB1*04:203, DRB1*04:204, DRB1*04:205, DRB1*04:206, DRB1*04:207, DRB1*04: 208, DRB1*04:209, DRB1*04:21, DRB1*04:210, DRB1*04:211, DRB1*04:212N, DRB1*04:213, DRB1*04: 214N, DRB1*04:215, DRB1*04:216, DRB1*04:217, DRB1*04:218, DRB1*04:219, DRB1*04:22, DRB1*04: 220, DRB1*04:221, DRB1*04:222, DRB1*04:223, DRB1*04:224, DRB1*04:225, DRB1*04:226:01, DRB1*04:226:02, DRB1*04:227, DRB1*04:228, DRB1*04:229, DRB1*04:23, DRB1*04:230, DRB1*04: 231, DRB1*04:232, DRB1*04:233, DRB1*04:234, DRB1*04:235, DRB1*04:236, DRB1*04:237, DRB1*04: 238, DRB1*04:239, DRB1*04:24, DRB1*04:240, DRB1*04:241, DRB1*04:242, DRB1*04:243, DRB1*04: 244, DRB1*04:245, DRB1*04:246, DRB1*04:247N, DRB1*04:248, DRB1*04:249, DRB1*04:25, DRB1*04: 250, DRB1*04:251, DRB1*04:252, DRB1*04:253, DRB1*04:254, DRB1*04:255, DRB1*04:256, DRB1*04: 257, DRB1*04:258, DRB1*04:259, DRB1*04:26, DRB1*04:260, DRB1*04:261, DRB1*04:262, DRB1*04: 263, DRB1*04:264N, DRB1*04:265, DRB1*04:266N, DRB1*04:267N, DRB1*04:268, DRB1*04:269, DRB1*04: 27, DRB1*04:270, DRB1*04:271, DRB1*04:272, DRB1*04:28, DRB1*04:29, DRB1*04:30, DRB1*04:31, DRB1*04:32, DRB1*04:33, DRB1*04:34, DRB1*04:35, DRB1*04:36, DRB1*04:37, DRB1*04:38, DRB1*04:39,

DRB1*04:40, DRB1*04:41, DRB1*04:42, DRB1*04:43, DRB1*04:44:01, DRB1*04:44:02, DRB1*04:45, DRB1*04:46, DRB1*04:47, DRB1*04:48, DRB1*04:49, DRB1*04:50, DRB1*04:51, DRB1*04:52, DRB1*04:53: 01, DRB1*04:53:02, DRB1*04:54, DRB1*04:55, DRB1*04:56:01, DRB1*04:56:02, DRB1*04:57, DRB1*04:58, DRB1*04:59, DRB1*04:60, DRB1*04:61, DRB1*04:62, DRB1*04:63, DRB1*04:64, DRB1*04:65, DRB1*04:66, DRB1*04:67, DRB1*04:68, DRB1*04:69, DRB1*04:70, DRB1*04:71, DRB1*04:72:01, DRB1*04: 72:02, DRB1*04:73:01, DRB1*04:73:02, DRB1*04:74, DRB1*04:75, DRB1*04:76, DRB1*04:77, DRB1*04:78, DRB1*04:79, DRB1*04:80, DRB1*04:81N, DRB1*04:82, DRB1*04:83, DRB1*04:84, DRB1*04:85, DRB1*04:86, DRB1*04:87, DRB1*04:88, DRB1*04:89, DRB1*04:90, DRB1*04:91, DRB1*04:92, DRB1*04:93, DRB1*04:94: 01N, DRB1*04:95:01, DRB1*04:95:02, DRB1*04:96, DRB1*04:97, DRB1*04:98:01, DRB1*04:98:02, DRB1*04:99, DRB1*07:01:01:01, DRB1*07:01:01:02, DRB1*07:01:01:03, DRB1*07:01:01:04, DRB1*07:01:02, DRB1*07:01:03, DRB1*07:01:04, DRB1*07:01:05, DRB1*07:01:06, DRB1*07:01:07, DRB1*07:01:08, DRB1*07:01:09, DRB1*07:01:10, DRB1*07:01:11, DRB1*07:01:12, DRB1*07:01:13, DRB1*07:01:14, DRB1*07:01:15, DRB1*07:01:16, DRB1*07:01:17, DRB1*07:01:18, DRB1*07:01:19, DRB1*07:01:20, DRB1*07:01:21, DRB1*07:01:22, DRB1*07:03, DRB1*07:04, DRB1*07:05, DRB1*07:06, DRB1*07:07, DRB1*07:08, DRB1*07:09, DRB1*07:100, DRB1*07: 101N, DRB1*07:10N, DRB1*07:11, DRB1*07:12, DRB1*07:13, DRB1*07:14, DRB1*07:15, DRB1*07:16, DRB1*07:17, DRB1*07:18, DRB1*07:19, DRB1*07:20, DRB1*07:21, DRB1*07:22, DRB1*07:23, DRB1*07:24, DRB1*07:25, DRB1*07:26N, DRB1*07:27, DRB1*07:28, DRB1*07:29, DRB1*07:30, DRB1*07:31, DRB1*07:32, DRB1*07:33, DRB1*07:34, DRB1*07:35, DRB1*07:36, DRB1*07:37, DRB1*07:38, DRB1*07:39, DRB1*07:40, DRB1*07:41, DRB1*07:42, DRB1*07:43, DRB1*07:44, DRB1*07:45, DRB1*07:46, DRB1*07:47, DRB1*07:48, DRB1*07:49, DRB1*07:50, DRB1*07:51, DRB1*07:52, DRB1*07:53, DRB1*07:54, DRB1*07:55, DRB1*07:56, DRB1*07:57, DRB1*07:58N, DRB1*07:59, DRB1*07:60, DRB1*07:61, DRB1*07:62, DRB1*07:63, DRB1*07:64, DRB1*07:65, DRB1*07:66, DRB1*07:67, DRB1*07:68N, DRB1*07:69, DRB1*07:70, DRB1*07:71, DRB1*07:72, DRB1*07:73, DRB1*07:74, DRB1*07:75, DRB1*07:76, DRB1*07:77, DRB1*07:78, DRB1*07:79, DRB1*07:80, DRB1*07:81, DRB1*07:82, DRB1*07:83, DRB1*07:84, DRB1*07:85, DRB1*07:86, DRB1*07:87N, DRB1*07:88, DRB1*07:89, DRB1*07:90, DRB1*07:91, DRB1*07:92, DRB1*07:93, DRB1*07:94, DRB1*07:95, DRB1*07:96, DRB1*07:97, DRB1*07:98, DRB1*07:99, DRB1*08:01: 01, DRB1*08:01:02, DRB1*08:01:04, DRB1*08:01:05, DRB1*08:01:06, DRB1*08:01:07, DRB1*08:02:01:01, DRB1*08:02:01:02, DRB1*08:02:02, DRB1*08:02:03, DRB1*08:02:04, DRB1*08:03:02:01, DRB1*08:03:02:02, DRB1*08:03:03, DRB1*08:03:04, DRB1*08:03:05, DRB1*08:03:06, DRB1*08:03:07, DRB1*08:03:08, DRB1*08:03:09, DRB1*08:04:01, DRB1*08:04:02, DRB1*08:04:03, DRB1*08:04:04, DRB1*08:04:05, DRB1*08:04:06, DRB1*08:04:07, DRB1*08:05, DRB1*08:06, DRB1*08:07, DRB1*08:08, DRB1*08:09, DRB1*08:10, DRB1*08:11, DRB1*08:12, DRB1*08:13, DRB1*08:14, DRB1*08:15, DRB1*08:16, DRB1*08:17, DRB1*08:18, DRB1*08:19, DRB1*08:20, DRB1*08:21, DRB1*08:22, DRB1*08:23, DRB1*08:24:01, DRB1*08: 24:02, DRB1*08:25, DRB1*08:26, DRB1*08:27,

DRB1*08:28, DRB1*08:29, DRB1*08:30:01, DRB1*08:30:02, DRB1*08:30:03, DRB1*08:31, DRB1*08:32, DRB1*08:33, DRB1*08:34, DRB1*08:35, DRB1*08:36:01, DRB1*08:36:02, DRB1*08:37, DRB1*08:38, DRB1*08:39, DRB1*08:40, DRB1*08:41, DRB1*08:42, DRB1*08:43, DRB1*08:44, DRB1*08:45:01, DRB1*08:45:02, DRB1*08:46, DRB1*08:47, DRB1*08:48, DRB1*08:49, DRB1*08:50, DRB1*08:51, DRB1*08:52, DRB1*08:53, DRB1*08:54, DRB1*08:55, DRB1*08:56, DRB1*08:57, DRB1*08:58, DRB1*08:59, DRB1*08:60N, DRB1*08:61, DRB1*08:62, DRB1*08:63, DRB1*08:64, DRB1*08:65, DRB1*08:66, DRB1*08:67, DRB1*08:68:01, DRB1*08:68:02, DRB1*08:69, DRB1*08:70, DRB1*08:71, DRB1*08:72, DRB1*08:73, DRB1*08:74, DRB1*08:75, DRB1*08:76, DRB1*08:77, DRB1*08:78N, DRB1*08:79, DRB1*08:80, DRB1*08:81, DRB1*08:82, DRB1*08:83, DRB1*08:84, DRB1*08:85, DRB1*08:86, DRB1*08:87, DRB1*08:88, DRB1*08:89N, DRB1*08:90, DRB1*09:01:02:01, DRB1*09:01:02:02, DRB1*09:01:03, DRB1*09:01:04, DRB1*09:01:05, DRB1*09:01:06, DRB1*09:01:07, DRB1*09:01:08, DRB1*09:01:09, DRB1*09:01:10, DRB1*09:01:11, DRB1*09:02:01, DRB1*09:02:02, DRB1*09:03, DRB1*09:04, DRB1*09:05, DRB1*09:06, DRB1*09:07, DRB1*09:08, DRB1*09:09, DRB1*09:10, DRB1*09:11, DRB1*09:12, DRB1*09:13, DRB1*09:14, DRB1*09:15, DRB1*09:16, DRB1*09:17, DRB1*09:18, DRB1*09:19, DRB1*09:20, DRB1*09:21, DRB1*09:22, DRB1*09:23, DRB1*09:24, DRB1*09:25, DRB1*09:26, DRB1*09:27, DRB1*09:28, DRB1*09:29, DRB1*09:30, DRB1*09:31, DRB1*09:32, DRB1*09:33, DRB1*09:34, DRB1*09:35, DRB1*09:36, DRB1*09:37N, DRB1*09:38, DRB1*09:39, DRB1*09:40, DRB1*10:01:01:01, DRB1*10:01:01:02, DRB1*10:01:01:03, DRB1*10:01:02, DRB1*10:01:03, DRB1*10:01:04, DRB1*10:01:05, DRB1*10:01:06, DRB1*10:01:07, DRB1*10:01:08, DRB1*10:01:09, DRB1*10:01:10, DRB1*10:01:11, DRB1*10:01:12, DRB1*10:02, DRB1*10:03, DRB1*10:04, DRB1*10:05, DRB1*10:06, DRB1*10:07, DRB1*10:08, DRB1*10:09, DRB1*10:10, DRB1*10:11, DRB1*10:12, DRB1*10:13, DRB1*10:14, DRB1*10:15, DRB1*10:16, DRB1*10:17, DRB1*10:18, DRB1*10:19, DRB1*10:20, DRB1*10:21, DRB1*10:22, DRB1*10:23, DRB1*10:24, DRB1*10:25, DRB1*10:26, DRB1*10:27, DRB1*10:28, DRB1*10:29, DRB1*10:30, DRB1*10:31, DRB1*10:32, DRB1*10:33, DRB1*11:01:01:01, DRB1*11:01:01:02, DRB1*11:01:01:03, DRB1*11:01:01:04, DRB1*11:01:02, DRB1*11:01:03, DRB1*11:01:04, DRB1*11:01:05, DRB1*11:01:06, DRB1*11:01:07, DRB1*11:01:08, DRB1*11:01:09, DRB1*11:01:10, DRB1*11:01:11, DRB1*11:01:12, DRB1*11:01:13, DRB1*11:01:14, DRB1*11:01:15, DRB1*11:01:16, DRB1*11:01:17, DRB1*11:01:18, DRB1*11:01:19, DRB1*11:01:20, DRB1*11:01:21, DRB1*11:01:22, DRB1*11:01:23, DRB1*11:01:24, DRB1*11:01:25, DRB1*11:01:26, DRB1*11:01:27, DRB1*11:01:28, DRB1*11:01:29, DRB1*11:01:30, DRB1*11:01:31, DRB1*11:01:32, DRB1*11:01:33, DRB1*11:02:01, DRB1*11:02:02, DRB1*11:02:03, DRB1*11:02:04, DRB1*11:02:05, DRB1*11:03:01, DRB1*11:03:02, DRB1*11:03:03, DRB1*11:03:04, DRB1*11:04:01, DRB1*11:04:02, DRB1*11:04:03, DRB1*11:04:04, DRB1*11:04:05, DRB1*11:04:06, DRB1*11:04:07, DRB1*11:04:08, DRB1*11:04:09, DRB1*11:04:10, DRB1*11:04:11, DRB1*11:04:12, DRB1*11:04:13, DRB1*11:04:14, DRB1*11:04:15, DRB1*11:04:16, DRB1*11:04:17, DRB1*11:04:18, DRB1*11:05, DRB1*11:06:01, DRB1*11:06:02, DRB1*11:06:03,

DRB1*11:07:01, DRB1*11:07:02, DRB1*11:08:01, DRB1*11:08:02, DRB1*11:08:03, DRB1*11:09, DRB1*11:100, DRB1*11:101:01, DRB1*11:101:02, DRB1*11:102:01, DRB1*11:102:02, DRB1*11:103:01, DRB1*11:103:02, DRB1*11:104, DRB1*11:105, DRB1*11:106, DRB1*11:107, DRB1*11:108, DRB1*11:109, DRB1*11:10:01, DRB1*11:10:02, DRB1*11:110, DRB1*11:111, DRB1*11:112, DRB1*11:113, DRB1*11:114, DRB1*11:115, DRB1*11:116, DRB1*11:117:01, DRB1*11:117:02, DRB1*11:118, DRB1*11:119, DRB1*11:11:01, DRB1*11:11:03, DRB1*11:120, DRB1*11:121, DRB1*11:122, DRB1*11:123, DRB1*11:124:01, DRB1*11:124:02, DRB1*11:125, DRB1*11:126, DRB1*11:127, DRB1*11:128, DRB1*11:129, DRB1*11:12:01, DRB1*11:12:02, DRB1*11:12:03, DRB1*11:130, DRB1*11:131, DRB1*11:132, DRB1*11:133, DRB1*11:134, DRB1*11:135, DRB1*11:136, DRB1*11:137, DRB1*11:138, DRB1*11:139, DRB1*11:13:01, DRB1*11:13:02, DRB1*11:140, DRB1*11:141, DRB1*11:142, DRB1*11:143, DRB1*11:144, DRB1*11:145, DRB1*11:146, DRB1*11:147:01, DRB1*11:147:02, DRB1*11:148, DRB1*11:149, DRB1*11:14:01, DRB1*11:14:02, DRB1*11:15, DRB1*11:150, DRB1*11:151, DRB1*11:152, DRB1*11:153, DRB1*11:154, DRB1*11:155, DRB1*11:156, DRB1*11:157, DRB1*11:158, DRB1*11:159, DRB1*11:16, DRB1*11:160, DRB1*11:161, DRB1*11:162, DRB1*11:163, DRB1*11:164, DRB1*11:165:01, DRB1*11:165:02, DRB1*11:166, DRB1*11:167, DRB1*11:168, DRB1*11:169N, DRB1*11:17, DRB1*11:170, DRB1*11:171, DRB1*11:172, DRB1*11:173, DRB1*11:174, DRB1*11:175, DRB1*11:176, DRB1*11:177, DRB1*11:178, DRB1*11:179, DRB1*11:18, DRB1*11:180, DRB1*11:181, DRB1*11:182, DRB1*11:183, DRB1*11:184, DRB1*11:185, DRB1*11:186, DRB1*11:187, DRB1*11:188, DRB1*11:189, DRB1*11:190, DRB1*11:191, DRB1*11:192, DRB1*11:193:01, DRB1*11:193:02, DRB1*11:194, DRB1*11:195, DRB1*11:196, DRB1*11:197, DRB1*11:198, DRB1*11:199, DRB1*11:19:01, DRB1*11:19:02, DRB1*11:19:03, DRB1*11:20, DRB1*11:200, DRB1*11:201, DRB1*11:202, DRB1*11:203, DRB1*11:204, DRB1*11:205, DRB1*11:206, DRB1*11:207, DRB1*11:208, DRB1*11:209, DRB1*11:21, DRB1*11:210, DRB1*11:211, DRB1*11:212, DRB1*11:213, DRB1*11:214, DRB1*11:215, DRB1*11:216, DRB1*11:217N, DRB1*11:218, DRB1*11:219, DRB1*11:22, DRB1*11:220, DRB1*11:221, DRB1*11:222, DRB1*11:223, DRB1*11:224, DRB1*11:225, DRB1*11:226, DRB1*11:227, DRB1*11:228, DRB1*11:229, DRB1*11:230, DRB1*11:231, DRB1*11:232, DRB1*11:233, DRB1*11:234, DRB1*11:235, DRB1*11:236, DRB1*11:237, DRB1*11:238, DRB1*11:239, DRB1*11:23:01, DRB1*11:23:02, DRB1*11:240, DRB1*11:241, DRB1*11:242, DRB1*11:243, DRB1*11:244, DRB1*11:245, DRB1*11:246N, DRB1*11:247, DRB1*11:248Q, DRB1*11:249, DRB1*11:24:01, DRB1*11:24:02, DRB1*11:25, DRB1*11:250N, DRB1*11:251, DRB1*11:252, DRB1*11:253, DRB1*11:254, DRB1*11:26, DRB1*11:27:01, DRB1*11:27:02, DRB1*11:27:03, DRB1*11:28:01, DRB1*11:28:02, DRB1*11:29:01, DRB1*11:29:02, DRB1*11:30, DRB1*11:31, DRB1*11:32, DRB1*11:33, DRB1*11:34, DRB1*11:35, DRB1*11:36, DRB1*11:37:01, DRB1*11:37:02, DRB1*11:38, DRB1*11:39, DRB1*11:40, DRB1*11:41, DRB1*11:42:01, DRB1*11:42:02, DRB1*11:43, DRB1*11:44, DRB1*11:45, DRB1*11:46:01, DRB1*11:46:02, DRB1*11:47, DRB1*11:48, DRB1*11:49:01, DRB1*11:49:02, DRB1*11:50,

DRB1*11:51, DRB1*11:52, DRB1*11:53, DRB1*11:54:
01, DRB1*11:54:02, DRB1*11:55, DRB1*11:56,
DRB1*11:57, DRB1*11:58:01, DRB1*11:58:02,
DRB1*11:59, DRB1*11:60, DRB1*11:61, DRB1*11:62:
01, DRB1*11:62:02, DRB1*11:63:01, DRB1*11:63:02,
DRB1*11:64, DRB1*11:65:01, DRB1*11:65:02,
DRB1*11:66:01, DRB1*11:66:02, DRB1*11:67,
DRB1*11:68, DRB1*11:69, DRB1*11:70, DRB1*11:72,
DRB1*11:73, DRB1*11:74:01, DRB1*11:74:02,
DRB1*11:75, DRB1*11:76, DRB1*11:77, DRB1*11:78,
DRB1*11:79, DRB1*11:80, DRB1*11:81, DRB1*11:82,
DRB1*11:83, DRB1*11:84:01, DRB1*11:84:02,
DRB1*11:84:03, DRB1*11:85, DRB1*11:86, DRB1*11:
87, DRB1*11:88, DRB1*11:89, DRB1*11:90, DRB1*11:
91, DRB1*11:92, DRB1*11:93, DRB1*11:94, DRB1*11:
95, DRB1*11:96, DRB1*11:97, DRB1*11:98, DRB1*11:
99, DRB1*12:01:01:01, DRB1*12:01:01:02, DRB1*12:01:
01:03, DRB1*12:01:01:04, DRB1*12:01:01:05, DRB1*12:
01:01:06, DRB1*12:01:02, DRB1*12:01:03, DRB1*12:01:
04, DRB1*12:01:05, DRB1*12:01:06, DRB1*12:01:07,
DRB1*12:01:08, DRB1*12:01:09, DRB1*12:02:01:01,
DRB1*12:02:01:02, DRB1*12:02:01:03, DRB1*12:02:01:
04, DRB1*12:02:02, DRB1*12:02:03, DRB1*12:02:04,
DRB1*12:02:05, DRB1*12:02:06, DRB1*12:02:07,
DRB1*12:02:08, DRB1*12:02:09, DRB1*12:03:02,
DRB1*12:03:03, DRB1*12:04, DRB1*12:05, DRB1*12:
06, DRB1*12:07, DRB1*12:08, DRB1*12:09, DRB1*12:
10, DRB1*12:11, DRB1*12:12, DRB1*12:13, DRB1*12:
14, DRB1*12:15, DRB1*12:16:01, DRB1*12:16:02,
DRB1*12:16:03, DRB1*12:17, DRB1*12:18, DRB1*12:
19, DRB1*12:20, DRB1*12:21, DRB1*12:22, DRB1*12:
23, DRB1*12:24N, DRB1*12:25, DRB1*12:26, DRB1*12:
27, DRB1*12:28, DRB1*12:29, DRB1*12:30, DRB1*12:
31N, DRB1*12:32, DRB1*12:33, DRB1*12:34, DRB1*12:
35, DRB1*12:36, DRB1*12:37, DRB1*12:38, DRB1*12:
39, DRB1*12:40, DRB1*12:41, DRB1*12:42, DRB1*12:
43, DRB1*12:44, DRB1*12:45, DRB1*12:46, DRB1*12:
47, DRB1*12:48, DRB1*12:49, DRB1*12:50, DRB1*12:
51, DRB1*12:52, DRB1*12:53, DRB1*12:54, DRB1*12:
55, DRB1*12:56, DRB1*12:57, DRB1*12:58, DRB1*12:
59, DRB1*12:60N, DRB1*12:61, DRB1*12:62, DRB1*12:
63, DRB1*12:64, DRB1*12:65, DRB1*12:66, DRB1*12:
67, DRB1*12:68, DRB1*12:69, DRB1*12:70, DRB1*12:
71, DRB1*12:72N, DRB1*12:73, DRB1*12:74N,
DRB1*12:75, DRB1*13:01:01:01, DRB1*13:01:01:02,
DRB1*13:01:02, DRB1*13:01:03, DRB1*13:01:04,
DRB1*13:01:05, DRB1*13:01:06, DRB1*13:01:07,
DRB1*13:01:08, DRB1*13:01:09, DRB1*13:01:10,
DRB1*13:01:11, DRB1*13:01:12, DRB1*13:01:13,
DRB1*13:01:14, DRB1*13:01:15, DRB1*13:01:16,
DRB1*13:01:17, DRB1*13:01:18, DRB1*13:01:19,
DRB1*13:01:20, DRB1*13:01:21, DRB1*13:01:22,
DRB1*13:01:23, DRB1*13:01:24, DRB1*13:01:25,
DRB1*13:01:26, DRB1*13:02:01:01, DRB1*13:02:01:02,
DRB1*13:02:01:03, DRB1*13:02:02, DRB1*13:02:03,
DRB1*13:02:04, DRB1*13:02:05, DRB1*13:02:06,
DRB1*13:02:07, DRB1*13:02:08, DRB1*13:02:09,
DRB1*13:02:10, DRB1*13:02:11, DRB1*13:02:12,
DRB1*13:02:13, DRB1*13:02:14, DRB1*13:02:15,
DRB1*13:02:16, DRB1*13:02:17, DRB1*13:03:01,
DRB1*13:03:02, DRB1*13:03:03, DRB1*13:03:04,
DRB1*13:03:05, DRB1*13:03:06, DRB1*13:03:07,
DRB1*13:03:08, DRB1*13:03:09, DRB1*13:04,
DRB1*13:05:01, DRB1*13:05:02, DRB1*13:05:03,
DRB1*13:06, DRB1*13:07:01, DRB1*13:07:02,
DRB1*13:08, DRB1*13:09, DRB1*13:10, DRB1*13:100,
DRB1*13:101, DRB1*13:102, DRB1*13:103, DRB1*13:

104, DRB1*13:105, DRB1*13:106, DRB1*13:107,
DRB1*13:108, DRB1*13:109, DRB1*13:110, DRB1*13:
111, DRB1*13:112, DRB1*13:113N, DRB1*13:114,
DRB1*13:115, DRB1*13:116, DRB1*13:117, DRB1*13:
118, DRB1*13:119, DRB1*13:11:01, DRB1*13:11:02,
DRB1*13:120, DRB1*13:121, DRB1*13:122, DRB1*13:
123, DRB1*13:124, DRB1*13:125, DRB1*13:126,
DRB1*13:127, DRB1*13:128, DRB1*13:129, DRB1*13:
12:01, DRB1*13:12:02, DRB1*13:12:03, DRB1*13:12:04,
DRB1*13:13, DRB1*13:130, DRB1*13:131, DRB1*13:
132, DRB1*13:133, DRB1*13:134, DRB1*13:135,
DRB1*13:136, DRB1*13:137N, DRB1*13:138, DRB1*13:
139, DRB1*13:140, DRB1*13:141, DRB1*13:142N,
DRB1*13:143, DRB1*13:144, DRB1*13:145, DRB1*13:
146, DRB1*13:147, DRB1*13:148, DRB1*13:149,
DRB1*13:14:01, DRB1*13:14:02, DRB1*13:14:03,
DRB1*13:15, DRB1*13:150, DRB1*13:151, DRB1*13:
152, DRB1*13:153, DRB1*13:154, DRB1*13:155,
DRB1*13:156, DRB1*13:157, DRB1*13:158, DRB1*13:
159, DRB1*13:16, DRB1*13:160, DRB1*13:161,
DRB1*13:162, DRB1*13:163, DRB1*13:164, DRB1*13:
165, DRB1*13:166, DRB1*13:167, DRB1*13:168,
DRB1*13:169, DRB1*13:17, DRB1*13:170, DRB1*13:
171:01, DRB1*13:171:02, DRB1*13:172, DRB1*13:173,
DRB1*13:174, DRB1*13:175, DRB1*13:176, DRB1*13:
177, DRB1*13:178, DRB1*13:179, DRB1*13:18,
DRB1*13:180, DRB1*13:181, DRB1*13:182, DRB1*13:
183, DRB1*13:184, DRB1*13:185N, DRB1*13:186,
DRB1*13:187, DRB1*13:188, DRB1*13:189, DRB1*13:
19, DRB1*13:190, DRB1*13:191, DRB1*13:192,
DRB1*13:193, DRB1*13:194, DRB1*13:195, DRB1*13:
196, DRB1*13:197, DRB1*13:198, DRB1*13:199,
DRB1*13:20, DRB1*13:200N, DRB1*13:201, DRB1*13:
202, DRB1*13:203, DRB1*13:204, DRB1*13:205,
DRB1*13:206, DRB1*13:207, DRB1*13:208, DRB1*13:
209, DRB1*13:210, DRB1*13:211, DRB1*13:212,
DRB1*13:213, DRB1*13:214, DRB1*13:215, DRB1*13:
216, DRB1*13:217, DRB1*13:218, DRB1*13:219,
DRB1*13:21:01, DRB1*13:21:02, DRB1*13:220,
DRB1*13:221, DRB1*13:222, DRB1*13:223, DRB1*13:
224, DRB1*13:225, DRB1*13:226, DRB1*13:227,
DRB1*13:228, DRB1*13:229, DRB1*13:22:01, DRB1*13:
22:02, DRB1*13:230, DRB1*13:231, DRB1*13:232,
DRB1*13:233, DRB1*13:234, DRB1*13:235, DRB1*13:
236, DRB1*13:237, DRB1*13:238, DRB1*13:239,
DRB1*13:23:01, DRB1*13:23:02, DRB1*13:24,
DRB1*13:240, DRB1*13:241, DRB1*13:242:01,
DRB1*13:242:02, DRB1*13:243, DRB1*13:244,
DRB1*13:245, DRB1*13:246, DRB1*13:247, DRB1*13:
248, DRB1*13:249N, DRB1*13:25, DRB1*13:250,
DRB1*13:251, DRB1*13:252N, DRB1*13:253, DRB1*13:
254, DRB1*13:255N, DRB1*13:256, DRB1*13:257,
DRB1*13:258, DRB1*13:259, DRB1*13:260, DRB1*13:
261, DRB1*13:262, DRB1*13:263, DRB1*13:264,
DRB1*13:265, DRB1*13:266, DRB1*13:267, DRB1*13:
268N, DRB1*13:269, DRB1*13:26:01, DRB1*13:26:02,
DRB1*13:27, DRB1*13:270, DRB1*13:271, DRB1*13:
272, DRB1*13:273, DRB1*13:274, DRB1*13:275,
DRB1*13:276, DRB1*13:277, DRB1*13:278Q, DRB1*13:
279, DRB1*13:28:01, DRB1*13:28:02, DRB1*13:29,
DRB1*13:30, DRB1*13:31, DRB1*13:32, DRB1*13:33:
01, DRB1*13:33:02, DRB1*13:33:03, DRB1*13:34,
DRB1*13:35, DRB1*13:36, DRB1*13:37, DRB1*13:38,
DRB1*13:39, DRB1*13:40, DRB1*13:41, DRB1*13:42,
DRB1*13:43, DRB1*13:44, DRB1*13:45, DRB1*13:46,
DRB1*13:47, DRB1*13:48, DRB1*13:49, DRB1*13:50:
01, DRB1*13:50:02, DRB1*13:50:03, DRB1*13:51,

DRB1*13:52, DRB1*13:53, DRB1*13:54, DRB1*13:55, DRB1*13:56, DRB1*13:57, DRB1*13:58, DRB1*13:59, DRB1*13:60, DRB1*13:61:01, DRB1*13:61:02, DRB1*13:62, DRB1*13:63, DRB1*13:64, DRB1*13:65, DRB1*13:66:01, DRB1*13:66:02, DRB1*13:67, DRB1*13:68, DRB1*13:69, DRB1*13:70, DRB1*13:71, DRB1*13:72, DRB1*13:73, DRB1*13:74, DRB1*13:75, DRB1*13:76, DRB1*13:77, DRB1*13:78, DRB1*13:79, DRB1*13:80, DRB1*13:81, DRB1*13:82, DRB1*13:83, DRB1*13:84, DRB1*13:85, DRB1*13:86, DRB1*13:87, DRB1*13:88, DRB1*13:89:01, DRB1*13:89:02, DRB1*13:90, DRB1*13:91, DRB1*13:92, DRB1*13:93, DRB1*13:94:01, DRB1*13:94:02, DRB1*13:95, DRB1*13:96:01, DRB1*13:96:02, DRB1*13:97:01, DRB1*13:97:02, DRB1*13:98, DRB1*13:99, DRB1*14: 01:01, DRB1*14:01:02, DRB1*14:01:03, DRB1*14:01:04, DRB1*14:02:01:01, DRB1*14:02:01:02, DRB1*14:02:02, DRB1*14:02:03, DRB1*14:02:04, DRB1*14:02:05, DRB1*14:02:06, DRB1*14:02:07, DRB1*14:03:01, DRB1*14:03:02, DRB1*14:04:01, DRB1*14:04:02, DRB1*14:04:03, DRB1*14:04:04, DRB1*14:04:05, DRB1*14:04:06, DRB1*14:05:01:01, DRB1*14:05:01:02, DRB1*14:05:02, DRB1*14:05:03, DRB1*14:05:04, DRB1*14:06:01, DRB1*14:06:02, DRB1*14:06:03, DRB1*14:06:04, DRB1*14:07:01, DRB1*14:07:02, DRB1*14:08, DRB1*14:09, DRB1*14:10, DRB1*14:100, DRB1*14:101, DRB1*14:102, DRB1*14:103, DRB1*14: 104, DRB1*14:105, DRB1*14:106, DRB1*14:107, DRB1*14:108, DRB1*14:109, DRB1*14:11, DRB1*14: 110, DRB1*14:111, DRB1*14:112, DRB1*14:113, DRB1*14:114, DRB1*14:115, DRB1*14:116, DRB1*14: 117, DRB1*14:118, DRB1*14:119, DRB1*14:120, DRB1*14:121, DRB1*14:122, DRB1*14:123, DRB1*14: 124, DRB1*14:125, DRB1*14:126:01, DRB1*14:126:02, DRB1*14:127:01, DRB1*14:127:02, DRB1*14:128, DRB1*14:129, DRB1*14:12:01, DRB1*14:12:02, DRB1*14:13, DRB1*14:130, DRB1*14:131, DRB1*14: 132, DRB1*14:133, DRB1*14:134, DRB1*14:135, DRB1*14:136, DRB1*14:137N, DRB1*14:138, DRB1*14: 139, DRB1*14:14, DRB1*14:140, DRB1*14:141, DRB1*14:142, DRB1*14:143, DRB1*14:144, DRB1*14: 145, DRB1*14:146, DRB1*14:147, DRB1*14:148, DRB1*14:149, DRB1*14:15, DRB1*14:150, DRB1*14: 151, DRB1*14:152N, DRB1*14:153, DRB1*14:154, DRB1*14:155, DRB1*14:156, DRB1*14:157, DRB1*14: 158, DRB1*14:159, DRB1*14:16, DRB1*14:160, DRB1*14:161, DRB1*14:162, DRB1*14:163, DRB1*14: 164, DRB1*14:165, DRB1*14:166N, DRB1*14:167, DRB1*14:168, DRB1*14:169, DRB1*14:17, DRB1*14: 170, DRB1*14:171, DRB1*14:172, DRB1*14:173, DRB1*14:174, DRB1*14:175, DRB1*14:176, DRB1*14: 177, DRB1*14:178, DRB1*14:179, DRB1*14:18, DRB1*14:180, DRB1*14:181, DRB1*14:182, DRB1*14: 183, DRB1*14:184, DRB1*14:185, DRB1*14:186, DRB1*14:187, DRB1*14:188N, DRB1*14:189, DRB1*14: 19, DRB1*14:190, DRB1*14:191, DRB1*14:192, DRB1*14:193, DRB1*14:194, DRB1*14:195N, DRB1*14: 196, DRB1*14:197N, DRB1*14:198, DRB1*14:199, DRB1*14:20, DRB1*14:200, DRB1*14:201, DRB1*14: 202, DRB1*14:203, DRB1*14:204, DRB1*14:205, DRB1*14:206, DRB1*14:207, DRB1*14:208, DRB1*14: 209, DRB1*14:21, DRB1*14:210Q, DRB1*14:211, DRB1*14:22, DRB1*14:23:01, DRB1*14:23:02, DRB1*14:23:03, DRB1*14:23:04, DRB1*14:24, DRB1*14:25:01, DRB1*14:25:02, DRB1*14:26, DRB1*14:27:01, DRB1*14:27:02, DRB1*14:28, DRB1*14:29, DRB1*14:30, DRB1*14:31, DRB1*14:32:

01, DRB1*14:32:02, DRB1*14:32:03, DRB1*14:33, DRB1*14:34, DRB1*14:35, DRB1*14:36, DRB1*14:37, DRB1*14:38:01, DRB1*14:38:02, DRB1*14:39, DRB1*14:40, DRB1*14:41, DRB1*14:42, DRB1*14:43, DRB1*14:44:01, DRB1*14:44:02, DRB1*14:44:03, DRB1*14:45, DRB1*14:46, DRB1*14:47, DRB1*14:48, DRB1*14:49, DRB1*14:50, DRB1*14:51, DRB1*14:52, DRB1*14:53, DRB1*14:54:01:01, DRB1*14:54:01:02, DRB1*14:54:01:03, DRB1*14:54:01:04, DRB1*14:54:02, DRB1*14:54:03, DRB1*14:54:04, DRB1*14:54:05, DRB1*14:54:06, DRB1*14:54:07, DRB1*14:55, DRB1*14:56, DRB1*14:57, DRB1*14:58, DRB1*14:59, DRB1*14:60, DRB1*14:61, DRB1*14:62, DRB1*14:63, DRB1*14:64, DRB1*14:65, DRB1*14:67, DRB1*14:68: 01, DRB1*14:68:02, DRB1*14:69, DRB1*14:70, DRB1*14:71, DRB1*14:72, DRB1*14:73, DRB1*14:74, DRB1*14:75, DRB1*14:76, DRB1*14:77, DRB1*14:78, DRB1*14:79, DRB1*14:80, DRB1*14:81, DRB1*14:82, DRB1*14:83, DRB1*14:84, DRB1*14:85, DRB1*14:86, DRB1*14:87, DRB1*14:88, DRB1*14:89, DRB1*14:90, DRB1*14:91, DRB1*14:92N, DRB1*14:93, DRB1*14:94, DRB1*14:95, DRB1*14:96, DRB1*14:97, DRB1*14:98, DRB1*14:99, DRB1*15:01:01:01, DRB1*15:01:01:02, DRB1*15:01:01:03, DRB1*15:01:01:04, DRB1*15:01:01: 05, DRB1*15:01:02, DRB1*15:01:03, DRB1*15:01:04, DRB1*15:01:05, DRB1*15:01:06, DRB1*15:01:07, DRB1*15:01:08, DRB1*15:01:09, DRB1*15:01:10, DRB1*15:01:11, DRB1*15:01:12, DRB1*15:01:13, DRB1*15:01:14, DRB1*15:01:15, DRB1*15:01:16, DRB1*15:01:17, DRB1*15:01:18, DRB1*15:01:19, DRB1*15:01:20, DRB1*15:01:21, DRB1*15:01:22, DRB1*15:01:23, DRB1*15:01:24, DRB1*15:01:25, DRB1*15:01:26, DRB1*15:01:27, DRB1*15:01:28, DRB1*15:01:29, DRB1*15:01:30, DRB1*15:01:31, DRB1*15:01:32, DRB1*15:01:33, DRB1*15:01:34, DRB1*15:01:35, DRB1*15:01:36, DRB1*15:01:37, DRB1*15:01:38, DRB1*15:01:39, DRB1*15:01:40, DRB1*15:01:41, DRB1*15:02:01:01, DRB1*15:02:01:02, DRB1*15:02:01:03, DRB1*15:02:02, DRB1*15:02:03, DRB1*15:02:04, DRB1*15:02:05, DRB1*15:02:06, DRB1*15:02:07, DRB1*15:02:08, DRB1*15:02:09, DRB1*15:02:10, DRB1*15:02:11, DRB1*15:02:12, DRB1*15:02:13, DRB1*15:02:14, DRB1*15:02:15, DRB1*15:02:16, DRB1*15:02:17, DRB1*15:02:18, DRB1*15:02:19, DRB1*15:03:01:01, DRB1*15:03:01:02, DRB1*15:03:01:03, DRB1*15:03:02, DRB1*15:03:03, DRB1*15:03:04, DRB1*15:04, DRB1*15:05, DRB1*15: 06:01, DRB1*15:06:02, DRB1*15:06:03, DRB1*15:06:04, DRB1*15:07:01, DRB1*15:07:02, DRB1*15:07:03, DRB1*15:08, DRB1*15:09, DRB1*15:10, DRB1*15:100, DRB1*15:101, DRB1*15:102, DRB1*15:103, DRB1*15: 104:01, DRB1*15:104:02, DRB1*15:104:03, DRB1*15: 105:01, DRB1*15:105:02, DRB1*15:106, DRB1*15:107, DRB1*15:108, DRB1*15:109, DRB1*15:110, DRB1*15: 111, DRB1*15:112, DRB1*15:113N, DRB1*15:114, DRB1*15:115N, DRB1*15:116, DRB1*15:117, DRB1*15: 118, DRB1*15:119, DRB1*15:11:01, DRB1*15:11:02, DRB1*15:12, DRB1*15:120, DRB1*15:121, DRB1*15: 122, DRB1*15:123, DRB1*15:124, DRB1*15:125, DRB1*15:126, DRB1*15:127, DRB1*15:128, DRB1*15: 129N, DRB1*15:13, DRB1*15:130, DRB1*15:131, DRB1*15:132, DRB1*15:133, DRB1*15:134N, DRB1*15: 135, DRB1*15:136, DRB1*15:137N, DRB1*15:138N, DRB1*15:139, DRB1*15:14, DRB1*15:140, DRB1*15: 141, DRB1*15:142, DRB1*15:143, DRB1*15:144, DRB1*15:145, DRB1*15:146, DRB1*15:147, DRB1*15: 148N, DRB1*15:149, DRB1*15:150, DRB1*15:151,

DRB1*15:152, DRB1*15:153, DRB1*15:154N, DRB1*15:
155, DRB1*15:156, DRB1*15:157, DRB1*15:158,
DRB1*15:159N, DRB1*15:15:01, DRB1*15:15:02,
DRB1*15:15:03, DRB1*15:16, DRB1*15:160, DRB1*15:
161, DRB1*15:162, DRB1*15:163N, DRB1*15:164Q,
DRB1*15:165, DRB1*15:166, DRB1*15:167, DRB1*15:
168, DRB1*15:169, DRB1*15:170, DRB1*15:17N,
DRB1*15:18, DRB1*15:19, DRB1*15:20, DRB1*15:21,
DRB1*15:22, DRB1*15:23, DRB1*15:24, DRB1*15:25,
DRB1*15:26, DRB1*15:27, DRB1*15:28, DRB1*15:29,
DRB1*15:30, DRB1*15:31:01, DRB1*15:31:02,
DRB1*15:32, DRB1*15:33, DRB1*15:34, DRB1*15:35,
DRB1*15:36, DRB1*15:37:01, DRB1*15:37:02,
DRB1*15:38, DRB1*15:39, DRB1*15:40, DRB1*15:41,
DRB1*15:42, DRB1*15:43, DRB1*15:44, DRB1*15:45,
DRB1*15:46, DRB1*15:47, DRB1*15:48, DRB1*15:49,
DRB1*15:50N, DRB1*15:51, DRB1*15:52, DRB1*15:53,
DRB1*15:54, DRB1*15:55, DRB1*15:56, DRB1*15:57,
DRB1*15:58, DRB1*15:59, DRB1*15:60, DRB1*15:61,
DRB1*15:62, DRB1*15:63, DRB1*15:64, DRB1*15:65,
DRB1*15:66:01, DRB1*15:66:02, DRB1*15:67,
DRB1*15:68, DRB1*15:69, DRB1*15:70, DRB1*15:71,
DRB1*15:72, DRB1*15:73, DRB1*15:74, DRB1*15:75,
DRB1*15:76, DRB1*15:77, DRB1*15:78, DRB1*15:79,
DRB1*15:80N, DRB1*15:81, DRB1*15:82, DRB1*15:83,
DRB1*15:84, DRB1*15:85, DRB1*15:86, DRB1*15:87,
DRB1*15:88, DRB1*15:89, DRB1*15:90, DRB1*15:91,
DRB1*15:92, DRB1*15:93, DRB1*15:94, DRB1*15:95,
DRB1*15:96, DRB1*15:97, DRB1*15:98, DRB1*15:99,
DRB1*16:01:01, DRB1*16:01:02, DRB1*16:01:03,
DRB1*16:01:04, DRB1*16:01:05, DRB1*16:01:06,
DRB1*16:01:07, DRB1*16:01:08, DRB1*16:01:09,
DRB1*16:01:10, DRB1*16:01:11, DRB1*16:01:12,
DRB1*16:01:13, DRB1*16:01:14, DRB1*16:01:15,
DRB1*16:01:16, DRB1*16:02:01:01, DRB1*16:02:01:02,
DRB1*16:02:01:03, DRB1*16:02:02, DRB1*16:02:03,
DRB1*16:02:04, DRB1*16:02:05, DRB1*16:02:06,
DRB1*16:02:07, DRB1*16:02:08, DRB1*16:03,
DRB1*16:04:01, DRB1*16:04:02, DRB1*16:05:01,
DRB1*16:05:02, DRB1*16:07, DRB1*16:08, DRB1*16:
09:01, DRB1*16:09:02, DRB1*16:10:01, DRB1*16:10:02,
DRB1*16:11, DRB1*16:12, DRB1*16:13N, DRB1*16:14,
DRB1*16:15, DRB1*16:16, DRB1*16:17, DRB1*16:18,
DRB1*16:19, DRB1*16:20, DRB1*16:21N, DRB1*16:22,
DRB1*16:23, DRB1*16:24, DRB1*16:25, DRB1*16:26,
DRB1*16:27, DRB1*16:28, DRB1*16:29, DRB1*16:30,
DRB1*16:31, DRB1*16:32, DRB1*16:33, DRB1*16:34,
DRB1*16:35, DRB1*16:36, DRB1*16:37, DRB1*16:38:
01, DRB1*16:38:02, DRB1*16:39, DRB1*16:40,
DRB1*16:41N, DRB1*16:42, DRB1*16:43, DRB1*16:44,
DRB1*16:45, DRB1*16:46, DRB1*16:47, DRB1*16:48,
DRB1*16:49, DRB1*16:50, DRB1*16:51, DRB1*16:52,
DRB1*16:53, DRB1*16:54, DRB1*16:55N, DRB1*16:56,
DRB3*01:01:02:01, DRB3*01:01:02:02, DRB3*01:01:02:
03, DRB3*01:01:03, DRB3*01:01:04, DRB3*01:01:05,
DRB3*01:01:06, DRB3*01:01:07, DRB3*01:01:08,
DRB3*01:01:09, DRB3*01:01:10, DRB3*01:02,
DRB3*01:03, DRB3*01:04, DRB3*01:05, DRB3*01:06,
DRB3*01:07, DRB3*01:08, DRB3*01:09, DRB3*01:10,
DRB3*01:11, DRB3*01:12, DRB3*01:13, DRB3*01:14,
DRB3*01:15, DRB3*01:16, DRB3*01:17, DRB3*01:18,
DRB3*01:19, DRB3*01:20, DRB3*01:21, DRB3*01:22,
DRB3*01:23, DRB3*01:24, DRB3*01:25, DRB3*01:26N,
DRB3*01:27, DRB3*01:28, DRB3*01:29, DRB3*01:30,
DRB3*01:31, DRB3*01:32, DRB3*01:33, DRB3*01:34,
DRB3*01:35, DRB3*01:36, DRB3*01:37, DRB3*01:38,
DRB3*01:39, DRB3*01:40:01N, DRB3*01:40:02N,

DRB3*01:41, DRB3*01:42, DRB3*01:43, DRB3*01:44,
DRB3*01:45, DRB3*01:46, DRB3*01:47, DRB3*01:48,
DRB3*01:49, DRB3*01:50, DRB3*01:51, DRB3*01:52,
DRB3*01:53, DRB3*01:54, DRB3*01:55, DRB3*01:56,
DRB3*01:57, DRB3*01:58, DRB3*01:59, DRB3*01:60,
DRB3*01:61, DRB3*01:62, DRB3*02:01, DRB3*02:02:
01:01, DRB3*02:02:01:02, DRB3*02:02:01:03, DRB3*02:
02:01:04, DRB3*02:02:02, DRB3*02:02:03, DRB3*02:02:
04, DRB3*02:02:05, DRB3*02:02:06, DRB3*02:02:07,
DRB3*02:02:08, DRB3*02:02:09, DRB3*02:02:10,
DRB3*02:02:11, DRB3*02:02:12, DRB3*02:02:13,
DRB3*02:02:14, DRB3*02:02:15, DRB3*02:02:16,
DRB3*02:02:17, DRB3*02:02:18, DRB3*02:02:19,
DRB3*02:02:20, DRB3*02:02:21, DRB3*02:03,
DRB3*02:04, DRB3*02:05, DRB3*02:06, DRB3*02:07,
DRB3*02:08, DRB3*02:09, DRB3*02:10, DRB3*02:11,
DRB3*02:12, DRB3*02:13, DRB3*02:14, DRB3*02:15,
DRB3*02:16, DRB3*02:17, DRB3*02:18, DRB3*02:19,
DRB3*02:20, DRB3*02:21, DRB3*02:22:01, DRB3*02:
22:02, DRB3*02:23, DRB3*02:24, DRB3*02:25,
DRB3*02:26, DRB3*02:27, DRB3*02:28, DRB3*02:29N,
DRB3*02:30, DRB3*02:31:01, DRB3*02:31:02,
DRB3*02:32, DRB3*02:33, DRB3*02:34, DRB3*02:35,
DRB3*02:36, DRB3*02:37, DRB3*02:38, DRB3*02:39,
DRB3*02:40, DRB3*02:41, DRB3*02:42, DRB3*02:43,
DRB3*02:44, DRB3*02:45, DRB3*02:46, DRB3*02:47,
DRB3*02:48, DRB3*02:49, DRB3*02:50, DRB3*02:51,
DRB3*02:52, DRB3*02:53, DRB3*02:54, DRB3*02:55N,
DRB3*02:56, DRB3*02:57, DRB3*02:58, DRB3*02:59,
DRB3*02:60, DRB3*02:61Q, DRB3*02:62, DRB3*02:63,
DRB3*02:64, DRB3*02:65, DRB3*02:66, DRB3*02:67N,
DRB3*02:68, DRB3*02:69, DRB3*02:70, DRB3*02:71,
DRB3*02:72, DRB3*02:73, DRB3*02:74, DRB3*02:75,
DRB3*02:76, DRB3*02:77, DRB3*02:78, DRB3*02:79,
DRB3*02:80N, DRB3*02:81, DRB3*02:82, DRB3*02:83,
DRB3*02:84, DRB3*02:85, DRB3*02:86, DRB3*02:87,
DRB3*02:88, DRB3*02:89, DRB3*02:90, DRB3*02:91,
DRB3*02:92, DRB3*02:93, DRB3*02:94, DRB3*02:95N,
DRB3*03:01:01:01, DRB3*03:01:01:02, DRB3*03:01:02,
DRB3*03:01:03, DRB3*03:01:04, DRB3*03:01:05,
DRB3*03:01:06, DRB3*03:01:07, DRB3*03:02,
DRB3*03:03, DRB3*03:04, DRB3*03:05, DRB3*03:06,
DRB3*03:07, DRB3*03:08, DRB3*03:09, DRB3*03:10,
DRB3*03:11, DRB3*03:12, DRB3*03:13, DRB3*03:14,
DRB3*03:15, DRB3*03:16, DRB3*03:17, DRB3*03:18,
DRB3*03:19, DRB3*03:20, DRB3*03:21, DRB3*03:22,
DRB3*03:23, DRB3*03:24, DRB3*03:25, DRB4*01:01:
01:01, DRB4*01:01:02, DRB4*01:01:03, DRB4*01:01:04,
DRB4*01:01:05, DRB4*01:01:06, DRB4*01:02,
DRB4*01:03:01:01, DRB4*01:03:01:02N, DRB4*01:03:
01:03, DRB4*01:03:01:04, DRB4*01:03:01:05, DRB4*01:
03:01:06, DRB4*01:03:01:07, DRB4*01:03:01:08,
DRB4*01:03:01:09, DRB4*01:03:01:10, DRB4*01:03:01:
11, DRB4*01:03:02, DRB4*01:03:03, DRB4*01:03:04,
DRB4*01:03:05, DRB4*01:03:06, DRB4*01:03:07,
DRB4*01:03:08, DRB4*01:03:09, DRB4*01:03:10,
DRB4*01:03:11, DRB4*01:04, DRB4*01:05, DRB4*01:
06, DRB4*01:07:01, DRB4*01:07:02, DRB4*01:08,
DRB4*01:09, DRB4*01:10, DRB4*01:11, DRB4*01:12,
DRB4*01:13, DRB4*01:14, DRB4*01:15, DRB4*01:16N,
DRB4*01:17, DRB4*01:18, DRB4*01:19, DRB4*01:20,
DRB4*01:21, DRB4*01:22, DRB4*01:23, DRB4*01:24,
DRB4*01:25, DRB4*01:26, DRB4*01:27, DRB4*01:28,
DRB4*01:29, DRB4*01:30, DRB4*01:31, DRB4*01:32,
DRB4*01:33, DRB4*01:34, DRB4*01:35, DRB4*01:36,
DRB4*01:37, DRB4*01:38N, DRB4*01:39, DRB4*01:40,
DRB4*01:41, DRB4*01:42, DRB4*01:43, DRB4*01:44,

DRB4*01:45, DRB4*01:46, DRB4*01:47, DRB4*01:48, DRB4*01:49, DRB4*01:50, DRB4*01:51, DRB4*01:52, DRB4*01:53, DRB4*01:54N, DRB4*01:55, DRB4*01: 56N, DRB4*01:57N, DRB4*01:58, DRB4*01:59, DRB4*01:60, DRB4*01:61N, DRB4*01:62, DRB4*01:63, DRB4*01:64, DRB4*01:65N, DRB4*01:66, DRB4*01:67, DRB4*01:68, DRB4*01:69, DRB4*01:70, DRB4*01:71N, DRB4*01:72, DRB4*01:73, DRB4*01:74, DRB4*01:75, DRB4*01:76, DRB4*01:77, DRB4*01:78, DRB4*01:79, DRB4*01:80N, DRB4*01:81, DRB4*01:82, DRB4*01:83, DRB4*01:84N, DRB4*01:85, DRB4*01:86, DRB4*01:87, DRB4*01:88, DRB4*01:89, DRB4*01:90, DRB4*01:91, DRB4*01:92, DRB4*01:93, DRB4*02:01N, DRB5*01:01: 01:01, DRB5*01:01:01:02, DRB5*01:01:02, DRB5*01:01: 03, DRB5*01:01:04, DRB5*01:02, DRB5*01:03, DRB5*01:04, DRB5*01:05, DRB5*01:06, DRB5*01:07, DRB5*01:08N, DRB5*01:09, DRB5*01:10N, DRB5*01: 11, DRB5*01:12, DRB5*01:13, DRB5*01:14, DRB5*01: 15, DRB5*01:16, DRB5*01:17, DRB5*01:18, DRB5*01: 19, DRB5*01:20, DRB5*01:21, DRB5*01:22:01, DRB5*01:22:02, DRB5*01:23, DRB5*01:24, DRB5*01: 25, DRB5*01:26, DRB5*01:27N, DRB5*01:28, DRB5*01: 29, DRB5*01:30, DRB5*01:31, DRB5*01:32, DRB5*01: 33, DRB5*01:34, DRB5*01:35, DRB5*01:36, DRB5*01: 37, DRB5*01:38, DRB5*01:39, DRB5*01:40, DRB5*01: 41, DRB5*01:42, DRB5*01:43, DRB5*01:44, DRB5*01: 45, DRB5*01:46, DRB5*01:47, DRB5*01:48N, DRB5*01: 49N, DRB5*01:50, DRB5*01:51, DRB5*01:52N, DRB5*01:53N, DRB5*01:54, DRB5*01:55, DRB5*02:02: 01, DRB5*02:02:02, DRB5*02:02:03, DRB5*02:03, DRB5*02:04, DRB5*02:05, DRB5*02:06, DRB5*02:07, DRB5*02:08, DRB5*02:09, DRB5*02:10, DRB5*02:11, DRB5*02:12, DRB5*02:13, DRB5*02:14, DRB5*02:15, DRB5*02:16, DRB5*02:17, DRB5*02:18, DRB5*02:19N, DRB5*02:20, DRB5*02:21, DRB5*02:22, DRB5*02:23, DRB5*02:24 and any combination thereof.

In some aspects, the HLA class II molecule is a monomer. In some aspects, the HLA class II molecule is a dimer. In some aspects, the HLA class II molecule is a multimer. In some aspects, the HLA class II molecule is a trimer. In some aspects, the HLA class II molecule is a tetramer. In some aspects, the HLA class II molecule is a pentamer.

Certain aspects of the present disclosure are directed to antigen presenting cells (APCs) comprising any HLA class II molecule disclosed herein. In certain aspects, the APC expressed the HLA class II molecule on the surface of the APC. In certain aspects, the APC comprises more than one HLA class II molecule disclosed herein.

II.E. Vaccines

Certain aspects of the present disclosure a cancer vaccine comprising a peptide comprising an amino acid sequence as set forth in SEQ ID NO: 13. In some aspects, the cancer vaccine comprises a peptide that consists of the amino acid sequence set forth in SEQ ID NO: 13. In some aspects, the vaccine further comprises one or more excipient. In some aspects, the vaccine further comprises one or more additional peptides. In some aspects, the one or more additional peptides comprise one or more additional epitopes.

III. Methods of the Disclosure

Certain aspects of the present disclosure are directed to methods of treating a cancer in a subject in need thereof. Other aspects of the present disclosure are directed to methods of engineering an antigen-targeting cell. Other aspects of the present disclosure are directed to methods of enriching a target population of T cells obtained from a human subject.

III.A. Methods of Treating Cancer

Certain aspects of the present disclosure are directed to methods of treating a cancer in a subject in need thereof, comprising administering to the subject a nucleic acid molecule disclosed herein, a recombinant TCR disclosed herein, a bispecific TCR disclosed herein, an epitope disclosed herein, or an HLA class II molecule disclosed herein, or a vector or cell comprising any of the above.

In some aspects, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some aspects, the cancer melanoma.

In some aspects, the cancer is relapsed. In some aspects, the cancer is refractory. In some aspects, the cancer is advanced. In some aspects, the cancer is metastatic.

In some aspects, the methods disclosed herein treat a cancer in a subject. In some aspects, the methods disclosed herein reduce the severity of one or more symptom of the cancer. In some aspects, the methods disclosed herein reduce the size or number of a tumor derived from the cancer. In some aspects, the methods disclosed herein increase the overall survival of the subject, relative to a subject not provided the methods disclosed herein. In some aspects, the methods disclosed herein increase the progressive-free survival of the subject, relative to a subject not provided the methods disclosed herein. In some aspects, the methods disclosed herein lead to a partial response in the subject. In some aspects, the methods disclosed herein lead to a complete response in the subject.

In some aspects, the methods disclosed herein comprise treating a cancer in a subject in need thereof, comprising administering to the subject a cell described herein, wherein the cell comprises a nucleic acid molecule disclosed herein, a vector disclosed herein, a recombinant TCR disclosed herein, and/or a bispecific antibody disclosed herein. In some aspects, the cell is a T cell. In some aspects, the cell is a cell that is modified to express CD4.

In some aspects, the cell, e.g., a T cell, is obtained from the subject. In some aspects, the cell, e.g., a T cell, is obtained from a donor other than the subject.

In some aspects, the subject is preconditioned prior to administering the cells. The preconditioning can comprise any substance that promotes T cell function and/or survival. In some aspects, the preconditioning comprises administering to the subject a chemotherapy, a cytokine, a protein, a small molecule, or any combination thereof. In some aspects, the preconditioning comprises administering an interleukin. In some aspects, the preconditioning comprises administering IL-2, IL-4, IL-7, IL-9, IL-15, IL-21, or any combination thereof. In some aspects, the preconditioning comprises administering cyclophosphamide, fludarabine, or both. In some aspects, the preconditioning comprises administering vitamin C, an AKT inhibitor, ATRA (vesanoid, tretinoin), rapamycin, or any combination thereof.

III.B. Methods of Engineering an Antigen-Targeting Cell

Certain aspects of the present disclosure are directed to methods of engineering an antigen-targeting cell. In some aspects, the antigen is a MUC5AC antigen. In some aspects, the method comprises transducing a cell with a nucleic acid molecule disclosed herein or a vector disclosed herein. The cell can be any cell described herein. In some aspects, the cell is a T cell described herein. In some aspects, the cell is a cell that is modified to express CD4, as described herein. In some aspects, the cell, e.g., the T cell, is obtained from a subject in need of a T cell therapy. In some aspects, the cell is obtained from a donor other than the subject in need of the T cell therapy. In some aspects, the cell is a T cell or a natural killer cell.

III.C. Methods of Enriching a Target Population of T Cells

Certain aspects of the present disclosure are directed to methods of enriching a target population of T cells obtained from a human subject. In some aspects, the method comprises contacting the T cells with an HLA class II molecule disclosed herein. In some aspects, the method comprises contacting the T cells with an APC disclosed herein. In some aspects, following the contacting, the enriched population of T cells comprises a higher number of T cells capable of binding the HLA class II molecule relative to the number of T cells capable of binding the HLA class II molecule prior to the contacting.

In some aspects, the method comprises contacting the T cells in vitro with a peptide, wherein the peptide comprises the amino acid sequence set forth in SEQ ID NO: 13. In some aspects, the method comprises contacting the T cells in vitro with a peptide, wherein the peptide consists of the amino acid sequence set forth in SEQ ID NO: 13. In some aspects, following the contacting, the enriched population of T cells comprises a higher number of T cells capable of binding the HLA class II molecule relative to the number of T cells capable of binding the HLA class II molecule prior to the contacting.

Some aspects of the present disclosure are directed to a method of selecting a T cell capable of targeting a tumor cell. In some aspects, the method comprises contacting a population of isolated T cells in vitro with a peptide, wherein the peptide consists of an amino acid sequence as set forth in SEQ ID NO: 13. In some aspects, the T cells are obtained from a human subject.

The T cells obtained from the human subject can be any T cells disclosed herein. In some aspects, the T cells obtained from the human subject are tumor infiltrating lymphocytes (TIL).

In some aspects, the method further comprises administering to the human subject the enriched T cells. In some aspects, the subject is preconditioned prior to receiving the T cells, as described herein.

All of the various aspects, aspects, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1— Methods

Cells

Peripheral mononuclear cells were obtained via density gradient centrifugation (Ficoll-Paque PLUS, GE Healthcare Life Sciences, Marlborough, MA). The K562 cell line is an erythroleukemic cell line with defective HLA class I/II expression. K562-based artificial APCs (aAPCs) individually expressing various HLA class II genes as a single HLA allele in conjunction with CD80 and CD83 have been reported previously (Butler et al., PloS One 7, e30229 (2012). The Jurkat 76 cell line is a T cell leukemic cell line lacking endogenous TCR, CD4, and CD8 expression. Jurkat 76/CD4 cells were generated by retrovirally transducing the human CD4 gene. HEK293T cells and melanoma cell lines were grown in DMEM supplemented with 10% FBS and 50 µg/ml gentamicin (Thermo Fisher Scientific, Waltham, MA). The K562 and Jurkat 76 cell lines were cultured in RPMI 1640 supplemented with 10% FBS and 50 µg/ml gentamicin.

Peptides

The $MUC5AC_{4922-4941}$ synthetic peptide was purchased from Genscript (Piscataway, NJ) and dissolved at 50 µg/ml in DMSO.

Genes

Novel TCR genes were cloned via 5'-rapid amplification of cDNA ends (RACE) PCR using SMARTer RACE 5'/3' Kit (Takara Bio, Shiga, Japan) and sequenced as previously described. All genes were cloned into the pMX retroviral vector and transduced into cell lines using the 293GPG and PG13 cell-based retrovirus system.

Antibodies

The following antibodies were used for flow cytometry analysis: APC-Cy7-conjugated anti-CD4 (RPA-T4, Bioleg-end, San Diego, CA)[44], and PE-conjugated anti-His tag (AD1.1.10, Abcam, Cambridge, MA). Dead cells were distinguished with the LIVE/DEAD Fixable Near-IR Dead Cell Stain Kit 465 (Thermo Fisher Scientific, Waltham, MA). Stained cells were analyzed with Canto II or LSRFortessa X-20 (BD Biosciences, Franklin Lakes, NJ). Cell sorting was conducted using a FACS Aria II (BD Biosciences, coated plate (XPressBio, Frederick, MD) and an anti-His tag biotinylated mAb (AD1.1.10, R&D Systems, Minneapolis, MN). Soluble HLA class II monomer was dimerized using PE-conjugated anti-His mAb (AD1.1.10, Abcam, Cambridge, MA) at a 2:1 molar ratio for 1.5 hours at 4° C. for staining.

TABLE 5

| HLA-DP Class II Molecules |
| --- |
| Signal Peptide; *DPB1\*04:01 L112W/V141M Extracellular Domain*; <u>Gly/Ser Linker</u>; Zip Sequences and His tag sequences) (SEQ ID NO: 14)<br>MMRPIVLVLLFATSALARATPENYLFQGRQECYAFNGTQRFLERYIYNREEFARFDSDVGEFRAVTELGRPAAE<br>YWNSQKDILEEKRAVPDRMCRHNYELGGPMTLQRRVQPRVNVSPSKKGPLQHHNWLVCHVTDFYPGSIQVRWFL<br>NGQEETAGVMSTNLIRNGDWTFQILVMLEMTPQQGDVYTCQVEHTSLDSPVTVEWKAQSDSARS<u>KGGGGSLEIE</u><br><u>AAFLE</u>RENTALETRVAELRQRVQRLRNRVSQYRTRYGPLGGGK |
| Signal Peptide; *DPA1\*01:03 Extracellular Domain*; <u>Gly/Ser Linker, Zip Sequences and His tag sequences</u>) (SEQ ID NO: 15)<br>MMRPIVLVLLFATSALAIKADHVSTYAAFVQTHRPTGEFMFEFDEDEMFYVDLDKKETVWHLEEFGQAFSFEAQ<br>GGLANIAILNNNLNTLIQRSNHTQATNDPPEVTVFPKEPVELGQPNTLICHIDKFFPPVLNVTWLCNGELVTEG<br>VAESLFLPRTDYSFHKFHYLTFVPSAEDFYDCRVEHWGLDQPLLKHWEAQEPIQMPETTE<u>TGGGGSLEIRAAFL</u><br><u>RQRNTALRTEVAELEQEVQRLENEVSQYETRYGPLGGGKGSHHHHHH</u> |

Franklin Lakes, NJ). Data analysis was performed using FlowJo software (Tree Star, Ashland, OR).

TCR Transduction into Primary T Cells

CD3[+] and CD4[+] T cells were purified using the Pan T Cell Isolation Kit (Miltenyi Biotec, Bergisch Gladbach, Germany) and CD4[+] T Cell Isolation Kit (Miltenyi Biotec, Bergisch Gladbach, Germany), respectively. Purified T cells were stimulated with aAPC/mOKT3 irradiated with 200 Gy at an E:T ratio of 20:1. Starting the following day, activated T cells were retrovirally transduced with the cloned TCR genes via centrifugation for 1 hour at 1,000×g at 32° C. for 3 consecutive days or using a Retronectin-coated plate (Takara Bio, Shiga, Japan). On the following day, 100 IU/ml IL-2 and 10 ng/ml IL-15 were added to the TCR-transduced T cells. The culture medium was replenished every 2-3 days.

Generation of the HLA Class II Monomer and Dimer

The extracellular domain of the wild-type class II α gene was fused with an acidic leucine zipper via a GGGS (SEQ ID NO: 30) linker followed by a 6×His tag via a GS linker (see SEQ ID NO: 15; Table 5). The ectodomain of the class II β gene carrying mutations (see SEQ ID NO: 14) was similarly linked with a basic leucine zipper via a GGGS (SEQ ID NO: 30) linker (see SEQ ID NO: 14). HEK293T cells and A375 cells were transfected with the α and β genes using the 293GPG cell-based retrovirus system and cultured in DMEM supplemented with 10% FBS and 50 µg/ml gentamicin. For DP4 dimer staining, HEK293T cells stably secreting soluble DP4$^{L112W/V141M}$ protein were grown until confluent, and the medium was changed to serum-free 293 SFM II medium (Thermo Fisher Scientific, Waltham, MA). After forty-eight hours, the conditioned medium was harvested and concentrated using Amicon Ultra filters (molecular weight cut-off (MWCO) 10 kDa) (MilliporeSigma, Burlington, MA). The soluble HLA class II-containing supernatant was then mixed with 100 µg/ml peptide of interest for 20-24 hours at 37° C. for in vitro peptide exchange. Monomer that was not subjected to peptide exchange was used as a control. The concentration of the monomer was measured by specific ELISA using a nickel-

Stimulation of DP4-Restricted Antigen-Specific CD4[+] T Cells

CD4[+] T cells were purified using a CD4[+] T Cell Isolation Kit (Miltenyi Biotec, Bergisch Gladbach, Germany). Purified T cells were stimulated with DP4-expressing aAPCs pulsed with DP4-restricted peptides at 10 µg/ml and irradiated at 200 Gy at an E:T ratio of 20:1. After forty-eight hours, 10 IU/ml IL-2 and 10 ng/ml IL-15 were added to the CD4[+] T cells. The culture medium supplemented with IL-2 (10 IU/ml) and IL-15 (10 ng/ml) was replenished every 2-3 days. After 2 weeks of stimulation, the T cells were subjected to DP4$^{L112W/V141M}$ dimer staining.

HLA Class II Dimer Staining

Primary T cells and Jurkat 76/CD4 T cells transduced with exogenous TCR gene were pretreated with 50 nM dasatinib (LC Laboratories, Woburn, MA) for 30 min at 37° C.[46] and stained with 5-15 µg/ml class II dimer for 4-5 hours at room temperature. After washing, cell surface molecules were counterstained with an APC-Cy7-conjugated anti-CD4 mAb.

ELISPOT Assay

Cytokine ELISPOT assays were performed as previously reported (see, e.g., Yamashita et al., Nat. Commun. 8:15244 (2017); and Anczurowski et al., Sci. Rep. 8:4804 (2018)).

Statistical Analysis

Statistical analysis was performed using GraphPad Prism 6.0 software (GraphPad Software, San Diego, CA). Unpaired two-tailed Student's t-tests were used for two-sample comparisons. No statistical method was used to predetermine sample size. The investigators were not blinded to allocation during the experiments or outcome assessment. The experiments were not randomized.

Example 2— Characterization of MUC5AC$_{4922-4941}$TCR

Primary CD4[+] T cells isolated from six DP4[+] melanoma patients were stimulated only once with DP4-aAPCs individually pulsed with a peptide fragment of MUC5AC (4922-4941) and stained with cognate DP4$^{L112W/V141M}$ dimers. To avoid potential in vitro priming, weak stimulatory conditions were utilized. The MUC5AC$_{4922-4941}$ was found to be immunogenic by dimer staining (data not shown).

Figure 1B:
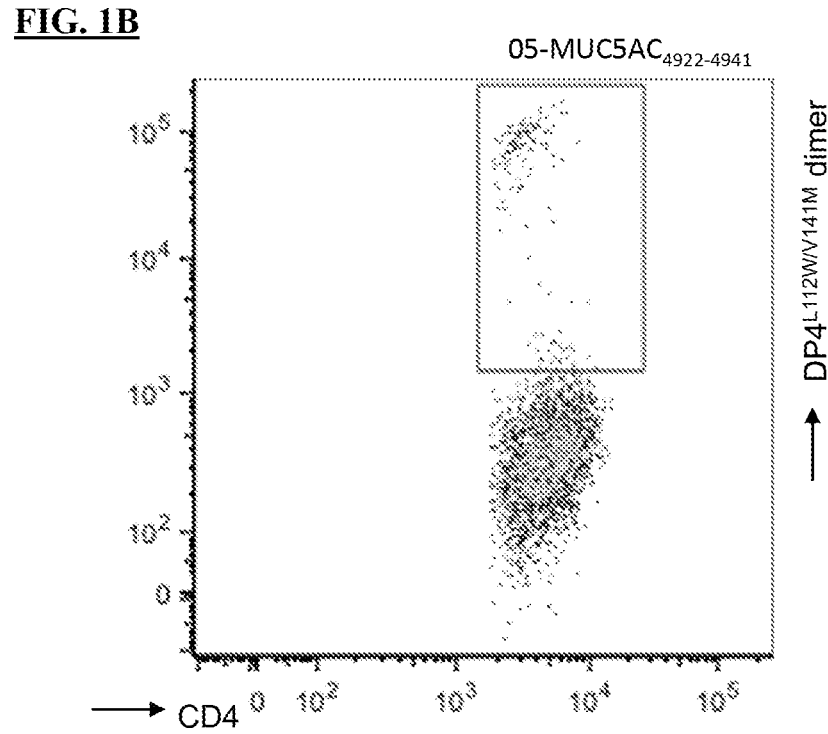
Figure 4E:
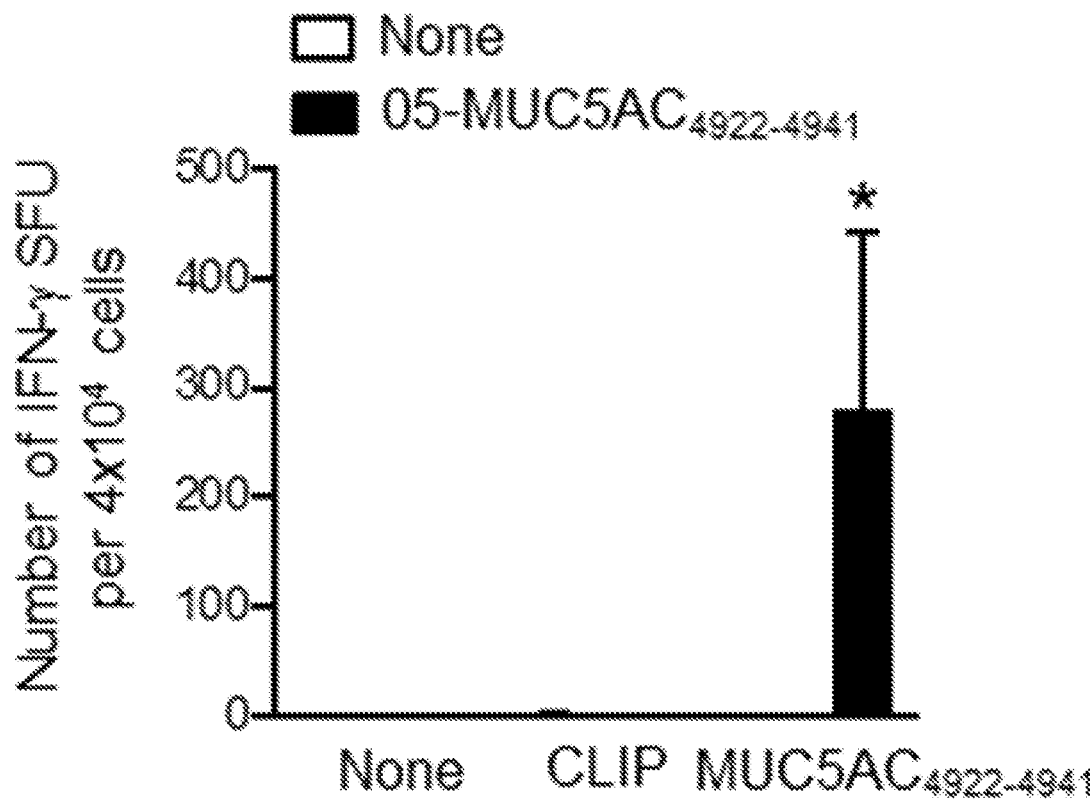
Figure 5:
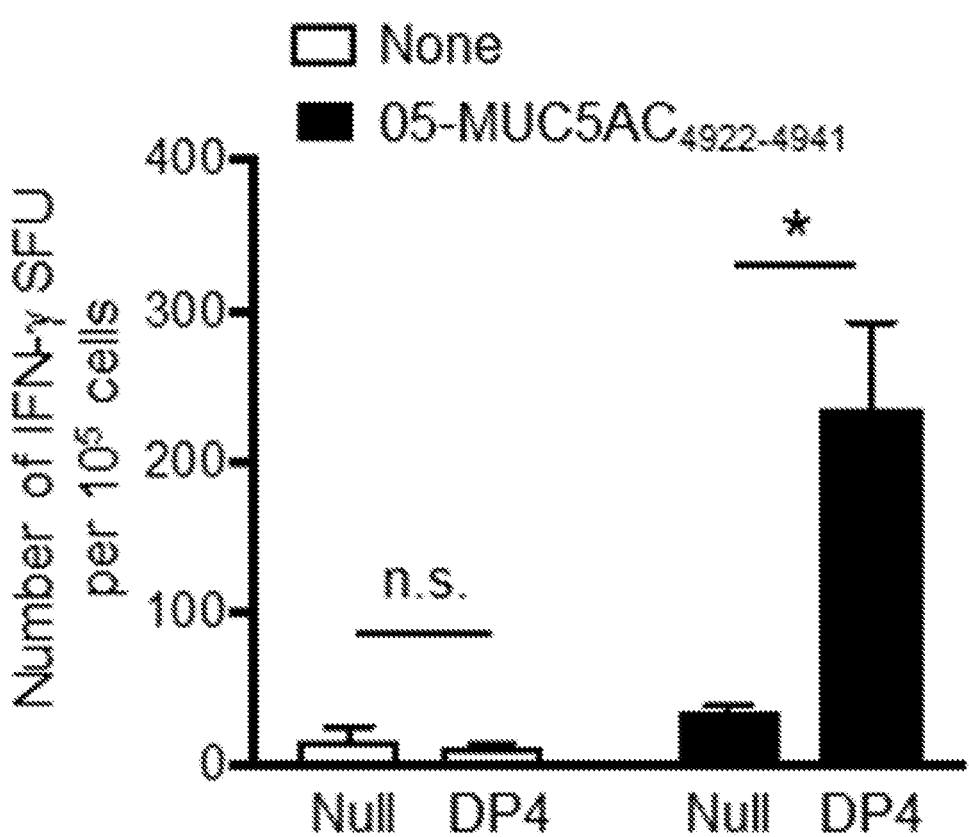
FIG. 5 is a bar graph showing the results of IFN-γ ELISPOT assays of human primary T cells retrovirally transduced with $05-MUC5AC_{4922-4941}$ and stimulated with peptide-unpulsed HLA-null or DP4-aAPCs transduced with $MUC5AC_{4914-4949}$ minigene (MHYQCQCVCSGW GDPHYITFDGTYYTFLDNCTYVLVQ; SEQ ID NO: 29). *, P<0.05 by Student's t-test. Bars and error bars represent the mean±SD of results in triplicate experiments.

To validate the dimer staining results, we cloned a DP4-restricted TCR gene specific for MUC5AC$_{4922-4941}$ (FIGS. 1A-1B and Table 5) from the dimer-positive T cells. When clonotypically reconstituted in human CD4$^+$ TCR-deficient T cells, the MUC5AC$_{4922-4941}$ TCR was successfully stained by the cognate DP4$^{L112W/V141M}$ dimers (FIGS. 2A-8D) and were functional in a DP4-restricted and antigen-specific manner (FIG. 3).

The TCR 03-MUC5AC$_{4922-4941}$ was able to recognize a cognate peptide that was endogenously processed and presented by DP4 (FIGS. 4A-4E and 5).

TABLE 5

| | | | | DP4-Restricted TCR | | | |
|---|---|---|---|---|---|---|---|
| No. | Peptide | TRAV | TRAJ | TCR-alpha CDR 3 | TRBV | TRBJ | TCR-beta CDR 3 |
| 05 | MUC5AC$_{4922-4941}$ | 38-1*03 | 58*01 | CAFMKRAETSGSRLTF (SEQ ID NO: 7) | 6-2*01 | 2-5*01 | CASSYWPTRETQYF (SEQ ID NO: 10) |

The invention claimed is:

1. A nucleic acid molecule comprising:

(a) a first nucleotide sequence encoding a recombinant T cell receptor (TCR) or an antigen binding portion thereof that specifically binds an epitope of MUC5AC human mucin 5AC (MUC5AC) ("anti-MUC5AC TCR"), wherein the epitope comprises the amino acid sequence set forth in SEQ ID NO: 13, which is complexed with an HLA class II molecule HLA-DP4 allele; and (b) a second nucleotide sequence, wherein the second nucleotide sequence or the polypeptide encoded by the second nucleotide sequence inhibits the expression of an endogenous TCR, wherein the anti-MUC5AC TCR comprises an alpha chain variable domain comprising an alpha chain CDR1, an alpha chain CDR2, and an alpha chain CDR3; and a beta chain variable domain comprising a beta chain CDR1, a beta chain CDR2, and a beta chain CDR3;

wherein:

(i) the beta chain CDR3 of the anti-MUC5AC TCR comprises the amino acid sequence set forth in SEQ ID NO: 10;

(ii) the beta chain CDR2 of the anti-MUC5AC TCR comprises the amino acid sequence set forth in SEQ ID NO: 9;

(iii) the beta chain CDR1 of the anti-MUC5AC TCR comprises the amino acid sequence set forth in SEQ ID NO: 8;

(iv) the alpha chain CDR3 of the anti-MUC5AC TCR comprises the amino acid sequence set forth in SEQ ID NO: 7;

(v) the alpha chain CDR2 of the anti-MUC5AC TCR comprises the amino acid sequence set forth in SEQ ID NO: 6; and (vi) the alpha chain CDR1 of the anti-MUC5AC TCR comprises the amino acid sequence set forth in SEQ ID NO: 5.

2. The nucleic acid molecule of claim 1, wherein (i) the alpha chain variable domain of the anti-MUC5AC TCR comprises the amino acid sequence of a variable domain present in the amino acid sequence set forth in SEQ ID NO: 1;

ii) the beta chain variable domain of the anti-MUC5AC TCR comprises the amino acid sequence of a variable domain present in the amino acid sequence set forth in SEQ ID NO: 2; or (ii) both (i) and (ii).

3. The nucleic acid molecule of claim 1, wherein:

(a) the anti-MUC5AC TCR further comprises an alpha chain constant region, wherein the alpha chain constant region is different from a constant region of an endogenous alpha chain, and wherein (i) the alpha chain constant region comprises an amino acid sequence having at least about 85% sequence identity to a constant region present in the amino acid sequence set forth in SEQ ID NO: 1; or (ii) the alpha chain constant region comprises an amino acid sequence comprising at least 1 amino acid substitution relative to a constant region present in the amino acid sequence set forth in SEQ ID NO: 1;

(b) the anti-MUC5AC TCR further comprises a beta chain constant region, wherein the beta chain constant region is different from a constant region of an endogenous beta chainp, and wherein (i) the beta chain constant region comprises an amino acid sequence having at least about 85% sequence identity to a constant region present in the amino acid sequence set forth in SEQ ID NO: 2; or (ii) the beta chain constant region comprises an amino acid sequence comprising at least 1 amino acid substitution relative to a constant region present in the amino acid sequence set forth in SEQ ID NO: 2; or (c) both (a) and (b).

4. The nucleic acid molecule of claim 1, wherein the second nucleotide sequence is one or more siRNAs that reduce the expression of endogenous TCRs, wherein the one or more siRNAs are complementary to a target sequence within a nucleotide sequence encoding a constant region of the endogenous TCRs.

5. A vector comprising the nucleic acid molecule of claim 1.

6. A cell comprising the nucleic acid molecule of claim 1.

7. The cell of claim 6, which further expresses CD3.

8. The cell of claim 6, which is a T cell.

9. The cell of claim 6, which is a natural killer (NK) cell, a natural killer T (NKT) cell, or an ILC cell.

10. The nucleic acid molecule of claim 1, wherein the anti-MUC5AC TCR comprises an alpha chain comprising the amino acid sequence set forth in SEQ ID NO: 1 and a beta chain comprising the amino acid sequence set forth in SEQ ID NO: 2.

11. A cell comprising the nucleic acid molecule of claim 10.

12. The cell of claim 11, which further expresses CD3.

13. The cell of claim 11, which is a T cell.

14. The cell of claim 11, which is an NK cell, a natural killer T (NKT) cell, or an ILC cell.

15. A method of treating a cancer in a subject in need thereof, comprising administering to the subject the cell of claim 6.

16. The method of claim 15, wherein the cancer comprises melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignances, or a combination of one or more of said cancers.

17. The method of claim 15, wherein the cancer is locally advanced, advanced, or metastatic.

18. The method of claim 15, wherein the cancer is relapsed or refractory.

19. A method of engineering an antigen-targeting cell, comprising transducing a cell collected from a subject in need of a T cell therapy with the nucleic acid molecule of claim 1.

\* \* \* \* \*

SEQUENCE LISTING

<160> NUMBER OF SEQ ID NOS: 30

<210> SEQ ID NO 1
<211> LENGTH: 257
<212> TYPE: PRT
<213> ORGANISM: artificial sequence
<220> FEATURE:
<223> OTHER INFORMATION: Alpha Chain

<400> SEQUENCE: 1

```
Gln Thr Val Thr Gln Ser Gln Pro Glu Met Ser Val Gln Glu Ala Glu
1               5                   10                  15

Thr Val Thr Leu Ser Cys Thr Tyr Asp Thr Ser Glu Ser Asn Tyr Tyr
            20                  25                  30

Leu Phe Trp Tyr Lys Gln Pro Pro Ser Arg Gln Met Ile Leu Val Ile
        35                  40                  45

Arg Gln Glu Ala Tyr Lys Gln Gln Asn Ala Thr Glu Asn Arg Phe Ser
    50                  55                  60

Val Asn Phe Gln Lys Ala Ala Lys Ser Phe Ser Leu Lys Ile Ser Asp
65                  70                  75                  80

Ser Gln Leu Gly Asp Thr Ala Met Tyr Phe Cys Ala Phe Met Lys Arg
            85                  90                  95

Ala Glu Thr Ser Gly Ser Arg Leu Thr Phe Gly Glu Gly Thr Gln Leu
            100                 105                 110

Thr Val Asn Pro Asp Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240
```

```
Leu Lys Val Ala Gly Phe Asn Leu Leu Met Thr Leu Arg Leu Trp Ser
            245                 250                 255

Ser

<210> SEQ ID NO 2
<211> LENGTH: 292
<212> TYPE: PRT
<213> ORGANISM: artificial sequence
<220> FEATURE:
<223> OTHER INFORMATION: Beta Chain

<400> SEQUENCE: 2

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Tyr Trp
            85                  90                  95

Pro Thr Arg Glu Thr Gln Tyr Phe Gly Pro Gly Thr Arg Leu Leu Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
            165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
            245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
            275                 280                 285

Asp Ser Arg Gly
    290

<210> SEQ ID NO 3

<400> SEQUENCE: 3

000
```

```
<210> SEQ ID NO 4

<400> SEQUENCE: 4

000

<210> SEQ ID NO 5
<211> LENGTH: 7
<212> TYPE: PRT
<213> ORGANISM: artificial sequence
<220> FEATURE:
<223> OTHER INFORMATION: Alpha Chain

<400> SEQUENCE: 5

Thr Ser Glu Ser Asn Tyr Tyr
1               5

<210> SEQ ID NO 6
<211> LENGTH: 8
<212> TYPE: PRT
<213> ORGANISM: artificial sequence
<220> FEATURE:
<223> OTHER INFORMATION: anti-MUC5AC TCR

<400> SEQUENCE: 6

Gln Glu Ala Tyr Lys Gln Gln Asn
1               5

<210> SEQ ID NO 7
<211> LENGTH: 16
<212> TYPE: PRT
<213> ORGANISM: artificial sequence
<220> FEATURE:
<223> OTHER INFORMATION: TCR-alpha CDR 3

<400> SEQUENCE: 7

Cys Ala Phe Met Lys Arg Ala Glu Thr Ser Gly Ser Arg Leu Thr Phe
1               5                   10                  15

<210> SEQ ID NO 8
<211> LENGTH: 5
<212> TYPE: PRT
<213> ORGANISM: artificial sequence
<220> FEATURE:
<223> OTHER INFORMATION: anti-MUC5AC TCR

<400> SEQUENCE: 8

Met Asn His Glu Tyr
1               5

<210> SEQ ID NO 9
<211> LENGTH: 6
<212> TYPE: PRT
<213> ORGANISM: artificial sequence
<220> FEATURE:
<223> OTHER INFORMATION: anti-MUC5AC TCR

<400> SEQUENCE: 9

Ser Val Gly Glu Gly Thr
1               5

<210> SEQ ID NO 10
<211> LENGTH: 14
<212> TYPE: PRT
<213> ORGANISM: artificial sequence
<220> FEATURE:
<223> OTHER INFORMATION: TCR-beta CDR 3
```

```
<400> SEQUENCE: 10

Cys Ala Ser Ser Tyr Trp Pro Thr Arg Glu Thr Gln Tyr Phe
1               5                   10

<210> SEQ ID NO 11

<400> SEQUENCE: 11

000

<210> SEQ ID NO 12

<400> SEQUENCE: 12

000

<210> SEQ ID NO 13
<211> LENGTH: 20
<212> TYPE: PRT
<213> ORGANISM: artificial sequence
<220> FEATURE:
<223> OTHER INFORMATION: epitope of MUC5AC

<400> SEQUENCE: 13

Ser Gly Trp Gly Asp Pro His Tyr Ile Thr Phe Asp Gly Thr Tyr Tyr
1               5                   10                  15

Thr Phe Leu Asp
            20

<210> SEQ ID NO 14
<211> LENGTH: 265
<212> TYPE: PRT
<213> ORGANISM: artificial sequence
<220> FEATURE:
<223> OTHER INFORMATION: Signal Peptide

<400> SEQUENCE: 14

Met Met Arg Pro Ile Val Leu Val Leu Leu Phe Ala Thr Ser Ala Leu
1               5                   10                  15

Ala Arg Ala Thr Pro Glu Asn Tyr Leu Phe Gln Gly Arg Gln Glu Cys
            20                  25                  30

Tyr Ala Phe Asn Gly Thr Gln Arg Phe Leu Glu Arg Tyr Ile Tyr Asn
        35                  40                  45

Arg Glu Glu Phe Ala Arg Phe Asp Ser Asp Val Gly Glu Phe Arg Ala
    50                  55                  60

Val Thr Glu Leu Gly Arg Pro Ala Ala Glu Tyr Trp Asn Ser Gln Lys
65                  70                  75                  80

Asp Ile Leu Glu Glu Lys Arg Ala Val Pro Asp Arg Met Cys Arg His
                85                  90                  95

Asn Tyr Glu Leu Gly Gly Pro Met Thr Leu Gln Arg Arg Val Gln Pro
            100                 105                 110

Arg Val Asn Val Ser Pro Ser Lys Lys Gly Pro Leu Gln His His Asn
            115                 120                 125

Trp Leu Val Cys His Val Thr Asp Phe Tyr Pro Gly Ser Ile Gln Val
        130                 135                 140

Arg Trp Phe Leu Asn Gly Gln Glu Glu Thr Ala Gly Val Met Ser Thr
145                 150                 155                 160

Asn Leu Ile Arg Asn Gly Asp Trp Thr Phe Gln Ile Leu Val Met Leu
                165                 170                 175
```

```
Glu Met Thr Pro Gln Gln Gly Asp Val Tyr Thr Cys Gln Val Glu His
            180             185             190

Thr Ser Leu Asp Ser Pro Val Thr Val Glu Trp Lys Ala Gln Ser Asp
        195             200             205

Ser Ala Arg Ser Lys Gly Gly Gly Ser Leu Glu Ile Glu Ala Ala
    210             215             220

Phe Leu Glu Arg Glu Asn Thr Ala Leu Glu Thr Arg Val Ala Glu Leu
225             230             235             240

Arg Gln Arg Val Gln Arg Leu Arg Asn Arg Val Ser Gln Tyr Arg Thr
            245             250             255

Arg Tyr Gly Pro Leu Gly Gly Gly Lys
            260             265

<210> SEQ ID NO 15
<211> LENGTH: 269
<212> TYPE: PRT
<213> ORGANISM: artificial sequence
<220> FEATURE:
<223> OTHER INFORMATION: Signal Peptide

<400> SEQUENCE: 15

Met Met Arg Pro Ile Val Leu Val Leu Leu Phe Ala Thr Ser Ala Leu
1               5               10              15

Ala Ile Lys Ala Asp His Val Ser Thr Tyr Ala Ala Phe Val Gln Thr
            20              25              30

His Arg Pro Thr Gly Glu Phe Met Phe Glu Phe Asp Glu Asp Glu Met
        35              40              45

Phe Tyr Val Asp Leu Asp Lys Lys Glu Thr Val Trp His Leu Glu Glu
    50              55              60

Phe Gly Gln Ala Phe Ser Phe Glu Ala Gln Gly Gly Leu Ala Asn Ile
65              70              75              80

Ala Ile Leu Asn Asn Asn Leu Asn Thr Leu Ile Gln Arg Ser Asn His
            85              90              95

Thr Gln Ala Thr Asn Asp Pro Pro Glu Val Thr Val Phe Pro Lys Glu
            100             105             110

Pro Val Glu Leu Gly Gln Pro Asn Thr Leu Ile Cys His Ile Asp Lys
        115             120             125

Phe Phe Pro Pro Val Leu Asn Val Thr Trp Leu Cys Asn Gly Glu Leu
    130             135             140

Val Thr Glu Gly Val Ala Glu Ser Leu Phe Leu Pro Arg Thr Asp Tyr
145             150             155             160

Ser Phe His Lys Phe His Tyr Leu Thr Phe Val Pro Ser Ala Glu Asp
            165             170             175

Phe Tyr Asp Cys Arg Val Glu His Trp Gly Leu Asp Gln Pro Leu Leu
            180             185             190

Lys His Trp Glu Ala Gln Glu Pro Ile Gln Met Pro Glu Thr Thr Glu
        195             200             205

Thr Gly Gly Gly Gly Ser Leu Glu Ile Arg Ala Ala Phe Leu Arg Gln
        210             215             220

Arg Asn Thr Ala Leu Arg Thr Glu Val Ala Glu Leu Glu Gln Glu Val
225             230             235             240

Gln Arg Leu Glu Asn Glu Val Ser Gln Tyr Glu Thr Arg Tyr Gly Pro
            245             250             255

Leu Gly Gly Gly Lys Gly Ser His His His His His
            260             265
```

```
<210> SEQ ID NO 16
<211> LENGTH: 5654
<212> TYPE: PRT
<213> ORGANISM: artificial sequence
<220> FEATURE:
<223> OTHER INFORMATION: MUC5AC

<400> SEQUENCE: 16

Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
                20                  25                  30

Glu Ser Ser Tyr Lys His His Pro Ala Leu Ser Pro Ile Ala Arg Gly
            35                  40                  45

Pro Ser Gly Val Pro Leu Arg Gly Ala Thr Val Phe Pro Ser Leu Arg
        50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
            100                 105                 110

Ala Ala Tyr Glu Asp Phe Asn Ile Gln Leu Arg Arg Ser Gln Glu Ser
        115                 120                 125

Ala Ala Pro Thr Leu Ser Arg Val Leu Met Lys Val Asp Gly Val Val
        130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175

Thr Lys Val Glu Ala Arg Leu Gly Leu Val Leu Met Trp Asn His Asp
            180                 185                 190

Asp Ser Leu Leu Leu Glu Leu Asp Thr Lys Tyr Ala Asn Lys Thr Cys
        195                 200                 205

Gly Leu Cys Gly Asp Phe Asn Gly Met Pro Val Val Ser Glu Leu Leu
        210                 215                 220

Ser His Asn Thr Lys Leu Thr Pro Met Glu Phe Gly Asn Leu Gln Lys
225                 230                 235                 240

Met Asp Asp Pro Thr Asp Gln Cys Gln Asp Pro Val Pro Glu Pro Pro
                245                 250                 255

Arg Asn Cys Ser Thr Gly Phe Gly Ile Cys Glu Glu Leu Leu His Gly
            260                 265                 270

Gln Leu Phe Ser Gly Cys Val Ala Leu Val Asp Val Gly Ser Tyr Leu
        275                 280                 285

Glu Ala Cys Arg Gln Asp Leu Cys Phe Cys Glu Asp Thr Asp Leu Leu
        290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
                325                 330                 335

Lys Cys Pro Asn Asn Met Gln Tyr His Glu Cys Arg Ser Pro Cys Ala
            340                 345                 350

Asp Thr Cys Ser Asn Gln Glu His Ser Arg Ala Cys Glu Asp His Cys
            355                 360                 365
```

-continued

Val Ala Gly Cys Phe Cys Pro Glu Gly Thr Val Leu Asp Asp Ile Gly
    370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
                405                 410                 415

Thr Cys Ser Gly Gly Arg Trp Ser Cys Gln Glu Val Pro Cys Pro Gly
            420                 425                 430

Thr Cys Ser Val Leu Gly Gly Ala His Phe Ser Thr Phe Asp Gly Lys
            435                 440                 445

Gln Tyr Thr Val His Gly Asp Cys Ser Tyr Val Leu Thr Lys Pro Cys
    450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
                485                 490                 495

Ala Gln Thr Val Val Val Ile Lys Ala Ser Gly Glu Val Phe Leu Asn
            500                 505                 510

Gln Ile Tyr Thr Gln Leu Pro Ile Ser Ala Ala Asn Val Thr Ile Phe
    515                 520                 525

Arg Pro Ser Thr Phe Phe Ile Ile Ala Gln Thr Ser Leu Gly Leu Gln
    530                 535                 540

Leu Asn Leu Gln Leu Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
            565                 570                 575

Ile Gln Ala Asp Asp Phe Arg Thr Leu Ser Gly Val Val Glu Ala Thr
            580                 585                 590

Ala Ala Ala Phe Phe Asn Thr Phe Lys Thr Gln Ala Ala Cys Pro Asn
            595                 600                 605

Ile Arg Asn Ser Phe Glu Asp Pro Cys Ser Leu Ser Val Glu Asn Glu
    610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
                645                 650                 655

Cys Met Phe Asp Thr Cys Asn Cys Glu Arg Ser Glu Asp Cys Leu Cys
            660                 665                 670

Ala Ala Leu Ser Ser Tyr Val His Ala Cys Ala Ala Lys Gly Val Gln
            675                 680                 685

Leu Gly Gly Trp Arg Asp Gly Val Cys Thr Lys Pro Met Thr Thr Cys
    690                 695                 700

Pro Lys Ser Met Thr Tyr His Tyr His Val Ser Thr Cys Gln Pro Thr
705                 710                 715                 720

Cys Arg Ser Leu Ser Glu Gly Asp Ile Thr Cys Ser Val Gly Phe Ile
                725                 730                 735

Pro Val Asp Gly Cys Ile Cys Pro Lys Gly Thr Phe Leu Asp Asp Thr
                740                 745                 750

Gly Lys Cys Val Gln Ala Ser Asn Cys Pro Cys Tyr His Arg Gly Ser
            755                 760                 765

Met Ile Pro Asn Gly Glu Ser Val His Asp Ser Gly Ala Ile Cys Thr
    770                 775                 780

Cys Thr His Gly Lys Leu Ser Cys Ile Gly Gly Gln Ala Pro Ala Pro

-continued

```
785                 790                 795                 800
Val Cys Ala Ala Pro Met Val Phe Phe Asp Cys Arg Asn Ala Thr Pro
            805                 810                 815
Gly Asp Thr Gly Ala Gly Cys Gln Lys Ser Cys His Thr Leu Asp Met
            820                 825                 830
Thr Cys Tyr Ser Pro Gln Cys Val Pro Gly Cys Val Cys Pro Asp Gly
            835                 840                 845
Leu Val Ala Asp Gly Glu Gly Gly Cys Ile Thr Ala Glu Asp Cys Pro
    850                 855                 860
Cys Val His Asn Glu Ala Ser Tyr Arg Ala Gly Gln Thr Ile Arg Val
865                 870                 875                 880
Gly Cys Asn Thr Cys Thr Cys Asp Ser Arg Met Trp Arg Cys Thr Asp
            885                 890                 895
Asp Pro Cys Leu Ala Thr Cys Ala Val Tyr Gly Asp Gly His Tyr Leu
            900                 905                 910
Thr Phe Asp Gly Gln Ser Tyr Ser Phe Asn Gly Asp Cys Glu Tyr Thr
            915                 920                 925
Leu Val Gln Asn His Cys Gly Gly Lys Asp Ser Thr Gln Asp Ser Phe
    930                 935                 940
Arg Val Val Thr Glu Asn Val Pro Cys Gly Thr Thr Gly Thr Thr Cys
945                 950                 955                 960
Ser Lys Ala Ile Lys Ile Phe Leu Gly Gly Phe Glu Leu Lys Leu Ser
            965                 970                 975
His Gly Lys Val Glu Val Ile Gly Thr Asp Glu Ser Gln Glu Val Pro
            980                 985                 990
Tyr Thr Ile Arg Gln Met Gly Ile  Tyr Leu Val Val Asp  Thr Asp Ile
        995                 1000                1005
Gly Leu  Val Leu Leu Trp Asp  Lys Lys Thr Ser Ile  Phe Ile Asn
    1010                1015                1020
Leu Ser  Pro Glu Phe Lys Gly  Arg Val Cys Gly Leu  Cys Gly Asn
    1025                1030                1035
Phe Asp  Asp Ile Ala Val Asn  Asp Phe Ala Thr Arg  Ser Arg Ser
    1040                1045                1050
Val Val  Gly Asp Val Leu Glu  Phe Gly Asn Ser Trp  Lys Leu Ser
    1055                1060                1065
Pro Ser  Cys Pro Asp Ala Leu  Ala Pro Lys Asp Pro  Cys Thr Ala
    1070                1075                1080
Asn Pro  Phe Arg Lys Ser Trp  Ala Gln Lys Gln Cys  Ser Ile Leu
    1085                1090                1095
His Gly  Pro Thr Phe Ala Ala  Cys His Ala His Val  Glu Pro Ala
    1100                1105                1110
Arg Tyr  Tyr Glu Ala Cys Val  Asn Asp Ala Cys Ala  Cys Asp Ser
    1115                1120                1125
Gly Gly  Asp Cys Glu Cys Phe  Cys Thr Ala Val Ala  Ala Tyr Ala
    1130                1135                1140
Gln Ala  Cys His Glu Val Gly  Leu Cys Val Ser Trp  Arg Thr Pro
    1145                1150                1155
Ser Ile  Cys Pro Leu Phe Cys  Asp Tyr Tyr Asn Pro  Glu Gly Gln
    1160                1165                1170
Cys Glu  Trp His Tyr Gln Pro  Cys Gly Val Pro Cys  Leu Arg Thr
    1175                1180                1185
Cys Arg  Asn Pro Arg Gly Asp  Cys Leu Arg Asp Val  Arg Gly Leu
    1190                1195                1200
```

US 12,624,082 B2

87

88

-continued

```
Glu Gly Cys Tyr Pro Lys Cys Pro Pro Glu Ala Pro Ile Phe Asp
    1205          1210          1215

Glu Asp Lys Met Gln Cys Val Ala Thr Cys Pro Thr Pro Pro Leu
    1220          1225          1230

Pro Pro Arg Cys His Val His Gly Lys Ser Tyr Arg Pro Gly Ala
    1235          1240          1245

Val Val Pro Ser Asp Lys Asn Cys Gln Ser Cys Leu Cys Thr Glu
    1250          1255          1260

Arg Gly Val Glu Cys Thr Tyr Lys Ala Glu Ala Cys Val Cys Thr
    1265          1270          1275

Tyr Asn Gly Gln Arg Phe His Pro Gly Asp Val Ile Tyr His Thr
    1280          1285          1290

Thr Asp Gly Thr Gly Gly Cys Ile Ser Ala Arg Cys Gly Ala Asn
    1295          1300          1305

Gly Thr Ile Glu Arg Arg Val Tyr Pro Cys Ser Pro Thr Thr Pro
    1310          1315          1320

Val Pro Pro Thr Thr Phe Ser Phe Ser Thr Pro Pro Leu Val Val
    1325          1330          1335

Ser Ser Thr His Thr Pro Ser Asn Gly Pro Ser Ser Ala His Thr
    1340          1345          1350

Gly Pro Pro Ser Ser Ala Trp Pro Thr Thr Ala Gly Thr Ser Pro
    1355          1360          1365

Arg Thr Arg Leu Pro Thr Ala Ser Ala Ser Leu Pro Pro Val Cys
    1370          1375          1380

Gly Glu Lys Cys Leu Trp Ser Pro Trp Met Asp Val Ser Arg Pro
    1385          1390          1395

Gly Arg Gly Thr Asp Ser Gly Asp Phe Asp Thr Leu Glu Asn Leu
    1400          1405          1410

Arg Ala His Gly Tyr Arg Val Cys Glu Ser Pro Arg Ser Val Glu
    1415          1420          1425

Cys Arg Ala Glu Asp Ala Pro Gly Val Pro Leu Arg Ala Leu Gly
    1430          1435          1440

Gln Arg Val Gln Cys Ser Pro Asp Val Gly Leu Thr Cys Arg Asn
    1445          1450          1455

Arg Glu Gln Ala Ser Gly Leu Cys Tyr Asn Tyr Gln Ile Arg Val
    1460          1465          1470

Gln Cys Cys Thr Pro Leu Pro Cys Ser Thr Ser Ser Pro Ala
    1475          1480          1485

Gln Thr Thr Pro Pro Thr Thr Ser Lys Thr Thr Glu Thr Arg Ala
    1490          1495          1500

Ser Gly Ser Ser Ala Pro Ser Ser Thr Pro Gly Thr Val Ser Leu
    1505          1510          1515

Ser Thr Ala Arg Thr Thr Pro Ala Pro Gly Thr Ala Thr Ser Val
    1520          1525          1530

Lys Lys Thr Phe Ser Thr Pro Ser Pro Pro Val Pro Ala Thr
    1535          1540          1545

Ser Thr Ser Ser Met Ser Thr Thr Ala Pro Gly Thr Ser Val Val
    1550          1555          1560

Ser Ser Lys Pro Thr Pro Thr Glu Pro Ser Thr Ser Ser Cys Leu
    1565          1570          1575

Gln Glu Leu Cys Thr Trp Thr Glu Trp Ile Asp Gly Ser Tyr Pro
    1580          1585          1590
```

-continued

```
Ala Pro Gly Ile Asn Gly Gly Asp Phe Asp Thr Phe Gln Asn Leu
    1595             1600             1605

Arg Asp Glu Gly Tyr Thr Phe Cys Glu Ser Pro Arg Ser Val Gln
    1610             1615             1620

Cys Arg Ala Glu Ser Phe Pro Asn Thr Pro Leu Ala Asp Leu Gly
    1625             1630             1635

Gln Asp Val Ile Cys Ser His Thr Glu Gly Leu Ile Cys Leu Asn
    1640             1645             1650

Lys Asn Gln Leu Pro Pro Ile Cys Tyr Asn Tyr Glu Ile Arg Ile
    1655             1660             1665

Gln Cys Cys Glu Thr Val Asn Val Cys Arg Asp Ile Thr Arg Leu
    1670             1675             1680

Pro Lys Thr Val Ala Thr Thr Arg Pro Thr Pro His Pro Thr Gly
    1685             1690             1695

Ala Gln Thr Gln Thr Thr Phe Thr Thr His Met Pro Ser Ala Ser
    1700             1705             1710

Thr Glu Gln Pro Thr Ala Thr Ser Arg Gly Gly Pro Thr Ala Thr
    1715             1720             1725

Ser Val Thr Gln Gly Thr His Thr Thr Leu Val Thr Arg Asn Cys
    1730             1735             1740

His Pro Arg Cys Thr Trp Thr Lys Trp Phe Asp Val Asp Phe Pro
    1745             1750             1755

Ser Pro Gly Pro His Gly Gly Asp Lys Glu Thr Tyr Asn Asn Ile
    1760             1765             1770

Ile Arg Ser Gly Glu Lys Ile Cys Arg Arg Pro Glu Glu Ile Thr
    1775             1780             1785

Arg Leu Gln Cys Arg Ala Lys Ser His Pro Glu Val Ser Ile Glu
    1790             1795             1800

His Leu Gly Gln Val Val Gln Cys Ser Arg Glu Glu Gly Leu Val
    1805             1810             1815

Cys Arg Asn Gln Asp Gln Gln Gly Pro Phe Lys Met Cys Leu Asn
    1820             1825             1830

Tyr Glu Val Arg Val Leu Cys Cys Glu Thr Pro Arg Gly Cys His
    1835             1840             1845

Met Thr Ser Thr Pro Gly Ser Thr Ser Ser Ser Pro Ala Gln Thr
    1850             1855             1860

Thr Pro Ser Thr Thr Ser Lys Thr Thr Glu Thr Gln Ala Ser Gly
    1865             1870             1875

Ser Ser Ala Pro Ser Ser Thr Pro Gly Thr Val Ser Leu Ser Thr
    1880             1885             1890

Ala Arg Thr Thr Pro Ala Pro Gly Thr Ala Thr Ser Val Lys Lys
    1895             1900             1905

Thr Phe Ser Thr Pro Ser Pro Pro Pro Val Pro Ala Thr Ser Thr
    1910             1915             1920

Ser Ser Met Ser Thr Thr Ala Pro Gly Thr Ser Val Val Ser Ser
    1925             1930             1935

Lys Pro Thr Pro Thr Glu Pro Ser Thr Ser Ser Cys Leu Gln Glu
    1940             1945             1950

Leu Cys Thr Trp Thr Glu Trp Ile Asp Gly Ser Tyr Pro Ala Pro
    1955             1960             1965

Gly Ile Asn Gly Gly Asp Phe Asp Thr Phe Gln Asn Leu Arg Asp
    1970             1975             1980

Glu Gly Tyr Thr Phe Cys Glu Ser Pro Arg Ser Val Gln Cys Arg
```

-continued

```
      1985                1990                1995

Ala Glu  Ser Phe Pro Asn Thr  Pro Leu Ala Asp Leu  Gly Gln Asp
    2000                2005                2010

Val Ile  Cys Ser His Thr Glu  Gly Leu Ile Cys Leu  Asn Lys Asn
    2015                2020                2025

Gln Leu  Pro Pro Ile Cys Tyr  Asn Tyr Glu Ile Arg  Ile Gln Cys
    2030                2035                2040

Cys Glu  Thr Val Asn Val Cys  Arg Asp Ile Thr Arg  Pro Pro Lys
    2045                2050                2055

Thr Val  Ala Thr Thr Arg Pro  Thr Pro His Pro Thr  Gly Ala Gln
    2060                2065                2070

Thr Gln  Thr Thr Phe Thr Thr  His Met Pro Ser Ala  Ser Thr Glu
    2075                2080                2085

Gln Pro  Thr Ala Thr Ser Arg  Gly Gly Pro Thr Ala  Thr Ser Val
    2090                2095                2100

Thr Gln  Gly Thr His Thr Thr  Pro Val Thr Arg Asn  Cys His Pro
    2105                2110                2115

Arg Cys  Thr Trp Thr Thr Trp  Phe Asp Val Asp Phe  Pro Ser Pro
    2120                2125                2130

Gly Pro  His Gly Gly Asp Lys  Glu Thr Tyr Asn Asn  Ile Ile Arg
    2135                2140                2145

Ser Gly  Glu Lys Ile Cys Arg  Arg Pro Glu Glu Ile  Thr Arg Leu
    2150                2155                2160

Gln Cys  Arg Ala Lys Ser His  Pro Glu Val Ser Ile  Glu His Leu
    2165                2170                2175

Gly Gln  Val Val Gln Cys Ser  Arg Glu Glu Gly Leu  Val Cys Arg
    2180                2185                2190

Asn Gln  Asp Gln Gln Gly Pro  Phe Lys Met Cys Leu  Asn Tyr Glu
    2195                2200                2205

Val Arg  Val Leu Cys Cys Glu  Thr Pro Lys Gly Cys  Pro Val Thr
    2210                2215                2220

Ser Thr  Pro Val Thr Ala Pro  Ser Thr Pro Ser Gly  Arg Ala Thr
    2225                2230                2235

Ser Pro  Thr Gln Ser Thr Ser  Ser Trp Gln Lys Ser  Arg Thr Thr
    2240                2245                2250

Thr Leu  Val Thr Thr Ser Thr  Thr Ser Thr Pro Gln  Thr Ser Thr
    2255                2260                2265

Thr Tyr  Ala His Thr Thr Ser  Thr Thr Ser Ala Pro  Thr Ala Arg
    2270                2275                2280

Thr Thr  Ser Ala Pro Thr Thr  Arg Thr Thr Ser Ala  Ser Pro Ala
    2285                2290                2295

Ser Thr  Thr Ser Gly Pro Gly  Asn Thr Pro Ser Pro  Val Pro Thr
    2300                2305                2310

Thr Ser  Thr Ile Ser Ala Pro  Thr Thr Ser Ile Thr  Ser Ala Pro
    2315                2320                2325

Thr Thr  Ser Thr Thr Ser Ala  Pro Thr Ser Ser Thr  Thr Ser Gly
    2330                2335                2340

Pro Gly  Thr Thr Pro Ser Pro  Val Pro Thr Thr Ser  Ile Thr Ser
    2345                2350                2355

Ala Pro  Thr Thr Ser Thr Thr  Ser Ala Pro Thr Thr  Ser Thr Thr
    2360                2365                2370

Ser Ala  Arg Thr Ser Ser Thr  Thr Ser Ala Thr Thr  Thr Ser Arg
    2375                2380                2385
```

-continued

```
Ile Ser Gly Pro Glu Thr Thr  Pro Ser Pro Val Pro  Thr Thr Ser
    2390             2395              2400

Thr Thr Ser Ala Thr Thr Thr  Ser Thr Thr Ser Ala  Pro Thr Thr
    2405             2410              2415

Ser Thr Thr Ser Ala Pro Thr  Ser Ser Thr Thr Ser  Ser Pro Gln
    2420             2425              2430

Thr Ser Thr Thr Ser Ala Pro  Thr Thr Ser Thr Thr  Ser Gly Pro
    2435             2440              2445

Gly Thr Thr Pro Ser Pro Val  Pro Thr Thr Ser Thr  Thr Ser Ala
    2450             2455              2460

Pro Thr Thr Arg Thr Thr Ser  Ala Pro Lys Ser Ser  Thr Thr Ser
    2465             2470              2475

Ala Ala Thr Thr Ser Thr Thr  Ser Gly Pro Glu Thr  Thr Pro Arg
    2480             2485              2490

Pro Val Pro Thr Thr Ser Thr  Thr Ser Ser Pro Thr  Thr Ser Thr
    2495             2500              2505

Thr Ser Ala Pro Thr Thr Ser  Thr Thr Ser Ala Ser  Thr Thr Ser
    2510             2515              2520

Thr Thr Ser Gly Ala Gly Thr  Thr Pro Ser Pro Val  Pro Thr Thr
    2525             2530              2535

Ser Thr Thr Ser Ala Pro Thr  Thr Ser Thr Thr Ser  Ala Pro Ile
    2540             2545              2550

Ser Ser Thr Thr Ser Ala Thr  Thr Thr Ser Thr Thr  Ser Gly Pro
    2555             2560              2565

Gly Thr Thr Pro Ser Pro Val  Pro Thr Thr Ser Thr  Thr Ser Ala
    2570             2575              2580

Pro Thr Thr Ser Thr Thr Ser  Gly Pro Gly Thr Thr  Pro Ser Ala
    2585             2590              2595

Val Pro Thr Thr Ser Ile Thr  Ser Ala Pro Thr Thr  Ser Thr Asn
    2600             2605              2610

Ser Ala Pro Ile Ser Ser Thr  Thr Ser Ala Thr Thr  Thr Ser Arg
    2615             2620              2625

Ile Ser Gly Pro Glu Thr Thr  Pro Ser Pro Val Pro  Thr Ala Ser
    2630             2635              2640

Thr Thr Ser Ala Ser Thr Thr  Ser Thr Thr Ser Gly  Pro Gly Thr
    2645             2650              2655

Thr Pro Ser Pro Val Pro Thr  Thr Ser Thr Ile Ser  Val Pro Thr
    2660             2665              2670

Thr Ser Thr Thr Ser Ala Ser  Thr Thr Ser Thr Thr  Ser Ala Ser
    2675             2680              2685

Thr Thr Ser Thr Thr Ser Gly  Pro Gly Thr Thr Pro  Ser Pro Val
    2690             2695              2700

Pro Thr Thr Ser Thr Thr Ser  Ala Pro Thr Thr Ser  Thr Thr Ser
    2705             2710              2715

Ala Pro Thr Thr Ser Thr Ile  Ser Ala Pro Thr Thr  Ser Thr Thr
    2720             2725              2730

Ser Ala Thr Thr Thr Ser Thr  Thr Ser Ala Pro Thr  Pro Arg Arg
    2735             2740              2745

Thr Ser Ala Pro Thr Thr Ser  Thr Ile Ser Ala Ser  Thr Thr Ser
    2750             2755              2760

Thr Thr Ser Ala Thr Thr Thr  Ser Thr Thr Ser Ala  Thr Thr Thr
    2765             2770              2775
```

-continued

```
Ser Thr  Ile Ser Ala Pro Thr  Thr Ser Thr Thr Leu  Ser Pro Thr
    2780             2785                 2790

Thr Ser  Thr Thr Ser Thr Thr  Ile Thr Ser Thr Thr  Ser Ala Pro
    2795             2800                 2805

Ile Ser  Ser Thr Thr Ser Thr  Pro Gln Thr Ser Thr  Thr Ser Ala
    2810             2815                 2820

Pro Thr  Thr Ser Thr Thr Ser  Gly Pro Gly Thr Thr  Ser Ser Pro
    2825             2830                 2835

Val Pro  Thr Thr Ser Thr Thr  Ser Ala Pro Thr Thr  Ser Thr Thr
    2840             2845                 2850

Ser Ala  Pro Thr Thr Arg Thr  Thr Ser Val Pro Thr  Ser Ser Thr
    2855             2860                 2865

Thr Ser  Thr Ala Thr Thr Ser  Thr Thr Ser Gly Pro  Gly Thr Thr
    2870             2875                 2880

Pro Ser  Pro Val Pro Thr Thr  Ser Thr Thr Ser Ala  Pro Thr Thr
    2885             2890                 2895

Arg Thr  Thr Ser Ala Pro Thr  Thr Ser Thr Thr Ser  Ala Pro Thr
    2900             2905                 2910

Thr Ser  Thr Thr Ser Ala Pro  Thr Ser Ser Thr Thr  Ser Ala Thr
    2915             2920                 2925

Thr Thr  Ser Thr Ile Ser Val  Pro Thr Thr Ser Thr  Thr Ser Val
    2930             2935                 2940

Pro Gly  Thr Thr Pro Ser Pro  Val Pro Thr Thr Ser  Thr Ile Ser
    2945             2950                 2955

Val Pro  Thr Thr Ser Thr Thr  Ser Ala Ser Thr Thr  Ser Thr Thr
    2960             2965                 2970

Ser Gly  Pro Gly Thr Thr Pro  Ser Pro Val Pro Thr  Thr Ser Thr
    2975             2980                 2985

Thr Ser  Ala Pro Thr Thr Ser  Thr Thr Ser Ala Pro  Thr Thr Ser
    2990             2995                 3000

Thr Ile  Ser Ala Pro Thr Thr  Ser Thr Pro Ser Ala  Pro Thr Thr
    3005             3010                 3015

Ser Thr  Thr Leu Ala Pro Thr  Thr Ser Thr Thr Ser  Ala Pro Thr
    3020             3025                 3030

Thr Ser  Thr Thr Ser Thr Pro  Thr Ser Ser Thr Thr  Ser Ser Pro
    3035             3040                 3045

Gln Thr  Ser Thr Thr Ser Ala  Ser Thr Thr Ser Ile  Thr Ser Gly
    3050             3055                 3060

Pro Gly  Thr Thr Pro Ser Pro  Val Pro Thr Thr Ser  Thr Thr Ser
    3065             3070                 3075

Ala Pro  Thr Thr Ser Thr Thr  Ser Ala Ala Thr Thr  Ser Thr Ile
    3080             3085                 3090

Ser Ala  Pro Thr Thr Ser Thr  Thr Ser Ala Pro Thr  Thr Ser Thr
    3095             3100                 3105

Thr Ser  Ala Ser Thr Ala Ser  Lys Thr Ser Gly Leu  Gly Thr Thr
    3110             3115                 3120

Pro Ser  Pro Ile Pro Thr Thr  Ser Thr Thr Ser Pro  Pro Thr Thr
    3125             3130                 3135

Ser Thr  Thr Ser Ala Ser Thr  Ala Ser Lys Thr Ser  Gly Pro Gly
    3140             3145                 3150

Thr Thr  Pro Ser Pro Val Pro  Thr Thr Ser Thr Ile  Phe Ala Pro
    3155             3160                 3165

Arg Thr  Ser Thr Thr Ser Ala  Ser Thr Thr Ser Thr  Thr Pro Gly
```

-continued

```
     3170              3175              3180

Pro Gly Thr Thr Pro Ser Pro  Val Pro Thr Thr Ser  Thr Ala Ser
     3185              3190              3195

Val Ser Lys Thr Ser Thr Ser  His Val Ser Ile Ser  Lys Thr Thr
     3200              3205              3210

His Ser Gln Pro Val Thr Arg  Asp Cys His Leu Arg  Cys Thr Trp
     3215              3220              3225

Thr Lys Trp Phe Asp Ile Asp  Phe Pro Ser Pro Gly  Pro His Gly
     3230              3235              3240

Gly Asp Lys Glu Thr Tyr Asn  Asn Ile Ile Arg Ser  Gly Glu Lys
     3245              3250              3255

Ile Cys Arg Arg Pro Glu Glu  Ile Thr Arg Leu Gln  Cys Arg Ala
     3260              3265              3270

Glu Ser His Pro Glu Val Ser  Ile Glu His Leu Gly  Gln Val Val
     3275              3280              3285

Gln Cys Ser Arg Glu Glu Gly  Leu Val Cys Arg Asn  Gln Asp Gln
     3290              3295              3300

Gln Gly Pro Phe Lys Met Cys  Leu Asn Tyr Glu Val  Arg Val Leu
     3305              3310              3315

Cys Cys Glu Thr Pro Lys Gly  Cys Pro Val Thr Ser  Thr Pro Val
     3320              3325              3330

Thr Ala Pro Ser Thr Pro Ser  Gly Arg Ala Thr Ser  Pro Thr Gln
     3335              3340              3345

Ser Thr Ser Ser Trp Gln Lys  Ser Arg Thr Thr Thr  Leu Val Thr
     3350              3355              3360

Thr Ser Thr Thr Ser Thr Pro  Gln Thr Ser Thr Thr  Ser Ala Pro
     3365              3370              3375

Thr Thr Ser Thr Thr Ser Ala  Pro Thr Thr Ser Thr  Thr Ser Ala
     3380              3385              3390

Pro Thr Thr Ser Thr Thr Ser  Thr Pro Gln Thr Ser  Ile Ser Ser
     3395              3400              3405

Ala Pro Thr Ser Ser Thr Thr  Ser Ala Pro Thr Ser  Ser Thr Ile
     3410              3415              3420

Ser Ala Arg Thr Thr Ser Ile  Ile Ser Ala Pro Thr  Thr Ser Thr
     3425              3430              3435

Thr Ser Ser Pro Thr Thr Ser  Thr Thr Ser Ala Thr  Thr Thr Ser
     3440              3445              3450

Thr Thr Ser Ala Pro Thr Ser  Ser Thr Thr Ser Thr  Pro Gln Thr
     3455              3460              3465

Ser Lys Thr Ser Ala Ala Thr  Ser Ser Thr Thr Ser  Gly Ser Gly
     3470              3475              3480

Thr Thr Pro Ser Pro Val Thr  Thr Thr Ser Thr Ala  Ser Val Ser
     3485              3490              3495

Lys Thr Ser Thr Ser His Val  Ser Val Ser Lys Thr  Thr His Ser
     3500              3505              3510

Gln Pro Val Thr Arg Asp Cys  His Pro Arg Cys Thr  Trp Thr Lys
     3515              3520              3525

Trp Phe Asp Val Asp Phe Pro  Ser Pro Gly Pro His  Gly Gly Asp
     3530              3535              3540

Lys Glu Thr Tyr Asn Asn Ile  Ile Arg Ser Gly Glu  Lys Ile Cys
     3545              3550              3555

Arg Arg Pro Glu Glu Ile Thr  Arg Leu Gln Cys Arg  Ala Lys Ser
     3560              3565              3570
```

-continued

```
His Pro Glu Val Ser Ile Glu  His Leu Gly Gln Val  Val Gln Cys
    3575                3580                 3585

Ser Arg Glu Glu Gly Leu Val  Cys Arg Asn Gln Asp  Gln Gln Gly
    3590                3595                 3600

Pro Phe Lys Met Cys Leu Asn  Tyr Glu Val Arg Val  Leu Cys Cys
    3605                3610                 3615

Glu Thr Pro Lys Gly Cys Pro  Val Thr Ser Thr Ser  Val Thr Ala
    3620                3625                 3630

Pro Ser Thr Pro Ser Gly Arg  Ala Thr Ser Pro Thr  Gln Ser Thr
    3635                3640                 3645

Ser Ser Trp Gln Lys Ser Arg  Thr Thr Thr Leu Val  Thr Ser Ser
    3650                3655                 3660

Ile Thr Ser Thr Thr Gln Thr  Ser Thr Thr Ser Ala  Pro Thr Thr
    3665                3670                 3675

Ser Thr Thr Pro Ala Ser Ile  Pro Ser Thr Thr Ser  Ala Pro Thr
    3680                3685                 3690

Thr Ser Thr Thr Ser Ala Pro  Thr Thr Ser Thr Thr  Ser Ala Pro
    3695                3700                 3705

Thr Thr Ser Thr Thr Ser Thr  Pro Gln Thr Thr Thr  Ser Ser Ala
    3710                3715                 3720

Pro Thr Ser Ser Thr Thr Ser  Ala Pro Thr Thr Ser  Thr Ile Ser
    3725                3730                 3735

Ala Pro Thr Thr Ser Thr Ile  Ser Ala Pro Thr Thr  Ser Thr Thr
    3740                3745                 3750

Ser Ala Pro Thr Ala Ser Thr  Thr Ser Ala Pro Thr  Ser Thr Ser
    3755                3760                 3765

Ser Ala Pro Thr Thr Asn Thr  Thr Ser Ala Pro Thr  Thr Ser Thr
    3770                3775                 3780

Thr Ser Ala Pro Ile Thr Ser  Thr Ile Ser Ala Pro  Thr Thr Ser
    3785                3790                 3795

Thr Thr Ser Thr Pro Gln Thr  Ser Thr Ile Ser Ser  Pro Thr Thr
    3800                3805                 3810

Ser Thr Thr Ser Thr Pro Gln  Thr Ser Thr Thr Ser  Ser Pro Thr
    3815                3820                 3825

Thr Ser Thr Thr Ser Ala Pro  Thr Thr Ser Thr Thr  Ser Ala Pro
    3830                3835                 3840

Thr Thr Ser Thr Thr Ser Thr  Pro Gln Thr Ser Ile  Ser Ser Ala
    3845                3850                 3855

Pro Thr Ser Ser Thr Thr Ser  Ala Pro Thr Ala Ser  Thr Ile Ser
    3860                3865                 3870

Ala Pro Thr Thr Ser Thr Thr  Ser Phe His Thr Thr  Ser Thr Thr
    3875                3880                 3885

Ser Pro Pro Thr Ser Ser Thr  Ser Ser Thr Pro Gln  Thr Ser Lys
    3890                3895                 3900

Thr Ser Ala Ala Thr Ser Ser  Thr Thr Ser Gly Ser  Gly Thr Thr
    3905                3910                 3915

Pro Ser Pro Val Pro Thr Thr  Ser Thr Ala Ser Val  Ser Lys Thr
    3920                3925                 3930

Ser Thr Ser His Val Ser Val  Ser Lys Thr Thr His  Ser Gln Pro
    3935                3940                 3945

Val Thr Arg Asp Cys His Pro  Arg Cys Thr Trp Thr  Lys Trp Phe
    3950                3955                 3960
```

```
Asp Val Asp Phe Pro Ser Pro  Gly Pro His Gly Gly  Asp Lys Glu
    3965              3970              3975

Thr Tyr Asn Asn Ile Ile Arg  Ser Gly Glu Lys Ile  Cys Arg Arg
    3980              3985              3990

Pro Glu Glu Ile Thr Arg Leu  Gln Cys Arg Ala Glu  Ser His Pro
    3995              4000              4005

Glu Val Ser Ile Glu His Leu  Gly Gln Val Val Gln  Cys Ser Arg
    4010              4015              4020

Glu Glu Gly Leu Val Cys Arg  Asn Gln Asp Gln Gln  Gly Pro Phe
    4025              4030              4035

Lys Met Cys Leu Asn Tyr Glu  Val Arg Val Leu Cys  Cys Glu Thr
    4040              4045              4050

Pro Lys Gly Cys Pro Val Thr  Ser Thr Pro Val Thr  Ala Pro Ser
    4055              4060              4065

Thr Pro Ser Gly Arg Ala Thr  Ser Pro Thr Gln Ser  Thr Ser Ser
    4070              4075              4080

Trp Gln Lys Ser Arg Thr Thr  Thr Leu Val Thr Thr  Ser Thr Thr
    4085              4090              4095

Ser Thr Pro Gln Thr Ser Thr  Thr Ser Ala Pro Thr  Thr Ser Thr
    4100              4105              4110

Ile Pro Ala Ser Thr Pro Ser  Thr Thr Ser Ala Pro  Thr Thr Ser
    4115              4120              4125

Thr Thr Ser Ala Pro Thr Thr  Ser Thr Thr Ser Ala  Pro Thr His
    4130              4135              4140

Arg Thr Thr Ser Gly Pro Thr  Thr Ser Thr Thr Leu  Ala Pro Thr
    4145              4150              4155

Thr Ser Thr Thr Ser Ala Pro  Thr Thr Ser Thr Asn  Ser Ala Pro
    4160              4165              4170

Thr Thr Ser Thr Ile Ser Ala  Ser Thr Thr Ser Thr  Ile Ser Ala
    4175              4180              4185

Pro Thr Thr Ser Thr Ile Ser  Ser Pro Thr Ser Ser  Thr Thr Ser
    4190              4195              4200

Thr Pro Gln Thr Ser Lys Thr  Ser Ala Ala Thr Ser  Ser Thr Thr
    4205              4210              4215

Ser Gly Ser Gly Thr Thr Pro  Ser Pro Val Pro Thr  Thr Ser Thr
    4220              4225              4230

Thr Ser Ala Ser Thr Thr Ser  Thr Thr Ser Ala Pro  Thr Thr Ser
    4235              4240              4245

Thr Thr Ser Gly Pro Gly Thr  Thr Pro Ser Pro Val  Pro Ser Thr
    4250              4255              4260

Ser Thr Thr Ser Ala Ala Thr  Thr Ser Thr Thr Ser  Ala Pro Thr
    4265              4270              4275

Thr Arg Thr Thr Ser Ala Pro  Thr Ser Ser Met Thr  Ser Gly Pro
    4280              4285              4290

Gly Thr Thr Pro Ser Pro Val  Pro Thr Thr Ser Thr  Thr Ser Ala
    4295              4300              4305

Pro Thr Thr Ser Thr Thr Ser  Gly Pro Gly Thr Thr  Pro Ser Pro
    4310              4315              4320

Val Pro Thr Thr Ser Thr Thr  Ser Ala Pro Ile Thr  Ser Thr Thr
    4325              4330              4335

Ser Gly Pro Gly Ser Thr Pro  Ser Pro Val Pro Thr  Thr Ser Thr
    4340              4345              4350

Thr Ser Ala Pro Thr Thr Ser  Thr Thr Ser Ala Ser  Thr Ala Ser
```

-continued

```
     4355              4360              4365

Thr Thr  Ser Gly Pro Gly Thr  Thr Pro Ser Pro Val  Pro Thr Thr
     4370              4375              4380

Ser Thr  Thr Ser Ala Pro Thr  Thr Arg Thr Thr Ser  Ala Ser Thr
     4385              4390              4395

Ala Ser  Thr Thr Ser Gly Pro  Gly Ser Thr Pro Ser  Pro Val Pro
     4400              4405              4410

Thr Thr  Ser Thr Thr Ser Ala  Pro Thr Thr Arg Thr  Thr Pro Ala
     4415              4420              4425

Ser Thr  Ala Ser Thr Thr Ser  Gly Pro Gly Thr Thr  Pro Ser Pro
     4430              4435              4440

Val Pro  Thr Thr Ser Thr Thr  Ser Ala Ser Thr Thr  Ser Thr Ile
     4445              4450              4455

Ser Leu  Pro Thr Thr Ser Thr  Thr Ser Ala Pro Ile  Thr Ser Met
     4460              4465              4470

Thr Ser  Gly Pro Gly Thr Thr  Pro Ser Pro Val Pro  Thr Thr Ser
     4475              4480              4485

Thr Thr  Ser Ala Pro Thr Thr  Ser Thr Thr Ser Ala  Ser Thr Ala
     4490              4495              4500

Ser Thr  Thr Ser Gly Pro Gly  Thr Thr Pro Ser Pro  Val Pro Thr
     4505              4510              4515

Thr Ser  Thr Thr Ser Ala Pro  Thr Thr Ser Thr Thr  Ser Ala Ser
     4520              4525              4530

Thr Ala  Ser Thr Thr Ser Gly  Pro Gly Thr Ser Leu  Ser Pro Val
     4535              4540              4545

Pro Thr  Thr Ser Thr Thr Ser  Ala Pro Thr Thr Ser  Thr Thr Ser
     4550              4555              4560

Gly Pro  Gly Thr Thr Pro Ser  Pro Val Pro Thr Thr  Ser Thr Thr
     4565              4570              4575

Ser Ala  Pro Thr Thr Ser Thr  Thr Ser Gly Pro Gly  Thr Thr Pro
     4580              4585              4590

Ser Pro  Val Pro Thr Thr Ser  Thr Thr Pro Val Ser  Lys Thr Ser
     4595              4600              4605

Thr Ser  His Leu Ser Val Ser  Lys Thr Thr His Ser  Gln Pro Val
     4610              4615              4620

Thr Ser  Asp Cys His Pro Leu  Cys Ala Trp Thr Lys  Trp Phe Asp
     4625              4630              4635

Val Asp  Phe Pro Ser Pro Gly  Pro His Gly Gly Asp  Lys Glu Thr
     4640              4645              4650

Tyr Asn  Asn Ile Ile Arg Ser  Gly Glu Lys Ile Cys  Arg Arg Pro
     4655              4660              4665

Glu Glu  Ile Thr Arg Leu Gln  Cys Arg Ala Glu Ser  His Pro Glu
     4670              4675              4680

Val Asn  Ile Glu His Leu Gly  Gln Val Val Gln Cys  Ser Arg Glu
     4685              4690              4695

Glu Gly  Leu Val Cys Arg Asn  Gln Asp Gln Gln Gly  Pro Phe Lys
     4700              4705              4710

Met Cys  Leu Asn Tyr Glu Val  Arg Val Leu Cys Cys  Glu Thr Pro
     4715              4720              4725

Arg Gly  Cys Pro Val Thr Ser  Val Thr Pro Tyr Gly  Thr Ser Pro
     4730              4735              4740

Thr Asn  Ala Leu Tyr Pro Ser  Leu Ser Thr Ser Met  Val Ser Ala
     4745              4750              4755
```

```
Ser Val  Ala Ser Thr Ser Val  Ala Ser Ser Ser Val  Ala Ser Ser
    4760             4765             4770

Ser Val  Ala Tyr Ser Thr Gln  Thr Cys Phe Cys Asn  Val Ala Asp
    4775             4780             4785

Arg Leu  Tyr Pro Ala Gly Ser  Thr Ile Tyr Arg His  Arg Asp Leu
    4790             4795             4800

Ala Gly  His Cys Tyr Tyr Ala  Leu Cys Ser Gln Asp  Cys Gln Val
    4805             4810             4815

Val Arg  Gly Val Asp Ser Asp  Cys Pro Ser Thr Thr  Leu Pro Pro
    4820             4825             4830

Ala Pro  Ala Thr Ser Pro Ser  Ile Ser Thr Ser Glu  Pro Val Thr
    4835             4840             4845

Glu Leu  Gly Cys Pro Asn Ala  Val Pro Pro Arg Lys  Lys Gly Glu
    4850             4855             4860

Thr Trp  Ala Thr Pro Asn Cys  Ser Glu Ala Thr Cys  Glu Gly Asn
    4865             4870             4875

Asn Val  Ile Ser Leu Arg Pro  Arg Thr Cys Pro Arg  Val Glu Lys
    4880             4885             4890

Pro Thr  Cys Ala Asn Gly Tyr  Pro Ala Val Lys Val  Ala Asp Gln
    4895             4900             4905

Asp Gly  Cys Cys His His Tyr  Gln Cys Gln Cys Val  Cys Ser Gly
    4910             4915             4920

Trp Gly  Asp Pro His Tyr Ile  Thr Phe Asp Gly Thr  Tyr Tyr Thr
    4925             4930             4935

Phe Leu  Asp Asn Cys Thr Tyr  Val Leu Val Gln Gln  Ile Val Pro
    4940             4945             4950

Val Tyr  Gly His Phe Arg Val  Leu Val Asp Asn Tyr  Phe Cys Gly
    4955             4960             4965

Ala Glu  Asp Gly Leu Ser Cys  Pro Arg Ser Ile Ile  Leu Glu Tyr
    4970             4975             4980

His Gln  Asp Arg Val Val Leu  Thr Arg Lys Pro Val  His Gly Val
    4985             4990             4995

Met Thr  Asn Glu Ile Ile Phe  Asn Asn Lys Val Val  Ser Pro Gly
    5000             5005             5010

Phe Arg  Lys Asn Gly Ile Val  Val Ser Arg Ile Gly  Val Lys Met
    5015             5020             5025

Tyr Ala  Thr Ile Pro Glu Leu  Gly Val Gln Val Met  Phe Ser Gly
    5030             5035             5040

Leu Ile  Phe Ser Val Glu Val  Pro Phe Ser Lys Phe  Ala Asn Asn
    5045             5050             5055

Thr Glu  Gly Gln Cys Gly Thr  Cys Thr Asn Asp Arg  Lys Asp Glu
    5060             5065             5070

Cys Arg  Thr Pro Arg Gly Thr  Val Val Ala Ser Cys  Ser Glu Met
    5075             5080             5085

Ser Gly  Leu Trp Asn Val Ser  Ile Pro Asp Gln Pro  Ala Cys His
    5090             5095             5100

Arg Pro  His Pro Thr Pro Thr  Thr Val Gly Pro Thr  Thr Val Gly
    5105             5110             5115

Ser Thr  Thr Val Gly Pro Thr  Thr Val Gly Ser Thr  Thr Val Gly
    5120             5125             5130

Pro Thr  Thr Pro Pro Ala Pro  Cys Leu Pro Ser Pro  Ile Cys Gln
    5135             5140             5145
```

-continued

```
Leu Ile  Leu Ser Lys Val Phe  Glu Pro Cys His Thr  Val Ile Pro
    5150                5155                5160

Pro Leu  Leu Phe Tyr Glu Gly  Cys Val Phe Asp Arg  Cys His Met
    5165                5170                5175

Thr Asp  Leu Asp Val Val Cys  Ser Ser Leu Glu Leu  Tyr Ala Ala
    5180                5185                5190

Leu Cys  Ala Ser His Asp Ile  Cys Ile Asp Trp Arg  Gly Arg Thr
    5195                5200                5205

Gly His  Met Cys Pro Phe Thr  Cys Pro Ala Asp Lys  Val Tyr Gln
    5210                5215                5220

Pro Cys  Gly Pro Ser Asn Pro  Ser Tyr Cys Tyr Gly  Asn Asp Ser
    5225                5230                5235

Ala Ser  Leu Gly Ala Leu Pro  Glu Ala Gly Pro Ile  Thr Glu Gly
    5240                5245                5250

Cys Phe  Cys Pro Glu Gly Met  Thr Leu Phe Ser Thr  Ser Ala Gln
    5255                5260                5265

Val Cys  Val Pro Thr Gly Cys  Pro Arg Cys Leu Gly  Pro His Gly
    5270                5275                5280

Glu Pro  Val Lys Val Gly His  Thr Val Gly Met Asp  Cys Gln Glu
    5285                5290                5295

Cys Thr  Cys Glu Ala Ala Thr  Trp Thr Leu Thr Cys  Arg Pro Lys
    5300                5305                5310

Leu Cys  Pro Leu Pro Pro Ala  Cys Pro Leu Pro Gly  Phe Val Pro
    5315                5320                5325

Val Pro  Ala Ala Pro Gln Ala  Gly Gln Cys Cys Pro  Gln Tyr Ser
    5330                5335                5340

Cys Ala  Cys Asn Thr Ser Arg  Cys Pro Ala Pro Val  Gly Cys Pro
    5345                5350                5355

Glu Gly  Ala Arg Ala Ile Pro  Thr Tyr Gln Glu Gly  Ala Cys Cys
    5360                5365                5370

Pro Val  Gln Asn Cys Ser Trp  Thr Val Cys Ser Ile  Asn Gly Thr
    5375                5380                5385

Leu Tyr  Gln Pro Gly Ala Val  Val Ser Ser Ser Leu  Cys Glu Thr
    5390                5395                5400

Cys Arg  Cys Glu Leu Pro Gly  Gly Pro Pro Ser Asp  Ala Phe Val
    5405                5410                5415

Val Ser  Cys Glu Thr Gln Ile  Cys Asn Thr His Cys  Pro Val Gly
    5420                5425                5430

Phe Glu  Tyr Gln Glu Gln Ser  Gly Gln Cys Cys Gly  Thr Cys Val
    5435                5440                5445

Gln Val  Ala Cys Val Thr Asn  Thr Ser Lys Ser Pro  Ala His Leu
    5450                5455                5460

Phe Tyr  Pro Gly Glu Thr Trp  Ser Asp Ala Gly Asn  His Cys Val
    5465                5470                5475

Thr His  Gln Cys Glu Lys His  Gln Asp Gly Leu Val  Val Val Thr
    5480                5485                5490

Thr Lys  Lys Ala Cys Pro Pro  Leu Ser Cys Ser Leu  Asp Glu Ala
    5495                5500                5505

Arg Met  Ser Lys Asp Gly Cys  Cys Arg Phe Cys Pro  Pro Pro Pro
    5510                5515                5520

Pro Pro  Tyr Gln Asn Gln Ser  Thr Cys Ala Val Tyr  His Arg Ser
    5525                5530                5535

Leu Ile  Ile Gln Gln Gln Gly  Cys Ser Ser Ser Glu  Pro Val Arg
```

-continued

```
        5540            5545            5550

Leu Ala  Tyr Cys Arg Gly Asn  Cys Gly Asp Ser Ser  Ser Met Tyr
    5555            5560            5565

Ser Leu  Glu Gly Asn Thr Val  Glu His Arg Cys Gln  Cys Cys Gln
    5570            5575            5580

Glu Leu  Arg Thr Ser Leu Arg  Asn Val Thr Leu His  Cys Thr Asp
    5585            5590            5595

Gly Ser  Ser Arg Ala Phe Ser  Tyr Thr Glu Val Glu  Glu Cys Gly
    5600            5605            5610

Cys Met  Gly Arg Arg Cys Pro  Ala Pro Gly Asp Thr  Gln His Ser
    5615            5620            5625

Glu Glu  Ala Glu Pro Glu Pro  Ser Gln Glu Ala Glu  Ser Gly Ser
    5630            5635            5640

Trp Glu  Arg Gly Val Pro Val  Ser Pro Met His
    5645            5650
```

<210> SEQ ID NO 17
<211> LENGTH: 458
<212> TYPE: PRT
<213> ORGANISM: artificial sequence
<220> FEATURE:
<223> OTHER INFORMATION: Human CD4 Amino Acid Sequence

<400> SEQUENCE: 17

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
            85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
            165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
```

-continued

```
                  245                250                255

Lys Asn Lys Glu Val Ser Val Lys Arg Val Thr Gln Asp Pro Lys Leu
              260                265                270

Gln Met Gly Lys Lys Leu Pro Leu His Leu Thr Leu Pro Gln Ala Leu
          275                280                285

Pro Gln Tyr Ala Gly Ser Gly Asn Leu Thr Leu Ala Leu Glu Ala Lys
      290                295                300

Thr Gly Lys Leu His Gln Glu Val Asn Leu Val Val Met Arg Ala Thr
  305                310                315                320

Gln Leu Gln Lys Asn Leu Thr Cys Glu Val Trp Gly Pro Thr Ser Pro
              325                330                335

Lys Leu Met Leu Ser Leu Lys Leu Glu Asn Lys Glu Ala Lys Val Ser
              340                345                350

Lys Arg Glu Lys Ala Val Trp Val Leu Asn Pro Glu Ala Gly Met Trp
              355                360                365

Gln Cys Leu Leu Ser Asp Ser Gly Gln Val Leu Leu Glu Ser Asn Ile
      370                375                380

Lys Val Leu Pro Thr Trp Ser Thr Pro Val Gln Pro Met Ala Leu Ile
  385                390                395                400

Val Leu Gly Gly Val Ala Gly Leu Leu Leu Phe Ile Gly Leu Gly Ile
              405                410                415

Phe Phe Cys Val Arg Cys Arg His Arg Arg Arg Gln Ala Glu Arg Met
              420                425                430

Ser Gln Ile Lys Arg Leu Leu Ser Glu Lys Lys Thr Cys Gln Cys Pro
          435                440                445

His Arg Phe Gln Lys Thr Cys Ser Pro Ile
      450                455
```

<210> SEQ ID NO 18
<211> LENGTH: 771
<212> TYPE: DNA
<213> ORGANISM: artificial sequence
<220> FEATURE:
<223> OTHER INFORMATION: Alpha Chain

<400> SEQUENCE: 18

```
cagacagtca ctcagtctca accagagatg tctgtgcagg aggcagagac tgtgaccctg      60
agttgcacat atgacaccag tgagagtaat tattatttgt tctggtacaa acagcctccc     120
agcaggcaga tgattctcgt tattcgccaa gaagcttata agcaacagaa tgcaacggag     180
aatcgtttct ctgtgaactt ccagaaagca gccaaatcct tcagtctcaa gatctcagac     240
tcacagctgg gggacactgc gatgtatttc tgtgctttca tgaagcgggc cgaaaccagt     300
ggctctaggt tgacctttgg ggaaggaaca cagctcacag tgaatcctga tatccagaac     360
cctgaccctg ccgtgtacca gctgagagac tctaaatcca gtgacaagtc tgtctgccta     420
ttcaccgatt ttgattctca aacaaatgtg tcacaaagta aggattctga tgtgtatatc     480
acagacaaaa ctgtgctaga catgaggtct atggacttca gagcaacag tgctgtggcc      540 tggagcaaca atctgactt tgcatgtgca aacgccttca caacagcat tattccagaa       600 gacaccttct tccccagccc agaaagttcc tgtgatgtca gctggtcga gaaaagcttt       660 gaaacagata cgaacctaaa ctttcaaaac ctgtcagtga ttgggttccg aatcctcctc     720
ctgaaagtgg ccgggtttaa tctgctcatg acgctgcggc tgtggtccag c              771
```

<210> SEQ ID NO 19

-continued

```
<211> LENGTH: 876
<212> TYPE: DNA
<213> ORGANISM: artificial sequence
<220> FEATURE:
<223> OTHER INFORMATION: Beta Chain

<400> SEQUENCE: 19
aatgctggtg tcactcagac cccaaaattc cgggtcctga agacaggaca gagcatgaca      60
ctgctgtgtg ctcaggatat gaaccatgaa tacatgtact ggtatcgaca agacccaggc     120
atggggctga ggctgattca ttactcagtt ggtgagggta caactgccaa aggagaggtc     180
cctgatggct acaatgtctc cagattaaaa aaacagaatt tcctgctggg gttggagtcg     240
gctgctccct cccaaacatc tgtgtacttc tgtgccagca gttactggcc gacgcgggag     300
acccagtact cgggccagg cacgcggctc ctggtgctcg aggacctgaa aaacgtgttc     360
ccacccgagg tcgctgtgtt tgagccatca gaagcagaga tctcccacac ccaaaaggcc     420
acactggtat gcctggccac aggcttctac cccgaccacg tggagctgag ctggtgggtg     480
aatgggaagg aggtgcacag tggggtcagc acagacccgc agcccctcaa ggagcagccc     540
gccctcaatg actccagata ctgcctgagc agccgcctga gggtctcggc caccttctgg     600 cagaacccc gcaaccactt ccgctgtcaa gtccagttct acgggctctc ggagaatgac     660
gagtggaccc aggatagggc caaacctgtc acccagatcg tcagcgccga ggcctggggt     720
agagcagact gtggcttcac ctccgagtct taccagcaag gggtcctgtc tgccaccatc     780
ctctatgaga tcttgctagg gaaggccacc ttgtatgccg tgctggtcag tgccctcgtg     840
ctgatggcca tggtcaagag aaaggatagc agaggc                              876
```

```
<210> SEQ ID NO 20
<211> LENGTH: 17
<212> TYPE: PRT
<213> ORGANISM: artificial sequence
<220> FEATURE:
<223> OTHER INFORMATION: Signal Peptide (Fibroin-L derived)

<400> SEQUENCE: 20

Met Met Arg Pro Ile Val Leu Val Leu Leu Phe Ala Thr Ser Ala Leu
1               5                   10                  15

Ala
```

```
<210> SEQ ID NO 21
<211> LENGTH: 21
<212> TYPE: PRT
<213> ORGANISM: artificial sequence
<220> FEATURE:
<223> OTHER INFORMATION: Alpha Chain Signal Peptide

<400> SEQUENCE: 21

Met Thr Arg Val Ser Leu Leu Trp Ala Val Val Val Ser Thr Cys Leu
1               5                   10                  15

Glu Ser Gly Met Ala
            20
```

```
<210> SEQ ID NO 22
<211> LENGTH: 15
<212> TYPE: PRT
<213> ORGANISM: artificial sequence
<220> FEATURE:
<223> OTHER INFORMATION: Beta Chain Signal Peptide

<400> SEQUENCE: 22
```

-continued

```
Met Gly Ala Val Ala Ser Ala Leu Ser Phe Ser Ala Gly Pro Val
1               5                   10                  15
```

<210> SEQ ID NO 23
<211> LENGTH: 63
<212> TYPE: DNA
<213> ORGANISM: artificial sequence
<220> FEATURE:
<223> OTHER INFORMATION: Alpha Chain Signal Peptide

<400> SEQUENCE: 23
atgacacgtg ttagcttgct gtgggcagtc gtggtctcca cctgtcttga atccggcatg      60
gcc                                                                    63

<210> SEQ ID NO 24
<211> LENGTH: 45
<212> TYPE: DNA
<213> ORGANISM: artificial sequence
<220> FEATURE:
<223> OTHER INFORMATION: Beta Chain Signal Peptide

<400> SEQUENCE: 24
atgggggctg tagcatcagc tttgtccttc tctgcaggtc cagtg                      45

<210> SEQ ID NO 25
<211> LENGTH: 21
<212> TYPE: DNA
<213> ORGANISM: artificial sequence
<220> FEATURE:
<223> OTHER INFORMATION: siRNA-TCRa-1

<400> SEQUENCE: 25
guaaggauuc ugauguguat t                                                21

<210> SEQ ID NO 26
<211> LENGTH: 21
<212> TYPE: DNA
<213> ORGANISM: artificial sequence
<220> FEATURE:
<223> OTHER INFORMATION: siRNA-TCRa-2

<400> SEQUENCE: 26
uacacaucag aauccuuact t                                                21

<210> SEQ ID NO 27
<211> LENGTH: 21
<212> TYPE: DNA
<213> ORGANISM: artificial sequence
<220> FEATURE:
<223> OTHER INFORMATION: siRNA-TCRb-1

<400> SEQUENCE: 27
ccaccauccu cuaugagaut t                                                21

<210> SEQ ID NO 28
<211> LENGTH: 21
<212> TYPE: DNA
<213> ORGANISM: artificial sequence
<220> FEATURE:
<223> OTHER INFORMATION: siRNA-TCRb-2

<400> SEQUENCE: 28
aucucauaga ggaugguggt t                                                21

<210> SEQ ID NO 29
```

```
<211> LENGTH: 37
<212> TYPE: PRT
<213> ORGANISM: artificial sequence
<220> FEATURE:
<223> OTHER INFORMATION: MUC5AC minigene

<400> SEQUENCE: 29

Met His Tyr Gln Cys Gln Cys Val Cys Ser Gly Trp Gly Asp Pro His
1               5                   10                  15

Tyr Ile Thr Phe Asp Gly Thr Tyr Tyr Thr Phe Leu Asp Asn Cys Thr
            20                  25                  30

Tyr Val Leu Val Gln
        35

<210> SEQ ID NO 30
<211> LENGTH: 4
<212> TYPE: PRT
<213> ORGANISM: artificial sequence
<220> FEATURE:
<223> OTHER INFORMATION: Glycine Serine Bridge

<400> SEQUENCE: 30

Gly Gly Gly Ser
1
```